(12) United States Patent
Stelzer et al.

(10) Patent No.: US 10,522,239 B2
(45) Date of Patent: Dec. 31, 2019

(54) SMALL MOLECULE BINDING POCKETS IN NUCLEIC ACIDS

(71) Applicant: Nymirum, Inc., Ann Arbor, MI (US)

(72) Inventors: Andrew Corbet Stelzer, Ann Arbor, MI (US); Mitchell Alan McBrairty, Ann Arbor, MI (US); Hashim M. Al-Hashimi, Ann Arbor, MI (US); Sung-Hun Bae, Ann Arbor, MI (US)

(73) Assignee: Nymirum, Inc., Ann Arbor, MI (US)

( * ) Notice: Subject to any disclaimer, the term of this patent is extended or adjusted under 35 U.S.C. 154(b) by 381 days.

(21) Appl. No.: 15/254,371

(22) Filed: Sep. 1, 2016

(65) Prior Publication Data

US 2017/0032078 A1    Feb. 2, 2017

Related U.S. Application Data

(63) Continuation-in-part of application No. 14/650,087, filed as application No. PCT/US2013/073330 on Dec. 5, 2013.

(60) Provisional application No. 61/733,784, filed on Dec. 5, 2012, provisional application No. 62/214,040, filed on Sep. 3, 2015.

(51) Int. Cl.
*G16B 15/00* (2019.01)
*G01N 24/08* (2006.01)
*G01N 33/68* (2006.01)
*G16B 35/00* (2019.01)
*G16C 20/60* (2019.01)

(52) U.S. Cl.
CPC ........... *G16B 15/00* (2019.02); *G01N 24/087* (2013.01); *G01N 33/6845* (2013.01); *G16B 35/00* (2019.02); *G16C 20/60* (2019.02)

(58) Field of Classification Search
CPC .. G01N 24/087; G01N 33/6845; G16B 15/00; G16B 35/00; G16C 20/60
See application file for complete search history.

(56) References Cited

U.S. PATENT DOCUMENTS

| | | | |
|---|---|---|---|
| 7,704,923 | B2 | 4/2010 | Xiang et al. |
| 8,498,823 | B2 | 7/2013 | Al-Hashimi et al. |
| 8,587,314 | B2 | 11/2013 | Burns |
| 2004/0038216 | A1 | 2/2004 | Hajduk |
| 2005/0234652 | A1 | 10/2005 | Sem |
| 2007/0166730 | A1 | 7/2007 | Menon et al. |
| 2015/0300968 | A1 | 10/2015 | Bae et al. |

OTHER PUBLICATIONS

Filikov et al. (Journal of Computer-Aided Molecular Design, 2000, 14:593-610) (Year: 2000).*

(Continued)

*Primary Examiner* — Jeremy C Flinders
(74) *Attorney, Agent, or Firm* — Wagenknecht IP Law Group PC

(57) ABSTRACT

Described herein is technology for determining the 2-D or 3-D atomic resolution structure of a polynucleotide bound to and/or interacting with another molecule, for example a small molecule. In some aspects of the technology, NMR and isotopic labeling strategies are used. The technology described herein is useful for a plurality of applications including but not limited to drug discovery and chemical biology probe discovery.

15 Claims, 11 Drawing Sheets

Specification includes a Sequence Listing.

(56) References Cited

OTHER PUBLICATIONS

PCT/US2013/073330 International Search Report dated May 13, 2014.
Bryce et al. "Measurement of Ribose Carbon Chemical Shift Tensors for A-form RNA by Liquid Crystal NMR Spectroscopy." J. Am. Chem. Soc., 2005, 127:7387-7396, Am. Chem. Soc.
Arun and Langmead. "Structure Based Chemical Shift Prediction Using Random Forests Non-Linear Regression." Carnegie Mellon University Computer Science Department, 2005, Paper 1071.
EP13860225.5 European Search Report dated Oct. 21, 2016.
Gray et al. "Easy, Robust and Accurate NMR Analysis of Biomolecules using Biopack—Technical Overview." Agilent Technologies Inc., 2011, Retrieved from internet http://www.agilent.com/cs/library/technicaloverviews/public/5990-9067en_lo.pdf [retrieved on Nov. 11, 2016].
Kalbitzer et al. "Structure Determination of Polypeptides and Proteins by Two-Dimensional Nuclear Magnetic Resonance Spectroscopy." Physica B Condensed Matter, Jun. 1990, 164(1-2)180-192, Amsterdam, NL.
Oholenschlaeger et al. "Nuclear Magnetic Resonance Studies of Ribonucleic Acids." Spectroscopy, Jan. 2003, 17(2-3)537-547.
Bodenhausen et al. "Natural Abundance Nitrogen-15 NMR by Enhanced Heteronuclear Spectrosopy," Chemical Physics Letters, Jan. 1, 1980, 69(1):185-189.

* cited by examiner 0.84 & 0.20    0.88 & 0.21    0.97 & 0.22    0.98 & 0.21    1.00 & 0.23

SMALL MOLECULE BINDING POCKETS IN NUCLEIC ACIDS

CROSS REFERENCE TO RELATED APPLICATIONS

This application is a continuation-in-part of U.S. patent application Ser. No. 14/650,087, filed Jun. 5, 2015, currently pending, which is a 35 U.S.C. § 371(c) U.S. National Phase filing of International Patent Application Serial No. PCT/US2013/073330, filed Dec. 5, 2013, which claims the benefit of priority to U.S. Provisional Application No. 61/733,784, filed Dec. 5, 2012. This application also claims the benefit of priority to U.S. Provisional Application No. 62/214,040, filed Sep. 3, 2015. The entire contents of each of the aforementioned disclosures are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 28, 2016, is named 20297-101169_SL.txt and is 1,149 bytes in size.

BACKGROUND

Nucleic acids are being targeted to treat various diseases. Tools to rapidly identify molecules that bind nucleic acids are beneficial to the drug discovery process.

SUMMARY OF THE INVENTION

The central dogma of molecular biology, DNA→RNA→Protein, has undergone a significant revision. Rather than being merely a messenger of genetic information, RNAs have emerged as key regulators of numerous cell activities. Astonishingly, as much as 80% of the human genome is transcribed into functional non-coding RNAs (ncRNAs), many of which are presumed to be involved in cellular transactions. Of particular importance are recent discoveries showing that ncRNAs are involved in causing or promoting diseases such as cancer, hepatitis C infection, myotonic dystrophy type 1, prostate cancer, spinal muscular atrophy, and Huntington's disease-like 2. In light of the increasing number of discoveries indicating that RNAs are responsible for some human pathologies, the pharmaceutical and biotech industries continue to initiate an increasing number of RNA targeting drug discovery programs. Due to delivery issues that have prevented success of using antisense oligonucleotides (ASOs) to inhibit miRNA overexpression, small molecules are being pursued as RNA-targeting drugs. Tools to rapidly, efficiently, and cost-effectively identify small molecules that bind nucleic acids are needed.

Nucleic acids, for example microRNAs (miRNAs), play a crucial role in the initiation and development of many human diseases, especially cancer. In fact, the widespread involvement of RNAs in cancer development has spurred the pharmaceutical and biotech to target them for anti-cancer therapies. Current efforts to target cancer-regulating and/or cancer-causing RNAs focus on ASOs. However, delivery of ASOs has been limited to accessible tissues such as the liver, kidney, spleen, and to a certain extent the lungs. When targeting harder to reach tissues, for example muscle and solid tumors, carefully designed and formulated carrier particles have been unsuccessfully attempted. As such, small molecule drugs are being pursued.

Using small molecules to alter biological function is a classic approach with a track record of success and overcomes many of the delivery issues facing ASO-based therapies. In addition to the subject matter described herein, several reports have demonstrated small molecules can be used to effectively target miRNAs and alter activity. For example, small molecules have been identified to alter the processing of miR-96, miR-21, miR-122, miR-210, miR-182, miR-27a, miR-1, miR-372/373, miR-29a. These studies all use indirect reporters of miRNA activity, for example, luciferase-based screening, GFP-based screening, and molecular beacon assays. Most reported miRNA binders are classic RNA binding small molecules (e.g., aminoglycosides). Only one study has confirmed small molecules alter expression by binding a miRNA. Moreover, due to poor understanding of miRNA structural biology and the lack of miRNA-Dicer or RISC complex structure, rational design of small molecule modifications to improve miRNA binding affinity and activity remains a significant challenge.

Pharmaceutical and biotech companies are increasing their efforts to find small molecules that alter RNA function. In some embodiments, small molecule drug discovery programs utilize structure-based drug design methods, however, current approaches to interrogate binding interactions between RNAs and small molecules have been unsuccessful. Traditional approaches such as x-ray crystallography and classic Nuclear Magnetic Resonance methods are prohibitively time consuming and expensive. Further, in some embodiments, these approaches do not account for the inherent plasticity of RNA, which is prevalent in miRNAs, thus preventing accurate atomic-level interpretation the data. While methods relying solely on molecular modeling have been reported, none have proven useful in the drug discovery process.

In some aspects, the subject matter described herein fits squarely within the drug discovery paradigm used in pharmaceutical and biotech injuries. In a first example, the subject matter described herein exploits nucleic acid (e.g., RNA) plasticity to solve atomic-resolution nucleic acid (e.g., RNA) structures and uncover binding pockets optimized to identify key small molecule-nucleic acid (e.g., RNA) interactions. In various embodiments, these binding pockets afford efficient hit identification with atomic-level guidance during target screening. In a second example, in pursuing small molecules for hit-to-lead studies and lead optimization, the atomic-level interactions enable medicinal chemists to rationally design new compounds. In some embodiments, this affords accurate and efficient target validation. In a third example, analogous to drug-target protein families such as GPCRs, nuclear hormone receptors, and kinases, the subject matter described herein enables targeting of all disease-regulating, nucleic acids, for example RNAs and miRNAs—the largest known RNA drug-target class.

In some aspects, the present invention provides a method for determining the 2-D or 3-D atomic resolution structure of a polynucleotide. The method includes providing a polynucleotide sample comprising a polynucleotide, the polynucleotide comprising at least one nucleotide isotopically labeled with one or more atomic labels selected from the group consisting of $^2$H, $^{13}$C, $^{15}$N, $^{19}$F and $^{31}$P; obtaining a NMR spectrum of the polynucleotide sample using a NMR device; determining a chemical shift of the one or more atomic labels; and determining a 2-D or a 3-D atomic resolution structure of the polynucleotide from the chemical shifts determined in step (c).

In some embodiments, the method to determine the 2-D or 3-D structure of a polynucleotide requires interrogation of multiple polynucleotides having the same nucleotide sequence, but differing from each other in that each polynucleotide is isotopically labeled on a different nucleotide. In other words, the method determines the chemical shifts of multiple polynucleotides, each polynucleotide having the identical nucleotide sequence as the first polynucleotide analyzed, and each polynucleotide is synthesized with a different nucleotide labeled with the one or more atomic labels. For example, if the polynucleotide has 5 nucleotides, the method would require 5 polynucleotide samples, each polynucleotide labeled with the one or more atomic labels on a different nucleotide. In this same 5-mer polynucleotide example, the method may utilize a smaller number of distinct polynucleotides that the number of nucleotides present in the nucleotide sequence, by strategically labeling one or more nucleotides in the polynucleotide with one or more atomic labels as described herein. In some embodiments, the polynucleotide sample has only one polynucleotide with one nucleotide labeling pattern. In other embodiments, the polynucleotide sample may contain two or more polynucleotides, each having a different nucleotide labeled with one or more atomic labels.

In some aspects, the method obtains a NMR spectrum of the polynucleotide sample by interrogating the polynucleotide sample with a NMR spectrometer frequency ranging from about 1 GHz MHz to about 20 MHz. In one of these aspects, the NMR spectrometer frequency is 300 MHz or less, for example, from about 20 MHz to about 100 MHz.

In some aspects, the present invention provides methods for determining the structure of a target biomolecule when mixed with a small molecule, biomolecule, ligand or other chemical entity (collectively referred to as a ligand) that could interact with the biomolecule of interest. Chemical shift changes on the addition of the ligand indicates that the biomolecule may be interacting with the ligand. The chemical shifts in the presence of the ligand can be collected and used to determine the bimolecular structure of the biomolecule and the bound ligand. In some embodiments of this aspect, the method includes the steps of providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2$H, $^{13}$C, $^{15}$N, $^{19}$F and $^{31}$P; admixing the polynucleotide sample with the ligand forming a plurality of bound complexes; obtaining a NMR spectrum of the bound complexes using a NMR device; determining a chemical shift of the one or more atomic labels; and determining the 3-D atomic resolution structure of the polynucleotides from the chemical shifts determined in step (d).

In some embodiments of the present methods, the target polynucleotide is analyzed by creating a plurality of polynucleotides all having the same nucleotide sequence but differing in the location(s) of isotopically labeled nucleotide(s). In some embodiments, the secondary structure of the polynucleotide is used to determine the placement of the labeled nucleotide or nucleotides to reduce the number of polynucleotide samples. Taking the primary sequence of the polynucleotide, the secondary structure is predicted. Then a plurality of secondary structure predictions can be computed using a secondary structure prediction algorithm (e.g., nearest neighbor algorithm) or computer program. The method then uses an alignment step with the top 10 or so secondary structure predictions and then determines the sites that exhibit the greatest variance in secondary structure. Then the site or sites in the polynucleotide sequence that exhibit largest variance are labeled isotopically for NMR detection or a derivative, wherein one or more nucleotides are labeled per polynucleotide. The labeling scheme can be informed from the chemical shift database whereby multiple isotopic labels can be incorporated into a polynucleotide while maximizing chemical shift dispersion.

In some embodiments, the present invention provides a method for determining one or more specific isotopic labeling positions of one or more nucleotides within a polynucleotide sequence for the determination of 3-D atomic resolution structure or collecting other NMR interaction data of a polynucleotide. The method includes providing one or more polynucleotides each of the one or more polynucleotides having an identical polynucleotide sequence, wherein each of the one or more polynucleotides comprises one or more nucleotides labeled with an isotopic label comprising, $^2$H, $^{13}$C, $^{15}$N, $^{19}$F or $^{31}$P; predicting a plurality of structures of the polynucleotide sequence using a computational algorithm (e.g., MC-Sym); identifying one or more region(s) on each of the plurality of polynucleotide structures that exhibit a large structural variation using metrics comprising an S2<0.8 and/or RMSF>0.5 Å; calculating a plurality of chemical shifts from regions of the predicted structures having a large structural variation using a chemical shift predictor; such as Nymirum's RANDOM FOREST™ Predictors (RAMSEY), SHIFTS, NUCHEMICS, and QM methods from the predicted structures; and determining one or more specific isotopic labeling positions on each of the polynucleotide sample(s) such that the chemical shift dispersion is maximized and the number of samples is minimized. The MC-Fold|MC-Sym pipeline is a web-hosted service for RNA secondary and tertiary structure prediction. The pipeline means that the input sequence to MC-Fold outputs secondary structures that are directly inputted to MC-Sym, which outputs tertiary structures. See generally, Parisien, M. and Major, F. *Nature* 2008, 452(7183):51-55, which is incorporated herein by reference in its entirety.

In some aspects, the present invention provides a NMR device that is small enough to sit on top of a standard laboratory bench. In some embodiments of the second aspect, the NMR device includes a housing; a sample handling device operable to receive a sample comprising a polynucleotide; and an NMR module. The NMR module may include a sample conduit comprising an analysis volume operable to receive at least a portion of the sample from the sample handling device; a plurality of radiofrequency coils disposed proximately to the analysis volume, each coil operable to generate a distinct excitation frequency pulse across the analysis volume to generate nuclear magnetic resonance of the nuclei of the polynucleotide in the analysis volume; and at least one magnet operable to provide a static magnetic field across the analysis volume and the radiofrequency coils. The NMR module may have a $^1$H Larmor frequency of 300 MHz or less and the RF coils are operable to transmit the excitation frequency pulse to the analysis volume and detect signals from NMR produced by the nuclei of the polynucleotide contained in the analysis volume. Optionally, the device further comprises a heating and cooling device in thermal coupling with the analysis volume. In this regard, the NMR device can employ the use of a sample conduit or analysis volume heating and cooling device for heating the sample containing the biomolecule, for example a protein or a nucleic acid, for example, an RNA polynucleotide to anneal the polynucleotide and bring the polynucleotide into a relaxed or stable conformation prior to acquisition of NMR spectra.

In some embodiments of the NMR device, the NMR module further includes a spectrometer heating or cooling device which maintains the analysis volume at a predetermined temperature during acquisition of NMR spectra. In still a further embodiment, the NMR device also employs a signal processing device, which may include one or more of an analog to digital converter, a signal amplifier, a signal conditioner and combinations thereof.

In another aspect, the present invention provides a method for determining the specific isotopic labeling positions of nucleotides within a polynucleotide sequence for the determination of 3-D atomic resolution structure of a polynucleotide. The method includes providing one or more polynucleotides each polynucleotide having an identical polynucleotide sequence, wherein each of the one or more polynucleotides comprises one or more nucleotides labeled with an isotopic label comprising, $^2$H, $^{13}$C, $^{15}$N, $^{19}$F or $^{31}$P; predicting a plurality of putative structures of the polynucleotide sequence using a computational algorithm; computing one or more predicted NMR chemical shifts for each putative structure; determining a predicted chemical shift overlap for all of the plurality of putative structures; and identifying one or more structural regions of the plurality of putative structures that give rise to a large variation of predicted chemical shifts; determining one or more specific isotopic labeling positions that minimize chemical shift overlap while focusing on the positions with large variation in predicted chemical shifts and maximizing the number of labelings per sample at these positions; determining a plurality of predicted 2-D structures to identify regions of the polynucleotide structure with large variations and designing an optimum labeling scheme that minimizes spectral overlap wherein more than one nucleotide within the polynucleotide sequence is labeled; and using the predicted chemical shift dispersion profiles to provide an optimum labeling scheme that minimizes spectral overlap wherein more than one nucleotide within the polynucleotide sequence is labeled.

In some aspects provided herein are methods, devices, and compositions of matter optionally for use with the method for determining the 2-D or 3-D atomic resolution structure of a polynucleotide. In these aspects, the method includes providing a polynucleotide sample comprising a polynucleotide, the polynucleotide comprising at least one nucleotide isotopically labeled with one or more atomic labels comprising $^2$H, $^{13}$C, $^{15}$N, $^{19}$F and $^{31}$P; admixing with the polynucleotide sample one or more additional molecules comprising one or more of: a small molecule, a protein, a nucleic acid, an ion, and a salt, and an atom; obtaining a NMR spectrum of the polynucleotide sample using a NMR device; determining a chemical shift of the one or more atomic labels; and determining a 2-D or a 3-D atomic resolution structure of the polynucleotide from the chemical shifts determined in step (c).

In some embodiments, the step of determining a 2-D or a 3-D atomic resolution structure of the polynucleotide also includes repeating steps (a)-(c) using a plurality of polynucleotides, wherein each polynucleotide has the identical nucleotide sequence as the polynucleotide used above, and each polynucleotide synthesized with a different nucleotide labeled with the one or more atomic labels. In some embodiments, the nucleotides with one or more atomic labels are nucleotides having a predicted or an experimentally determined structural heterogeneous region. In some embodiments, at least one of the plurality of polynucleotides consists of one isotopically labeled purine nucleotide and one isotopically labeled pyrimidine nucleotide.

In certain embodiments, the method step of providing the polynucleotide sample includes determining one or more 2-D or 3-D models of the polynucleotide sequence using a 2-D or 3-D structure predicting algorithm, respectively; identifying one or more structural heterogeneous regions on each of the one or more 2-D or 3-D models of the polynucleotide sequence; calculating one or more chemical shifts from the one or more structural heterogeneous regions; and synthesizing a polynucleotide comprising one or more nucleotides having one or more atomic labels positioned at one or more nuclei which results in a polynucleotide having a minimized chemical shift overlap.

In some embodiments, the step of obtaining a NMR spectrum of the polynucleotide sample includes interrogating the polynucleotide sample with a NMR spectrometer frequency ranging from about 1 GHz MHz to about 20 MHz. In some embodiments, each polynucleotide in the polynucleotide sample is labeled at the same nucleotide with one or more isotopic labels comprising $^2$H, $^{13}$C, $^{15}$N, $^{19}$F or $^{31}$P for internal referencing.

In some embodiments, determining the 3-D atomic resolution structure includes generating a plurality of theoretical structural polynucleotide 2-D models using the nucleotide sequence and one or more 2-D structure predicting algorithms; generating a plurality of theoretical structural polynucleotide 3-D models using a 3-D structure predicting algorithm using the plurality of theoretical structural polynucleotide 2-D models and optionally one or more known or assumed polynucleotide 2-D model; generating a predicted chemical shift set for each of the plurality of theoretical structural polynucleotide 3-D models; comparing the predicted chemical shift set to the chemical shift(s) of the one or more atomic labels; and selecting one or more theoretical structural polynucleotide 3-D model having an agreement (e.g., the best agreement) between the respective predicted chemical shift set and the chemical shift(s) of the one or more atomic labels as the one or more 3-D atomic resolution structures.

In some embodiments, the predicted chemical shift set is generated by comparing each theoretical structural polynucleotide 3-D model with a NMR-data polynucleotide structure database.

In some embodiments, generating the predicted chemical shift set includes calculating a polynucleotide structural metric comprising atomic coordinates, stacking interactions, magnetic susceptibility, electromagnetic fields, or dihedral angles from one or more experimentally determined polynucleotide 3-D structures; generating a set of mathematical functions or objects that describe relationships between experimental chemical shifts and the polynucleotide structural metric of the experimentally determined 3-D polynucleotide structures using a regression algorithm; calculating a polynucleotide structural metric for each of the theoretical structural polynucleotide 3-D models; and inputting the polynucleotide structural metric for each of the theoretical structural polynucleotide 3-D models into the set of mathematical functions or objects to generate the predicted chemical shift set.

In some embodiments, the regression algorithm is machine learning algorithm comprising a Random Forest algorithm. In some embodiments, determining the experimental chemical shift set comprises modeling the chemical shift set using a NMR spectrometer frequency from about 1 GHz to about 20 MHz.

In some embodiments, determining the 3-D atomic resolution structure includes generating a plurality of theoretical structural polynucleotide 2-D models using the nucleotide sequence and one or more 2-D structure predicting algorithms; generating a plurality of theoretical structural polynucleotide 3-D models using a 3-D structure predicting algorithm using the plurality of theoretical structural polynucleotide 2-D models and optionally one or more known or assumed polynucleotide 2-D model; generating a predicted chemical shift set for each of the plurality of theoretical structural polynucleotide 3-D models; comparing the predicted chemical shift set to the chemical shift(s) of the one or more atomic labels; and selecting one or more theoretical structural polynucleotide 3-D model having an agreement (e.g., the best agreement) between the respective predicted chemical shift set and the chemical shift(s) of the one or more atomic labels as the one or more 3-D atomic resolution structures.

In some embodiments, the method also includes the step of identifying a binding pocket in the one or more 3-D atomic resolution structures. In some embodiments, the method also includes the step of associating the another molecule with the identified binding pocket of each of the one or more 3-D atomic resolution structures. In some embodiments, the method also includes the step of refining the associated another molecule and binding pocket of each of the one or more 3-D atomic resolution structures using a modeling software that performs one or more functions comprising energy minimization and/or a molecular dynamics simulation. In some embodiments, the method also includes the step of identifying a binding pocket in the one or more refined 3-D atomic resolution structures. In some embodiments, the method also includes the step of using one or more coordinates of the another molecule in the refined associated another molecule and binding pocket of each of the one or more 3-D atomic resolution structures. In some embodiments, the predicted chemical shift set is generated by comparing each theoretical structural polynucleotide 3-D model with a NMR-data polynucleotide structure database.

In some embodiments, generating the predicted chemical shift set includes calculating a polynucleotide structural metric comprising atomic coordinates, stacking interactions, magnetic susceptibility, electromagnetic fields, or dihedral angles from one or more experimentally determined polynucleotide 3-D structures; generating a set of mathematical functions or objects that describe relationships between experimental chemical shifts and the polynucleotide structural metric of the experimentally determined 3-D polynucleotide structures using a regression algorithm; calculating a polynucleotide structural metric for each of the theoretical structural polynucleotide 3-D models; and inputting the polynucleotide structural metric for each of the theoretical structural polynucleotide 3-D models into the set of mathematical functions or objects to generate the predicted chemical shift set.

In some embodiments, the regression algorithm is machine learning algorithm that includes a Random Forest algorithm. In some embodiments, determining the experimental chemical shift set includes modeling the chemical shift set using a NMR spectrometer frequency from about 1 GHz MHz to about 20 MHz.

In some aspects provided herein are methods, devices, and compositions of matter optionally for use with the method for determining the structure of a polynucleotide bound to another molecule. In these aspects, the method includes providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2H$, $^{13}C$, $^{15}N$, $^{19}F$ and $^{31}P$; admixing the polynucleotide sample with the another molecule forming a plurality of bound complexes; obtaining a NMR spectrum of the bound complexes using a NMR device; determining a chemical shift of the one or more atomic labels; and determining the 3-D atomic resolution structure of the polynucleotides from the chemical shifts determined in step (d).

In some embodiments, the number of distinctly labeled polynucleotides synthesized in the polynucleotide sample is equal to the number of nucleotides in the polynucleotide, wherein each synthesized polynucleotide has a different nucleotide labeled with the one or more atomic labels. In some embodiments, the nucleotides with one or more atomic labels are nucleotides having a predicted or an experimentally determined structural heterogeneous region. In some embodiments, the at least one nucleotide labeled consists of a labeled purine nucleotide and a labeled pyrimidine nucleotide.

In some embodiments, providing the polynucleotide sample includes determining one or more 2-D or 3-D models of the polynucleotide sequence using a 2-D or 3-D structure predicting algorithm, respectively; identifying one or more structural heterogeneous regions on each of the one or more 2-D or 3-D models of the polynucleotide sequence; calculating one or more chemical shifts from the one or more structural heterogeneous regions; and synthesizing a polynucleotide comprising one or more nucleotides having one or more atomic labels positioned at one or more nuclei which results in a polynucleotide having a minimized chemical shift overlap.

In some embodiments, obtaining a NMR spectrum of the bound complexes includes interrogating the bound complexes with a NMR spectrometer frequency ranging from about 1 GHz MHz to about 20 MHz. In some embodiments, each polynucleotide in the polynucleotide sample is labeled at the same nucleotide with one or more isotopic labels comprising $^2H$, $^{13}C$, $^{15}N$, $^{19}F$ or $^{31}P$ for internal referencing.

In some embodiments, determining the 3-D atomic resolution structure includes generating a plurality of theoretical structural polynucleotide 2-D models using the nucleotide sequence and one or more 2-D structure predicting algorithms; generating a plurality of theoretical structural polynucleotide 3-D models using a 3-D structure predicting algorithm using the plurality of theoretical structural polynucleotide 2-D models and optionally one or more known and/or assumed polynucleotide 2-D models; generating a predicted chemical shift set for each of the plurality of theoretical structural polynucleotide 3-D models; comparing the predicted chemical shift set to the chemical shift(s) of the one or more atomic labels; and selecting one or more theoretical structural polynucleotide 3-D model having an agreement (e.g., the best agreement) between the respective predicted chemical shift set and the chemical shift(s) of the one or more atomic labels as the one or more 3-D atomic resolution structures.

In some embodiments the method also includes the step of identifying a binding pocket in the one or more 3-D atomic resolution structures. In some embodiments the method also includes the step of associating the another molecule with the identified binding pocket of each of the one or more 3-D atomic resolution structures. In some embodiments the method also includes the step of refining the associated another molecule and binding pocket of each of the one or more 3-D atomic resolution structures using a modeling software that performs one or more functions comprising energy minimization and/or a molecular dynamics simulation. In some embodiments the method also includes the step of identifying a binding pocket in the one or more refined 3-D atomic resolution structures. In some embodiments the method also includes the step of using one or more coordinates of the another molecule in the refined associated another molecule and binding pocket of each of the one or more 3-D atomic resolution structures. In some embodiments, the predicted chemical shift set is generated by comparing each theoretical structural polynucleotide 3-D model with a NMR data-structure database.

In some embodiments, generating the predicted chemical shift set includes calculating a polynucleotide structural metric comprising atomic coordinates, stacking interactions, magnetic susceptibility, electromagnetic fields, or dihedral angles from one or more experimentally determined polynucleotide 3-D structures; using a regression algorithm to generate a set of mathematical functions or objects that describe relationships between experimental chemical shifts and the polynucleotide structural metric of the experimentally determined 3-D polynucleotide structures; calculating a polynucleotide structural metric for each of the theoretical structural polynucleotide 3-D models; inputting the polynucleotide structural metric for each of the theoretical structural polynucleotide 3-D models into the set of mathematical functions or objects to generate the predicted chemical shift set.

In some embodiments, the regression algorithm is machine learning algorithm including a Random Forest algorithm.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

(FIG. 11A) RMSD vs. wMAE for all 10,000 models (gray) and top 10 selected models (blue). (FIG. 11B) Overlay of 1YRJ (grey) and refined chemical shift solved structure (blue); binding pocket of refined structure show in gray. (FIG. 11C) ROC plot confirms apramycin pocket enriches A-site binders.

(FIG. 12A) Overlay of free and bound C6-H6/C8-H8 spectra for miR-122 on addition of compounds A and B. Green arrows and labels indicate perturbed resonances. (FIG. 12B) pre-mir122 loop 2° structure (SEQ ID NO: 2). Green residues are perturbed in the titrations.

FIG. 13A-13C show exemplary pre-miR-122 data. (FIG. 13A) pre-miR-122 full length and loop construct (box) (SEQ ID NO: 4). Dicer cleavage points indicated with black arrows. (FIG. 13B) Overlay of C8H8/C6H6 NMR spectra of miR122L on NC1404 titration, NC1404 binding pocket, and $K_d$ plot. (FIG. 13C) Overlay of C8H8/C6H16 NMR spectra of miR122L on NC1444 titration, NC1444 binding pocket, and $K_d$ plot. Arrows and labels in (FIG. 13B) and (FIG. 13C) indicate perturbed resonances.

DETAILED DESCRIPTION

Figure 1:
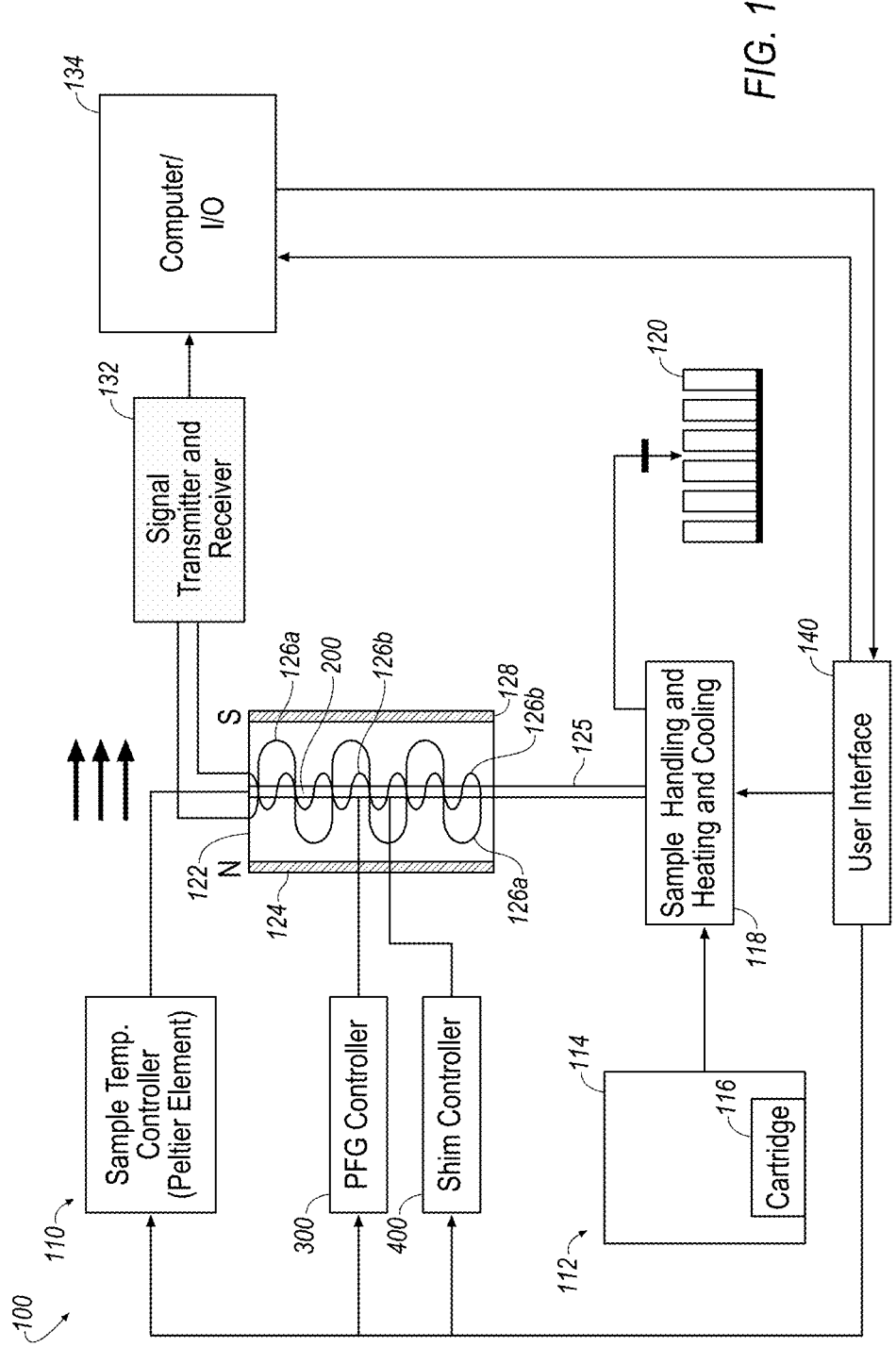
FIG. 1 shows an exemplary schematic representation of the various components of the NMR device in accordance with the several embodiments of the present disclosure.

Unless otherwise defined, all technical terms used herein have the same meaning as commonly understood by one of ordinary skill in the art to which the invention belongs. As used in the specification and the appended claims, the singular forms "a," "an," and "the" include plural references unless the context clearly dictates otherwise. Any reference to "or" herein is intended to encompass "and/or" unless otherwise stated.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9.

Although the open-ended term "comprising," as a synonym of terms such as including, containing, or having, is use herein to describe and claim the present invention, the invention, or embodiments thereof, may alternatively be described using more limiting terms such as "consisting of" or "consisting essentially of" the recited ingredients.

The terminology used herein is for the purpose of describing particular example embodiments only and is not intended to be limiting. As used herein, the singular forms "a", "an" and "the" may be intended to include the plural forms as well, unless the context clearly indicates otherwise.

Thus, for example, reference to "a ligand" includes mixtures of ligands; reference to "an NMR resonance" includes more than one resonance, and the like. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

As used herein, the term "biomolecule" refers to any organic molecule that is part of or from a living organism. Biomolecules can include nucleic acids, a nucleotide, a polynucleotide, an oligonucleotide, a peptide, a protein, a ligand, a receptor, among others.

As used herein, the term "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

As used herein, the term "protein" as used herein, refers to a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

As used herein, the term "sequence" refers to the particular ordering of monomers within a biomolecule and it may be referred to herein as the sequence of the biomolecule.

As used herein, the term "polynucleotide" or "nucleic acid" as used herein refer to any polyribonucleotide or polydeoxribonucleotide polymer comprising nucleotides of any length, and are made up of ribonucleotides or deoxyribonucleotides, that comprise purine or pyrimidine nucleobases, sugars and covalent internucleoside (backbone) linkages or other natural, chemically, or biochemically modified, or non-naturally or derivatized nucleotide bases. Thus, the term "polynucleotide" as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions and may include modified nucleotides. The terms "nucleic acid," "nucleic acid sequence," or "oligonucleotide" also encompass a polynucleotide as defined above. In some embodiments, a polynucleotide is a short interfering RNA (siRNA), a microRNA (miRNA), a plasmid DNA (pDNA), a short hairpin RNA (shRNA), messenger RNA (mRNA), antisense RNA (asRNA), to name a few, and encompasses both the nucleotide sequence and any structural embodiments thereof, such as single stranded, double stranded, triple stranded, helical, hairpin, etc.

A 'modified polynucleotide" in some embodiments, can include a polynucleotide containing one or more modified nucleotides. A modified nucleotide can include a nucleotide which comprises an altered base and/or altered sugar and/or altered internucleotide linkage but which can still incorporate into a nucleic acid molecule via an internucleotide linkage and form Watson Crick bonds with another nucleotide. In some illustrative examples, modified nucleotides can include, methylated cytosine (5-methylcytosine), adenine methylation, 5-hydroxymethylcytosine, glycosylation of uracil, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Modified nucleotides can also include nucleotides with bases such as inosine, queuosine, xanthine, sugars such as 2'-methyl ribose, non-natural phosphodiester internucleotide linkages such as methylphosphonates, phosphorothioates and peptides. In some embodiments, the pentafuronosyl ring may be replaced with acyclic derivatives lacking the C2'-C3'-bond of the pentafuronosyl ring. For example, acyclonucleotides may substitute a 2-hydroxyethoxymethyl group for-the 2'-deoxyribofuranosyl sugar normally present in dNMPs. The nucleoside subunits of the nucleic acid disclosed herein may be linked to each other by phosphodiester bond. The phosphodiester bond may be optionally substituted with other linkages. For example, phosphorothioate, thiophosphate-D-ribose entities, triester, thioate, 2'-5' bridged backbone (may also be referred to as 5'-2'), PACE, 3'-(or -5') deoxy-3'-(or -5')thio-phosphorothioate, phosphorodithioate, phosphoroselenates, 3'-(or -5')deoxy phosphinates, borano phosphates, 3'-(or -5')deoxy-3'-(or 5'-)amino phosphorami-dates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and nonphosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages. In some embodiments, modified polynucleotides can include polynucleotides having a peptide nucleic acid (PNA) backbone. The PNA backbone can include repeating N-(2-aminoethyl)-glycine units linked by peptide bonds. The various bases such as purine, pyrimidine, natural and synthetic bases are linked to the backbone by methylene carbonyl bonds.

In some embodiments, altered inter nucleotide linkages can include modifications made at terminal phosphate groups. Non-limiting examples of different stabilization chemistries can be used, e.g., to stabilize the 3'-end of nucleic acid sequences, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to unmodified backbone chemistries, polynucleotides of the present invention can include conventional backbone chemistries combined with one or more different backbone modifications described herein. The nucleoside subunits of the nucleic acid disclosed herein may be linked to each other by phosphodiester bond. The phosphodiester bond may be optionally substituted with other linkages. For example, phosphorothioate, thiophosphate-D-ribose entities, triester, thioate, 2'-5' bridged backbone (may also be referred to as 5'-2'), PACE, 3'-(or -5')deoxy-3'-(or -5')thio-phosphorothioate, phosphorodithioate, phosphoroselenates, 3'-(or -5')deoxy phosphinates, borano phosphates, 3'-(or -5')deoxy-3'-(or 5'-)amino phosphoramidates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and non-phosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyluridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any 0- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. Sugar moieties can be modified such as, 2'-deoxypentofuranosyl sugar moiety, D-ribose, hexose, modification at the 2' position of the pentofuranosyl sugar moiety such as 2'-O-alkyl (including 2'-O-methyl and 2'-O-ethyl), i.e., 2'-alkoxy, 2'-amino, 2'-O-allyl, 2'-S-alkyl, 2'-halogen (including 2'-fluoro, chloro, and bromo), 2'-methoxyethoxy, 2'-O-methoxyethyl, 2'-O-2-methoxyethyl, 2'-allyloxy ($-OCH_2CH=CH_2$), 2'-propargyl, 2'-propyl, ethynyl, propenyl, CF, cyano, imidazole, carboxylate, thioate, $C_1$ to $C_{10}$ lower alkyl, substituted lower alkyl, alkaryl or aralkyl, OCF$_3$, OCN, O-, S-, or N-alkyl; O-, S, or N-alkenyl; SOCH$_3$; SO$_2$CH$_3$; ONO$_2$; NO$_2$, N3; heterozycloalkyl; heterozycloalkaryl; aminoalkylamino; polyalkylamino or substituted silyl, as, among others.

As used herein, the term "target effector molecule" describes a molecule that can be selected from any biological molecule which is activated or inhibited by ligand binding to a recognition domain on the molecule. Target effector molecules encompassed by the present technology can include a diverse array of compounds including proteins, polypeptides, oligopeptides, polysaccharides and nucleic acids, including RNA and DNA. Exemplary proteins can include enzymes, transmembrane transporters, signal receptors and mediators, primary and secondary messengers, transcription and translation factors, and others. In a preferred method for practicing the technology isotopically labeled molecules are used for the target effector molecule, and substitute for the naturally occurring target effector molecule.

As used herein, the term "ligand" describes any naturally occurring or synthetic compound, or fragment thereof, that binds to the recognition domain of a target effector molecule. In some embodiments, the ligand can be a small organic molecule. Some of these small molecules are part of a larger collection of molecules found in combinatorial libraries. Ligands of the present technology also include members of combinatorial libraries of natural or synthetic small molecules, wherein the libraries contain tens, hundreds, thousands, hundreds of thousands, and millions of variant species. Recognition domains include both primary binding domains and regulatory domains. Ligands can thus be analogs of known substrates or inhibitors or regulators of biological activity. They can also be compounds with no previously identified biological effect. Inhibitor analogs, substrate analogs and regulator analogs can be covalently linked to one another or to any class of ligand to enhance activity by the process of this invention. Binding between ligand and target effector molecule can be any form that causes the desired activation or inhibition, and includes ionic bonding, hydrogen bonding, and Van der Waals association.

As used herein, the "recognition domain" of a target effector molecule describes the local site of the target effector molecule to which a ligand binds and promotes modification of the target effector molecule's biological activity. This modification can be described as agonist activity or antagonist activity, depending on the circumstances of a particular ligand binding event.

As used herein, "magnetic," "magnetic effect," and "magnetism" refer to the phenomena by which one material exert an attractive or repulsive force on another material. Although theoretically all materials are influenced to one degree or another by magnetic effect, those skilled in the art understand that magnetic effect or magnetism is only recognized for its detectability under the specific circumstance.

As used herein, a "permanent magnet" is a material that has a magnetic field without relying upon outside influences. Due to their unpaired electron spins, some metals are magnetic when found in their natural states, as ores. These include iron ore (magnetite or lodestone), cobalt, and nickel. A "paramagnetic material" refers to a material that attracts and repels like normal magnets when subject to a magnetic field. Paramagnetic materials include aluminum, barium, platinum, and magnesium. A "ferromagnetic material" is a material that can exhibit a spontaneous magnetization. Ferromagnetism is one of the strongest forms of magnetism and is the basis for all permanent magnets. Ferromagnetic materials include iron, nickel, and cobalt. A "superparamagnetic material" is a magnetic material that exhibits a behavior similar to that of a paramagnetic material at temperatures below the Curie or the Neel temperature.

An "electromagnet" is a type of magnet in which the magnetic field is produced by a flow of electric current. The magnetic field disappears when the current ceases. A simple type of electromagnet is a coiled piece of wire that is electrically connected. An advantage of an electromagnet is that the magnetic field can be rapidly manipulated over a wide range by controlling the electric current. In the embodiments of the invention, ferromagnetic or non-magnetic materials are used to form the electromagnets.

The term "microprocessor" generally relates to a processor on an integrated circuit (IC) chip. The processor may be one or more processor on one or more IC chip. The chip is typically a silicon chip with thousands of electronic components that serves as a central processing unit (CPU) of a computer or a computing device. A computer of the present invention may contain one or more microprocessors useful in the calculation of Fast Fourier Transforms, chemical shifts, various constraints using chemical shift data and other NMR data, for example, NOE, RDC, J-couplings, and residual chemical shift anisotropy RCSA's and their use in the determination of calculated structures of various biomolecules.

The term "analysis volume" refers to the internal volume space within a sample conduit that is actively interrogated in the NMR device, and more specifically, is the volume space that typically will hold the sample between the magnet and various RF coils which is used during the NMR interrogation to produce NMR of a selected biomolecule that is delivered to the analysis volume.

The term "polynucleotide sample" includes a polynucleotide or a certain quantity (e.g., a number of moles or a concentration of polynucleotide) of the polynucleotide, optionally dissolved in a solvent, wherein the polynucleotides in the polynucleotide sample has one singular nucleotide sequence. In some examples, the polynucleotides in the polynucleotide sample may only have the same nucleotide labeled with the one or more atomic labels, or the polynucleotide sample can consist of polynucleotides synthesized with different nucleotides labeled with one or more atomic labels.

As used herein a nucleic acid or polynucleotide can include DNA, RNA, and mimetic of DNA and RNA and DNA and RNA sequences comprising one or more modified nucleobases or nucleotides. In some embodiments, the DNA can be single or double stranded, genomic DNA, cDNA and variations thereof. In some embodiments, the RNA can include single or double stranded RNA, mRNA, mitochondrial RNA ribosomal RNA and variations thereof. Generally speaking, the term "nucleic acid" can encompasses polynucleotides, oligonucleotides, probes, modified polynucleotides, and so on. Typically, these nucleic acid constructs useful in the methods of the present invention can comprise from about 3 to about 500 base pairs or nucleotides (nt), preferably from about 5 to about 200 base pairs or nucleotides, more preferably from about 6 to about 100 base pairs or nucleotides. While the present methods, device and systems apply equally to DNA nucleic acids as it does to RNA nucleic acids, the methods exemplified and illustrated herein are described with RNA nucleic acids.

As used herein, the term "NMR interaction(s)" refer to all isotropic and anisotropic NMR measurements including but not limited to chemical shifts, J couplings, dipolar couplings, and paramagnetic interactions.

Ribonucleic acid or RNA is a complex biomolecule made from ribonucleotide building blocks. A ribonucleotide comprises a nucleobase, a 5 carbon ribose sugar and one phosphate group. RNA contains four building blocks, these include: adenylate, guanylate, cytidylate and uridylate. These four RNA nucleotides contain the four RNA nucleosides adenosine, guanosine, cytidine and uridine respectively. RNA transcripts can be found in many cellular forms, including: messenger RNA (mRNA), transfer RNA (tRNA), ribosomal RNA (rRNA), micro RNAs (miRNAs), small interfering RNAs (siRNAs), and mitochondrial RNA. In cells, various RNA molecules play critical roles, for example, they control gene expression, sense and communicate responses to cellular signals, catalyze biological reactions, among many others.

There has been an intense effort to decipher the structure, function, and regulatory networks of the human genome. After sequencing the human genome, scientists have undertaken an immense task of identifying the information present in the genome and in particular, to identify and characterize the functional DNA sequences that are implicated in disease and genetic diversity. The project termed Encyclopedia of DNA Elements (ENCODE) has enlisted 32 groups around the world to identify regions of the human genome that are responsible for gene regulation. One of the valuable contributions of the ENCODE project will be to help make sense of Genome Wide Association Studies (GWAS). Several well documented GWAS studies have shown that specific genetic mutations are linked with disease risk. However, until the ENCODE project, many of these mutations were found in non-protein coding DNA regions (90%) leaving the researchers guessing as to how the mutations can be counteracted or what might cause the disease. The ENCODE project has revealed that many of the disease-linked regions of the genome include enhancers and other functional sequences and scientists are now beginning to understand the role of these enhancers and functional sequences in disease, causation and promotion. Some of these important "non-coding" regions are ultimately transcribed into RNA, some of which are now known to be important regulators of gene expression. This regulation often occurs through structural elements that affect recognition by specific RNA binding proteins.

However, the predominant source of cells used to gather results in the ENCODE project have come from a very few select number of cell lines. There are literally thousands of additional cell types that will need to be interrogated and orders of magnitude higher genetic sequences, particularly RNA that will need to be examined once their significance in gene expression regulation has been determined. As yet, there are very few techniques to rapidly and sensitively map the topography of RNA structures for determination of function in gene regulation. The lag in RNA structure characterization techniques will further retard the discovery process that will lead to the understanding of RNA function and its regulatory elements impacting gene expression across the entire genome.

Protein-nucleic acid interactions are involved in many cellular functions, including transcription, RNA splicing, mRNA decay, and mRNA translation. Readily accessible synthetic molecules that can bind with high affinity to specific sequences of single- or double-stranded nucleic acids have the potential to interfere with these interactions in a controllable way, making them attractive tools for molecular biology and medicine. Successful approaches for blocking function of target nucleic acids include the use of duplex-forming antisense oligonucleotides or chemically modified oligonucleotide-like derivatives. In addition to specific RNA structures, the accessibility of different regions of the RNA was recently shown to be important in several processes such as the ability of microRNAs to bind their targets, control of translation speed and control of translation initiation. Gaining knowledge and an appreciation of the RNA structure in three dimensions may also be critical for the development and understanding of RNA-based molecules which may find great utility in a wide range of biotechnological applications, including rational design of biological and molecular sensors that may be useful in the treatment and monitoring of disease. Some of these applications may also provide a greater understanding of the interrelationship between nucleic acid structure and the effects of pH, analytes and proteins.

Nuclear Magnetic Resonance (NMR) spectroscopy is a powerful analytical technique used to determine qualitative and quantitative information about organic molecules. NMR has been used to solve and provide valuable information about the structure of a variety of chemical and biological molecules, ranging from small organic compounds to complex polymers such as proteins and nucleic acids. In NMR, a sample is placed in a magnetic field and is subjected to radiofrequency (RF) excitation at a characteristic frequency called Larmor frequency (f):

$$f = \frac{\gamma}{2\pi} B_0$$

where $\gamma$ is the gyromagnetic ratio of nuclei and $B_0$ is the magnetic field strength. The nuclei in the magnetic field absorb the energy provided and become energized. The frequency of the radiation necessary for absorption depends on the type of nuclei to be excited, (e.g., $^1H$ or $^{13}C$, or $^{15}N$), the frequency will typically also depend on the chemical environment of the nucleus (e.g., the presence of various chemical electronegative groups, salts, pH of solution, and the presence of binding agents), and lastly, the frequency may also depend on the spatial location in the magnetic field if the magnetic field is not uniform, i.e., the field is not homogeneous.

The use of chemical shifts as a new abundant source of structure and dynamics information is arguably more important for nucleic acid structure determination as compared to proteins. NMR structure determination of nucleic acids traditionally suffers from a shortage of accessible interproton NOE-derived distance constraints that can be applied towards structure characterization. This problem is compounded by a high degree of flexibility, particularly in RNA, which can complicate the interpretation of NOE-derived distance constraints.

An inherent obstacle in NMR structure characterization of biomolecules is the relatively poor sensitivity of the NMR procedure. The NMR signal-to-noise (S/N) ratio of biomolecules is impacted by the relatively low abundance of $^{15}N$ (0.365%) and $^{13}C$ (1.108%) and their gyromagnetic ratios (6.73 and −2.71 ($10^7$ rad s$^{-1}$ T$^{-1}$) for $^{13}C$ and $^{15}N$, respectively) being markedly lower than that of protons (26.75 ($10^7$ rad s$^{-1}$ T$^{-1}$)). The S/N can be approximated by the equation:

$$S/N \propto n\gamma_e \sqrt{\gamma_d^3 B_0^3 t}$$

where n is the number of nuclear spins being observed, $\gamma_e$ is the gyromagnetic ratio of the spin being excited, $\gamma_d$ is the gyromagnetic ratio of the spin being detected, $B_0$ is the magnetic field strength, and t is the experiment acquisition time. Other factors that are involved in S/N are the probe filling factor (e.g., the fraction of the coil detection volume filled with sample), and various other probe and receiver factors that are typically approximately equivalent for equipment built in the same period of time. It is obvious to users that the highest field instrument available provides the best sensitivity. For fixed t, 20.5 times as much material with a 100 MHz NMR spectrometer than compared to a 750 MHz spectrometer would be needed to obtain an NMR spectra with identical S/N: N300/N750=[750/100]3/2=20.5. In high resolution (i.e., atomic resolution of approximately 1-5 Å) NMR mapping and structure characterization of biological molecules, such as RNA and DNA, the only feasible way to obtain a sufficiently resolved spectrum using chemical shift data is to increase the applied field (i.e., magnetic field strength and radiofrequency excitation). The NMR experiment consists of multiple cycles of pulsing, detection, and repetition delay. At high magnetic fields (600 MHz and higher), the repetition delay of a few seconds is necessary for typical biomolecules of interest to restore perturbed nuclei magnetization back to initial state for the next cycle. Since pulsing and detection combined is normally 80-150 milli-seconds, most of NMR time is spent on repetition delay.

The ENCODE project data indicates that a simple, high-throughput nucleic acid structure analysis method and device would help to alleviate the pressing need to link RNA structure to cellular function within the plethora of identified and as yet unidentified RNA molecules that may hold the key to resolving the pathogenesis of many important diseases. There remains a long-felt and unmet need to resolve these nucleic acid dynamic conformations as a means to yield structural information which may lead to the rational design of targeted, biologically-active compounds. One of the barriers to rapid dissemination of RNA structure resides in the lack of customizable, relatively inexpensive and high-throughput processes and devices for NMR analysis of RNA molecules. The understanding of three-dimensional structure of RNA and DNA will certainly apply to drug discovery, but still perhaps more significant applications such as identifying effects of nucleic acid mutations on structure and function and downstream gene regulation tantalizingly await.

Method for Studying Biomolecules

In discussion of the various methods of the present invention, the labeling techniques and the analysis of the labeled samples using NMR. In various embodiments, the methods for determining a 2-D structure and/or a 3-D atomic structure utilize NMR devices having a commercially available spectrometer frequencies, for example, at a $^1$H Larmor frequency of greater than about 1 GHz, about 1 GHz, from about 1 GHz MHz to about 20 MHz, or about 900 MHz, about 800 MHz, about 700 MHz, about 600 Mhz, about 500 MHz, about 400 MHz, about 300 MHz, about 200 MHz, about 100 MHz, about 75 MHz, about 50 MHz, or about 20 MHz, can be used to determine the structure of a biomolecule, for example, a polynucleotide. Solely for the purpose of convenience, the disclosure of the present methods will be exemplified with the use of polynucleotides, but the methods described herein are applicable to determine the interactions or structure of a protein or a polypeptide as the target or desired biomolecule of interest. Methods for selectively labeling proteins and polypeptides are known in the art. In some embodiments, the methods of the present technology can be performed using an NMR module operable to provide a $^1$H Larmor frequency of 300 MHz or less.

In some embodiments, a significant advantage of the present invention is the use of lower magnetic fields (for example, 300 MHz or less), which can significantly shorten the repetition delay and the total experimental time can be reduced to ¼-⅕ of that of high fields because the repetition delay depends on Ti relaxation time which is significantly shorter at low magnetic field (i.e., Ti relaxation time at 100 MHz is more than 6 times shorter than that of 600 MHz for molecules of correlation time of 4-8 ns (oligonucleotides of 25-50 bases)). This Ti relaxation time difference at between high and low magnetic fields becomes larger as molecular weight or size of a molecule increases. Within given time, 4-5 times more measurements can be repeated and added at low magnetic fields to yield signal-to-noise gain of factor of 2.

In some embodiments a number of small molecule-bound bimolecular structures can be determined for uses comprising computer aided drug discovery efforts, which commonly rely on biomolecular structures determined when bound to a small molecule. Representative small molecules include aminoglycosides, flavin/flavonoids, intercelators (e.g., acridine orange, proflavine and the like), and tetracylines (e.g., tetracycline, doxycycline and the like). An exemplary set of small molecules that can be used to determine a small molecule-bound biomolecular structure is shown below in Table 1.

TABLE 1

Non-limiting examples of small molecules.

| Name | Name |
|---|---|
| Netilmicin | 9-Aminoacridine |
| Paromomycin | Lincomycin |
| Neomycin B | Kanamycin B |
| Mitoxantrone | Sisomicin |
| 5-(N-N-dimethyl)-amiloride | Thiazole orange |
| Diminazene | Ethidium Bromide |
| Kanamycin A | 4',6-diamidino-2-phenylindole |
| Streptomycin | Quinacridine |
| Gentamicin | Acridine orange |
| Amikacin | Erythromycin |
| Pentamidine | Cycloheximide |
| Hoechst 33258 | Blasticidine S |
| Tobramycin | Chloramphenicol |
| Hoechst 33342 | Spectinomycin |
| Chlortetracycline | Puromycin |
| Minocycline | Acetylpromazine |
| Oxytetrtacycline | Yohimbine |
| Tetracycline | Usnic Acid |
| Doxycycline | Enamine T0503-4982 |
| Riboflavin | Gossypin |
| Proflavine | Quercitrin |
| Apramycin | L-arg-p-nitroanilide |
| Kasugamycin | Rutin |
| Hygromycin B | Chembridge 5484617 |
| Geneticin | Chembridge 5566364 |
| Ribostomycin | Life Chemicals F3246-0011 |
| Amiloride | Enamine 4864450 |
| Spiramycin | Princeton BioResearch OSSK-789168 |
| Tylosin | Maybridge JFD02062 |
| Linezolid | Enamine AR-471/43118679 |

2-(2,3-diamino-3H-benzimidazol-1-yl)-1-(4-methoxyphenyl)ethanone
2-amino-3-hydroxy-N-[(2,3,4-trihydroxyphenyl)methyleneamino]propanamide
4-(2-hydroxyethylamino)-7-methyl-2-oxo-1,5-diazabicyclo[4.4.0]deca-3,5,7,9-tetraene-3-carbaldehyde
3-chloro-2-(2,3,4,5,6-pentahydroxyhexylideneamino)naphthalene-1,4-dione
Smiles: c12c(c(=O)n3c(n2)c(ccc3)C)cc(c(n1Cc1ccccc1)=N)C(=O)NCCN1CCOCC1
5-((3-Aminopropyl)amino)-7,10-dihydroxy-2-(2-((2-hydroxyethyl)amino)ethyl)anthra(1,9-cd)pyrazol-6(2H)-one
[3-(diethylamino)isoindol-1-ylidene]-diethyl-ammonium
1-[6-amino-8-(2-hydroxyethylamino)purin-3-yl]-3-morpholin-4-ylpropan-2-ol In some embodiments, one or more small molecules described herein are salts. In some embodiments, one or more small molecules described herein are not salts but are in free form. In some embodiments, one or more small molecules described herein are complexed with another molecule. In some embodiments, one or more small molecules described herein are mixed and/or in the presence of one or more molecules, atoms, ions, and/or other matter.

In order to identify which small molecules interact with the biomolecule, in some embodiments, one synthesizes a uniformly isotopically labeled biomolecular sample, individually or in a combinatorial manner mix each small molecule at a ratio that one would expect to see changes in NMR signals for relatively tight binding small molecules (for a low μM $K_d$, a ratio of 2:1 or 4:1 could be used), collect the NMR data such as chemical shifts, resonance intensities, and/or NOEs, compare the NMR data of the biomolecule in the presence of the small molecule to the NMR data of the biomolecule in the absence of the small molecule, and select small molecules that cause significant changes in the NMR data. In some embodiments, changes in NMR data comprise a portion of a chemical shift linewidth, for example a one linewidth. In some embodiments, changes in NMR data comprise a significant reduction in an NOE and/or a resonance intensity when comparing the biomolecule NMR data in the absence and presence of the small molecule is significant). In various embodiments, NMR data of the small molecule could be monitored and similar perturbations observed on addition of the biomolecule of interest, where, in some embodiments, the biomolecule is non-isotopically labeled. In various embodiments, the same solution conditions (e.g., buffer or solubilization solution) for each sample are used to minimize random noise due to differences in solution environments.

In some embodiments, the present invention provides a method for determining the 3-D atomic resolution structure of a polynucleotide when bound to a small molecule, ligand or other chemical entity for purposes comprising computer-aided drug design. The method includes providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2H$, $^{13}C$, $^{15}N$, $^{19}F$ and $^{31}P$; generating an NMR sample comprising one or more polynucleotides admixed with one or more small molecules that form one or more bound complexes; obtaining an NMR spectrum of the NMR sample using an NMR device; determining one or more chemical shifts of the one or more atomic labels; and determining the 3-D atomic resolution structure of the polynucleotides from the chemical shifts determined in step (d).

In some embodiments, the present invention provides a method for determining the 3-D atomic resolution binding pocket of a polynucleotide purposes comprising computer-aided drug design. The method includes identifying one or more small molecule binders that bind the polynucleotide; providing a polynucleotide sample comprising a plurality of the polynucleotide, wherein each polynucleotide comprises at least one nucleotide isotopically labeled with one or more atomic labels selected from the group consisting of $^2H$, $^{13}C$, $^{15}N$, $^{19}F$ and $^{31}P$; generating an NMR sample comprising the polynucleotide sample admixed with one or more of the small molecule binders; obtaining an NMR spectrum of the NMR sample using an NMR device; determining one or more chemical shifts of the one or more atomic labels; and determining the 3-D atomic resolution structure of the polynucleotides from the chemical shifts determined in step (d); identifying the binding pocket of the one or more small molecule binders, wherein the binding pocket is identified using methods comprising, computational docking, molecular dynamics, quantum mechanics, and/or any other computer-aided methods useful to determine a small molecule binding pocket.

In some embodiments, the present invention provides a method for determining the 3-D atomic resolution binding pocket of a polynucleotide purposes comprising computer-aided drug design, the method includes identifying one or more small molecule binders that bind the polynucleotide, wherein the one or more small molecule binders are identified from Table 1; providing a polynucleotide sample comprising a plurality of the polynucleotide, wherein each polynucleotide comprises at least one nucleotide isotopically labeled with one or more atomic labels selected from the group consisting of $^2H$, $^{13}C$, $^{15}N$, $^{19}F$ and $^{31}P$; generating an NMR sample comprising the polynucleotide sample admixed with one or more of the small molecule binders; obtaining an NMR spectrum of the NMR sample using an NMR device; determining one or more chemical shifts of the one or more atomic labels; and determining the 3-D atomic resolution structure of the polynucleotides from the chemical shifts determined in step (d); and identifying the binding pocket of the one or more small molecule binders, wherein the binding pocket is identified using methods comprising, computational docking, molecular dynamics, quantum mechanics, and/or any other computer-aided methods useful to determine a small molecule binding pocket.

In some embodiments, one or more small molecules are identified from Table 1. In some embodiments, one or more small molecule binders are not identified from Table 1. In some embodiments one or more small molecule binders are identified using any physical, physiochemical, biophysical, biochemical, and/or biological method.

Figure 2:
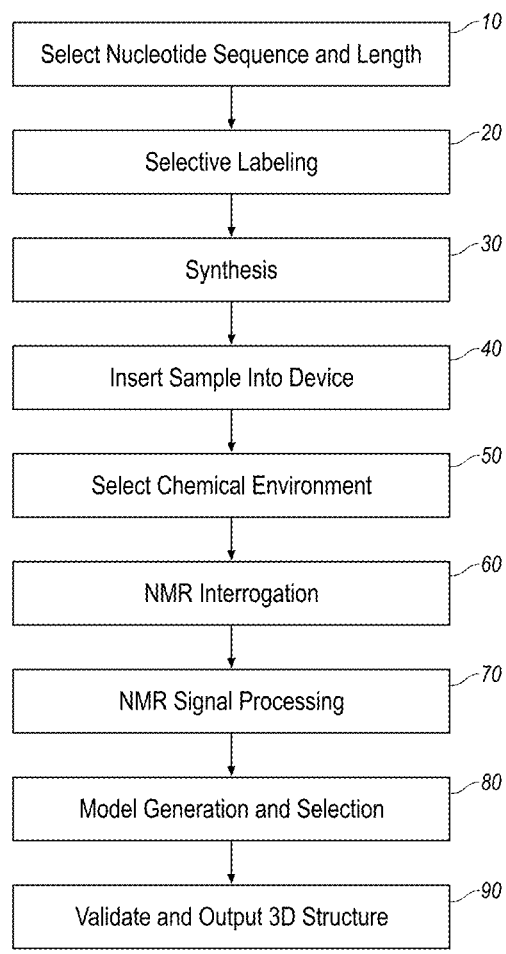
FIG. 2 depicts a bar flowchart of the various exemplary steps used in some embodiments in accordance with the teachings of the present disclosure.

In various embodiments, with reference to FIG. 2 an exemplary method for determining the 3-D structure and biochemical characteristics of a biomolecule, for example a polynucleotide, for example, an RNA polynucleotide when bound to a small molecule ligand comprises: (10) selecting a nucleotide sequence, (20) selectively labeling one or more polynucleotides, (30) synthesizing the one or more labeled polynucleotides, (40) inserting the one or more polynucleotides into the NMR device, (50) selecting a chemical environment of the one or more labeled polynucleotides for the NMR interrogation procedure, which comprises one or more small molecules that have the potential to bind the biomolecule of interest; (60) performing NMR analysis on the one or more labeled polynucleotides using the NMR device of the present invention, (70) process the NMR signals obtained for the one or more labeled polynucleotides, (80) generating one or more 3-D models and performing an analysis to select a 3-D model that best fits the experimental data and the predicted chemical shifts, and (90) validating the selected model with other NMR data and outputting the validated 3-D structure of the polynucleotide in the selected chemical environment. In various embodiments, FIG. 1 has an additional step of identifying one or more small molecule binding pockets.

Methods to Solve Small Molecule-Bound Nucleic Structures and Binding Pockets

1. Preparation of Selectively Labeled Polynucleotides for Structure Characterization The present methods for the determination of structural information of a biomolecule, for example solving a small molecule-bound biomolecule structure and/or binding pocket, in part can be performed using any commercially available NMR spectrometer having a spectrometer or $^1H$ Lamor frequency from about 1 GHz MHz to about 20 MHz. In some embodiments, a commercially available NMR spectrometer has a $^1$H Lamor frequency of greater than 1 GHz, about 1 GHz, about 900 MHz, about 800 MHZ, about 750 MHz, about 700 MHz, about 600 MHz, about 500 MHz, about 400 MHz, about 300 MHz, about 200 MHz, about 100 MHz, or about 50 MHz.

In some embodiments, there are unexpected advantages using a low field NMR device, for example, an NMR device having a spectrometer frequency of 300 MHz or less. In some embodiments, the methods are derived from the surprising finding that low field NMR can be employed to obtain structurally detailed information concerning a complex structure, such as a polynucleotide, if the sample is appropriately labeled with one or more isotopically labeled nucleotides. Combining the use of low field NMR (i.e., a $^1$H Larmor frequency of 300 MHz or less) with selective labeling of the sample provides a sufficient resolution that permits NMR studies of complex 3-D structures using chemical shift information derived from innovative lab-benchtop NMR devices as described herein. Advantages offered by the presently described devices when used in the methods of the present invention can include: (i) Relaxation issues (shortened relaxation delay due to Ti benefit), (ii) improved NMR sensitivity (use of two or more microcoils tuned for different frequencies for mass-sensitivity), and (iii) selective labeling of nucleotides to derive a 3-D structure of the polynucleotide in question from background "noise". The present methods and device also provide customary information or NMR interactions that may be pertinent to the resolution and determination of 3-D atomic resolution structure of a biomolecule under study, such as residual dipolar couplings, nuclear Overhauser effect (NOE) data, measurement of residual chemical shift anisotropies (RCSA) and J-coupling or scalar coupling data.

In various embodiments, the present invention provides a method for determining one or more specific isotopic labeling positions of one or more nucleotides within a polynucleotide sequence for the determination of 3-D atomic resolution structure or collecting other NMR interaction data of a polynucleotide. In some embodiments, the method comprises: (a) providing one or more polynucleotides each of the one or more polynucleotides having an identical polynucleotide sequence, wherein each of the one or more polynucleotides comprises one or more nucleotides labeled with an isotopic label comprising, $^2$H, $^{13}$C, $^{15}$N, $^{19}$F or $^{31}$P; (b) generating a plurality of structures of the polynucleotide sequence using a computational algorithm (e.g., MC-Sym); (c) identifying one or more region(s) on each of the plurality of polynucleotide structures that exhibit a large structural variation using metrics comprising an $S^2$<0.8 and/or RMSF>0.5 Å; (d) calculating a plurality of chemical shifts from regions of the predicted structures having a large structural variation using a chemical shift predictor; such as Nymirum's Random Forest Predictors (RAMSEY), SHIFTS, NUCHEMICS, and QM methods from the predicted structures; and (e) determining one or more specific isotopic labeling positions on each of the polynucleotide sample(s) such that the chemical shift dispersion is maximized and/or the number of samples is minimized.

In some embodiments, prediction of small molecule binding regions inform labeling schemes such that residues and/or atoms that are predicted to interact with the small molecule are isotopically enriched. In some embodiments, predictions are based on biomolecular sequence, predicted secondary structure, a plurality of predicted secondary structures, predicted tertiary structure, and/or a plurality of predicted tertiary models. In some embodiments, predictions are based on a tertiary structure determined, at least in part, using experimental data, and/or a plurality of tertiary structures, one or more determined, at least in part, using experimental data, In various embodiments, knowledge, for example other experimental data, of small molecule binding regions inform labeling schemes such that residues and/or atoms that are predicted to interact with the small molecule are isotopically enriched. In various embodiments, knowledge is derived from binding and/or biochemical experiments. In various embodiments binding experiments comprise NMR experiments, x-ray crystallography experiments, fluorescence experiments, gel migration experiments, and nucleic acid digestion (e.g., SHAPE) experiments.

In some embodiments, the number of isotopically labeled polynucleotides synthesized for the polynucleotide sample is equal to the number of nucleotides in the polynucleotide, wherein each synthesized polynucleotide has a different nucleotide labeled with the one or more atomic labels. In some embodiments, the nucleotides labeled with one or more atomic labels can include nucleotides having a predicted or an experimentally determined structural heterogeneity or a predicted or an experimentally determined structural heterogeneous region. As used herein, a structural heterogeneous region, is defined as: one or more contiguous nucleotides in the polynucleotide sequence in which the polynucleotide 2-D structure of the one or more contiguous nucleotides is any one or more of:

a. known or predicted to participate in labile or unstable base-pairs,
b. exist in non-helical structures such as a bulge, internal loop, apical loop, or any other junction,
c. exist in non-Watson-Crick base-pairs,
d. are known or predicted to have a poorly defined secondary structure,
e. are known or predicted to interact with one or more small molecules, or
f. neighbor any of the polynucleotide structural elements defined in (a-e).

In some embodiments a neighbor of a polynucleotide structural element is one or more nucleotides distant from the structural element, for example +/−1 nucleotide distant, +/−2 nucleotide distant, +/−3 nucleotide distant, +/−4 nucleotide distant, +/−5 nucleotide distant, +/−6 nucleotide distant, +/−7 nucleotide distant, +/−8 nucleotide distant, +/−9 nucleotide distant, +/−10 nucleotide distant.

In some embodiments, a structural heterogeneous region indicative of a large 2-D or 3-D structural hetereogeneity is calculated using various metrics such as $S^2$ order parameters, root mean squared fluctuation (RMSF) etc. In calculation of 2-D structural heterogeneity, a set of putative 2-D structures (e.g., 10 low energy predicted models from MC-Fold) can be used. For each nucleotide in the polynucleotide putative 2-D structure, one or more nucleotides can be identified as a base pair partner(s). In various embodiments, the 2-D structural hetereogeneity then is defined as a real number for each base: [number of unique base pair partner(s)]/[total number of putative 2-D structures], where a larger number indicates a more heterogeneous 2-D structure of the particular nucleotide. In calculation of 3-D structural heterogeneity, a set of putative 3-D structures (e.g., 10 low energy predicted models from MC-Sym) can be used. The chosen structural parameter (e.g., $S^2$ or RMSF) can be calculated based on the putative 3-D structures. In some embodiments the putative structures can be superimposed using a common set of residues/atoms, for example all heavy atoms in the helical region(s) of the RNA of interest, prior to calculating the structural heterogeneity. In another embodiment, the structural heterogeneity metric can then be normalized to the residue with the highest predicted structural fluctuations. Those residues with the highest relative fluctuation can be selected for further investigation of predicted chemical shifts, which for example could be all residues with $S^2<0.8$ and/or RMSF>0.5 Å. The cutoffs used to determine the labels that will be isotopically labeled can vary according to the complexity and/or structural variability of the RNA of interest. The chemical shifts of atoms in the residues selected would be calculated using a chemical shift predictor such as Nymirum's Random Forest Predictors (RAMSEY), SHIFTS, NUCHEMICS, and QM methods and labeling positions on each of the polynucleotide sample(s) selected such that the chemical shift dispersion is maximized and the number of samples is minimized.

In some embodiments, one uses the $S^2$ order parameter, which varies from 1 to 0 for rigid and isotropic motions respectively, is used to determine the residues to isotopically label. In some embodiments, after superimposing the 10 low energy structures from MC-Sym predictions using a common set of residues/atoms, for example all heavy atoms in the helical region(s) of the RNA of interest, the $S^2$ order parameter can be calculated for chosen bonds of interest (e.g., N1H1/N3H3, C1'H1', C5H5, C6H6, C8H8, C2H2 etc.) using the equilibrium expression:

$$S_{eq}^2 = \frac{\langle 1/r^3 \rangle^2}{\langle 1/r^6 \rangle} \left[ \frac{3}{2} (\langle \hat{\mu}_x^2 \rangle^2 + \langle \hat{\mu}_y^2 \rangle^2 + \langle \hat{\mu}_z^2 \rangle^2) + (\langle \hat{\mu}_x \hat{\mu}_y \rangle^2 + \langle \hat{\mu}_z \hat{\mu}_x \rangle^2) - \frac{1}{2} \right]$$

where r is the bond length of the bond of interest, and $\mu_n$ is coordinate component of the bond of interest where n=x, y, or z direction. After calculation of $S^2$, one may select all residues with bonds have $S^2$ less than a cutoff value (e.g., $S^2<0.8$). Alternatively, one could independently normalize the $S^2$ values for each bond vector type such that the $S^2$ of the most flexible residue is 0. Then one could select the residues with the lowest $S^2$ values by selecting an internal cutoff (e.g., $S^2<0.8$). In another embodiment, one could calculate the center of mass for each residue and repeat the $S^2$ calculation using the center of mass rather than individual bond vectors of the residue(s).

In various embodiments, the RMSF, which is always greater than 0, is used to determine a structural heterogeneous region or regions of a polynucleotide with a large structural variation. In some embodiments, after superimposing an exemplary set of 10 low energy structures from MC-Sym predictions using a common set of residues, for example, all heavy atoms in the helical region(s) of the RNA of interest, the RMSF can be calculated for chosen structural parameters of interest using the equation:

$$RMSF = \sqrt{\frac{1}{N} \sum_{i=1}^{N} (j_i - \bar{j}_i)^2}$$

where N is the number of polynucleotide structures under consideration and j is a structural feature such as atomic position, residue center of mass position etc., and $\bar{j}$ denotes the average of the structural feature averaged over the N structures. After calculation of RMSF, one may select all residues with RMSF greater than a cutoff value (e.g., RMSF>0.5 Å).

In some embodiments, to calculate the minimized chemical shift overlap (d), where $d=\min(|\delta_i-\delta_j|)$ where $\delta_i, \delta_j \in \{\delta_{labeled\ positions}^{calculated}\}$, a sampling algorithm such as the Kennard-Stone algorithm (R. W. Kennard, L. A. Stone, Computer aided design of experiments, Technometrics 11 (1969) 137-148, the disclosure of which is incorporated herein by reference in its entirety) can be adopted to rank a list of possible combination of labeling positions on each of the polynucleotide sample. For example, each labeled position (e.g., an atomically labeled nuclei) is considered as a point in the Kennard-Stone algorithm. The algorithm works as follows: first find the two positions most dispersed or largest dispersion (d) in the trial set. For each candidate position, find the smallest dispersion (d) to any position already selected. Select that position for the training set which has the largest of these smallest dispersion. This algorithm always gives the same result, due to the two starting positions which are always the same. The results of the Kennard-Stone algorithm would provide the fewest number of necessary polynucleotides needed to be synthesized while maintaining maximum chemical shift dispersion.

In various embodiments, the Kennard-Stone algorithm is used to select more than one residue to be isotopically labeled that does not maintain maximum chemical shift dispersion, thus affording less spectral resolution, with the goal of reducing the number polynucleotides to be synthesized.

In some embodiments, generation and selection of a structural model step (80) can include the steps of selecting a polynuceotide sequence of interest; predicting 2-D structure using any 2-D structure predicting algorithm, for example, contrafold, Vienna RNA package, centroid-fold, RNAstructure, ContextFold, IPKnot, MC-Fold and the like; generating a 3-D model using any 3-D structure predicting algorithm, for example, MC-Sym, NAB (distance geometry), Rosetta FARFAR, NAST, RNA builder, and the like; determining the minimum energy conformation of the structure using molecular mechanics software, for example, NAB, NAMD, GROMACS, TINKER, CHARMM, AMBER, and the like; and calculating the regions of the RNA that exhibit large structural variation using metrics such as $S^2$ and/or RMSF, where large structural variation is defined as $S^2<0.8$ and/or RMSF>0.5 Å. For regions of the RNA with large structural variations, calculate the chemical shifts from each structure using chemical shift calculation software, for example, Nymirum's Random Forest Predictors (RAMSEY), SHIFTS, NUCHEMICS, and QM methods; using a computational algorithm(s)/software, such as the Kennard-Stone algorithm, select one or more residues that will be isotopically labeled such that the chemical shift dispersion is maximized, or is as maximized as possible, and the number of samples is minimized.

In some embodiments, a structural heterogeneous region of a 3-D polynucleotide structure is defined as: one or more contiguous nucleotides in the polynucleotide sequence in which the polynucleotide 3-D structure of the one or more contiguous nucleotides is any one or more of:
  a. known or predicted to participate in labile or unstable base-pairs,
  b. exist in non-helical structures such as a bulge, internal loop, apical loop, or any other junction,
  c. exist in non-Watson-Crick base-pairs,
  d. exist in a known or predicted small molecule binding pocket,
  e. exist in a known or predicted small molecule interaction, f. are known or predicted to have a poorly defined tertiary structure using metrics such as an $S^2<0.8$, an RMSF>0.5 Å, or a root mean square deviation>2.0 Å, or g. a neighbor any of the polynucleotide structural elements defined in (a-f).

In some embodiments a neighbor of a polynucleotide structural element is one or more nucleotides distant from the structural element, for example +/−1 nucleotide distant, +/−2 nucleotide distant, +/−3 nucleotide distant, +/−4 nucleotide distant, +/−5 nucleotide distant, +/−6 nucleotide distant, +/−7 nucleotide distant, +/−8 nucleotide distant, +/−9 nucleotide distant, +/−10 nucleotide distant.

In some embodiments, an exemplary method for calculating a 2-D structural heterogeneous region can include an illustrative example using a set of putative 2-D structures (e.g., 10 low energy predicted models from MC-Fold). For each nucleotide in the polynucleotide putative 2-D structure, one or more other nucleotides can be identified as a base pair partner(s). The 2-D structural variance then can be defined as a real number for each base: [number of unique base pair partner(s)]/[total number of putative 2-D structures], where a larger number indicates a more heterogeneous 2-D structure of the particular nucleotide.

In another illustrative example of how to calculate 2-D structural heterogeneous region involves the calculation of a 3-D structural heterogeneous region, wherein a set of putative 3-D structures (e.g., 10 low energy predicted models from MC-Sym) is used. The chosen structural parameter (e.g., $S^2$ or RMSF) can be calculated based on the putative 3-D structures. In some embodiments the putative structures are superimposed using a common set of residues/atoms, for example, all heavy atoms in the helical region(s) of the RNA of interest, prior to calculating the structural heterogeneity. In various embodiments, the structural heterogeneity metric is then normalized to the residue with the highest predicted structural fluctuations. Those residues with the highest relative fluctuation can be selected for further investigation of predicted chemical shifts, which for example could be all residues with $S^2<0.8$ and/or RMSF>0.5 Å. In some embodiments, the cutoffs used to determine the labels that will be isotopically labeled vary according to the complexity and/or structural variability of the RNA of interest.

In some embodiments, a large structural heterogeneous region in tertiary structure is calculated using various metrics such as $S^2$ order parameters and/or root mean squared fluctuation (RMSF) etc. In some embodiments, the calculation of structural heterogeneity includes a set of putative structures (e.g., 10 low energy predicted models from MC-Sym). The chosen structural parameter is, in some embodiments, calculated based on the set of putative structures. In some embodiments the putative structures are superimposed using a common set of residues/atoms, for example all heavy atoms in the helical region(s) of the RNA of interest, prior to calculating the structural heterogeneous region. In another embodiment, the structural heterogeneity metric is normalized to the residue with the highest predicted structural fluctuations. Those residues with the highest relative fluctuation are then selected for further investigation of predicted chemical shifts, which for example could be all residues with $S^2<0.8$ and/or RMSF>0.5 Å. The cutoffs used to determine the labels that will be isotopically labeled can vary according to the complexity and/or structural variability of the RNA of interest. The chemical shifts of atoms in the residues selected would be calculated using a chemical shift predictor such as Nymirum's Random Forest Predictors, SHIFTS, NUCHEMICS, and QM methods and labeling positions on each of the polynucleotide sample(s) selected such that the chemical shift dispersion is maximized and the number of samples is minimized.

In some embodiments, one uses the $S^2$ order parameter, which varies from 1 to 0 for rigid and isotropic motions respectively, to determine the residues to isotopically label. After superimposing the 10 low energy structures from MC-Sym predictions using a common set of residues/atoms, for example, all heavy atoms in the helical region(s) of the RNA of interest, the $S^2$ order parameter can be calculated for chosen bonds of interest (e.g., N1H1/N3H3, C1'H1', C5H5, C6H6, C8H8, C2H2 etc.) using the equilibrium expression:

$$S_{eq}^2 = \frac{\langle 1/r^3 \rangle^2}{\langle 1/r^6 \rangle}\left[\frac{3}{2}(\langle \hat{\mu}_x^2 \rangle^2 + \langle \hat{\mu}_y^2 \rangle^2 + \langle \hat{\mu}_z^2 \rangle^2) + (\langle \hat{\mu}_x \hat{\mu}_y \rangle^2 + \langle \hat{\mu}_z \hat{\mu}_x \rangle^2) - \frac{1}{2}\right]$$

where r is the bond length of the bond of interest, and ti n is coordinate component of the bond of interest where n=x, y, or z direction. After calculation of $S^2$, one may select all residues with bonds have $S^2$ less than a cutoff value (e.g., $S^2<0.8$). Alternatively, one could independently normalize the $S^2$ values for each bond vector type such that the $S^2$ of the most flexible residue is 0. Then one could select the residues with the lowest $S^2$ values by selecting an internal cutoff (e.g., $S^2<0.8$). In another embodiment, one could calculate the center of mass for each residue and repeat the $S^2$ calculation using the center of mass rather than individual bond vectors of the residue(s).

In various embodiments, the RMSF, which is always greater than 0, is used to determine regions of large structural variation. For example, after superimposing the 10 low energy structures from MC-Sym predictions using a common set of residues, for example all heavy atoms in the helical region(s) of the RNA of interest, the RMSF can be calculated for chosen structural parameters of interest using the equation:

$$RMSF = \sqrt{\frac{1}{N}\sum_{i=1}^{N}(j_i - \bar{j}_i)^2}$$

where N is the number of polynucleotide structures under consideration and j is a structural feature such as atomic position, residue center of mass position etc., and $\bar{j}$ denotes the average of the structural feature averaged over the N structures. After calculation of RMSF, one may select all residues with RMSF greater than a cutoff value (e.g., RMSF>0.5 Å).

In some embodiments, to calculate the maximized chemical shift dispersion (d), where $d=\min(|\delta_i - \delta_j|)$ where $\delta_i, \delta_j \in \{_{labeled\ positions}^{calculated}\}$, a sampling algorithm such as the Kennard-Stone algorithm (R. W. Kennard, L. A. Stone, Computer aided design of experiments, Technometrics 11 (1969) 137-148) is adopted to rank a list of possible combination of labeling positions on each of the polynucleotide sample. For example, each labeled position is considered as a point in the Kennard-Stone algorithm. The algorithm works as follows: first find the two positions most dispersed or largest dispersion (d) in the trial set. For each candidate position, find the smallest dispersion (d) to any position already selected. Select that position for the training set which has the largest of these smallest dispersion. This algorithm always gives the same result, due to the two starting positions which are always the same. The results of the Kennard-Stone algorithm would provide the fewest number of necessary polynucleotides needed to be synthesized while maintaining maximum chemical shift dispersion. Using the above referenced methodologies for identifying a region of a polynucleotide for selective labeling, the present invention provides a method for selectively labeling a polynucleotide for NMR analysis. In certain embodiments, the method includes selecting polynuceotide sequence of interest; predicting 2-D structure using any 2-D structure predicting algorithm, for example, contrafold, Vienna RNA package, centroid-fold, RNAstructure, ContextFold, IPKnot, MC-Fold and the like; generating a 3-D model using any 3-D structure predicting algorithm, for example, MC-Sym, NAB (distance geometry), Rosetta FARFAR, NAST, RNA builder, and the like; determining the minimum energy conformation of the structure using molecular mechanics software, for example, NAB, NAMD, GROMACS, TINKER, CHARMM, AMBER, and the like; and calculating the regions of the RNA that exhibit large structural variation using metrics such as $S^2$ and/or RMSF, where large structural variation is defined as $S^2<0.8$ and/or RMSF$>0.5$ Å.

For regions of the RNA with large structural variations, calculate the chemical shifts from each structure using chemical shift calculation software, for example, Nymirum's Random Forest Predictors (RAMSEY), SHIFTS, NUCHEMICS, and QM methods; Using a computational algorithm(s)/software, such as the Kennard-Stone algorithm, select one or more residues that will be isotopically labeled such that the chemical shift dispersion is maximized, or is as maximized as possible, and the number of samples is minimized.

In some embodiments, the Kennard-Stone algorithm is used to select more than one residue to be isotopically labeled that does not maintain maximum chemical shift dispersion, thus affording less spectral resolution, with the goal of reducing the number polynucleotides to be synthesized.

In some embodiments, methods for determining the position on the polynucleotide sequence for isotopically labeling one or more nucleotides with one or more atomic labels include (1) determining one or more 2-D or 3-D models of the polynucleotide sequence using a 2-D or 3-D structure predicting algorithm, respectively. As used herein, a 2-D structure prediction algorithm generally relates to an algorithm(s) employed in structure prediction software such as: MC-Fold, MC-Fold-DP, Mfold, CentroidFold, ContextFold, IPKnot, ContraFold, MaxExpect, ProbKnot, Sfold, or any other polynucleotide secondary structure prediction approach, and a 3-D structure prediction algorithm is defined as the algorithm(s) employed in software such as: MC-Sym, NAB, Rosetta FARFAR, NAST, RNA builder or any other 3-D RNA structural prediction approach; (2) identifying one or more structural heterogeneous regions on each of the one or more 2-D or 3-D models of the polynucleotide sequence; (3) calculating one or more chemical shifts from the one or more structural heterogeneous regions; and (4) synthesizing a polynucleotide comprising one or more nucleotides having one or more atomic labels positioned at one or more nuclei which results in a polynucleotide having a minimized chemical shift overlap. As used herein, a chemical shift overlap can be computed by comparing the chemical shift values, using metrics such as Hz or ppm, of two or more chemical shift peaks and computing the area or volume that the two or more chemical shift peaks overlap. NMR spectral processing and analysis software can be used to compute the chemical shift overlap; examples of NMR spectral processing and analysis software include VNMRJ, NMRPipe, Sparky, or NMRView. A minimized chemical shift overlap would be measured for those chemical shift peaks that give rise to the smallest aforementioned area or volume.

In an illustrative example, minimized chemical shift overlap (d), where $d=\min(|\delta_i-\delta_j|)$ where $\delta_i$, $\delta_j \in \{\text{labeled positions}^{calculated}\}$, can be calculated using a sampling algorithm, such as the Kennard-Stone algorithm (R. W. Kennard, L. A. Stone, Computer aided design of experiments, Technometrics 11 (1969) 137-148) which can be adopted to rank a list of possible combination of labeling positions on each of the polynucleotides in the polynucleotide sample. For example, each labeled position is considered as a point in the Kennard-Stone algorithm. The algorithm works as follows: first find the two positions most dispersed or largest dispersion (d) in the trial set. For each candidate position, find the smallest dispersion (d) to any position already selected. Select that position for the training set which has the largest of these smallest dispersion. This algorithm always gives the same result, due to the two starting positions which are always the same. The results of the Kennard-Stone algorithm would provide the fewest number of necessary polynucleotides needed to be synthesized while maintaining maximum chemical shift dispersion. Other methods to calculate the chemical shift overlap include comparing the chemical shift peak positions and using metrics such as such as root-mean-squared-error, mean-absolute-error, weighted root-mean-squared-error, and weighted mean-absolute-error to compare different chemical shift peaks with the minimized chemical shift overlap being those peaks that give rise to the largest values root-mean-squared-error, mean-absolute-error, weighted root-mean-squared-error, or weighted mean-absolute-error values.

With reference to FIG. 2, in some embodiments, the first step of the method comprises selecting a polynucleotide for further study. As used herein, information regarding a polynucleotide structure can be used to determine the 2-D & 3-D atomic resolution structure of a polynucleotide of interest, assess heterogeneity of sequence and whether it folds into one or multiple structural forms; structurally map out RNA/DNA-protein and RNA/DNA-ligand interactions; measure the binding affinities/specificities between the RNA/DNA and protein, ligand and other molecules; assign NMR resonances; screen a library of small molecules, biological, or other compounds for binding to the RNA/DNA polynucleotide in question; evaluate the similarities in the 2-D and 3-D structure of different nucleotide sequences; evaluate the presence and/or absence of specific tertiary interactions; evaluate presence and/or absence of specific elements of secondary and 3-D atomic resolution structure; evaluate how changes in physiological conditions such as temperature, pH and salt affect RNA/DNA structure; evaluate protonation/tautomer state of base-pairs; evaluate structure of excited states (such as transient Hoogsteen base-pairs), among others, solve one or more small molecule bound nucleic acid (e.g., RNA or DNA) structures, and solve one or more atomic-resolution small molecule binding pockets in a nucleic acid (e.g., RNA or DNA).

Polynucleotide sequences of interest can be identified by performing a search of nucleotide sequence databases such as EMBL, Genbank, Ensembl, and others known to those of skill in the art which have identified polynucleotide sequences that can be manually searched.

In some embodiments, the next step in the generation of selectively labeled polynucleotides includes step (20), synthesizing a selectively labeled polynucleotide.

In some embodiments, the polynucleotide is synthesized by synthesizing the polynucleotide with one residue individually labeled with uniform $^{13}$C and/or $^{15}$N. In various embodiments, for a polynucleotide sequence having N-mer there will be N samples each containing a different nucleotide that is $^{13}$C and/or $^{15}$N enriched. In some embodiments, the polynucleotide is synthesized by creating a polynucleotide having labeled an A and/or U selectively labeled with $^{13}$C and/or $^{13}$N, or a G and/or C labeled with $^{13}$C and/or $^{15}$N.

In various embodiments, for a polynucleotide sequence having N-mer, the N-mer polynucleotide contains two labeled residues at a time. For example, one purine (A or G) and one pyrimidine (C or U or T) are labeled as a pair wherein one or more atoms in the purine and pyrimidine are $^{13}$C or $^{15}$N enriched. In some embodiments, each polynucleotide will contain an A and U (or T) that is $^{13}$C and/or $^{15}$N enriched, a G and C that is $^{13}$C and/or $^{15}$N enriched, or G and U (or T) that is $^{13}$C and/or $^{15}$N enriched, or a A and C that is $^{13}$C and/or $^{15}$N enriched. This method utilizes the well-separated chemical shifts of $^1$H, $^{13}$C, and $^{15}$N nuclei in nucleic acid bases ($^1$H=~1.6, $^{13}$C=~14 for T; $^1$H=~7.6, $^{13}$C=~153 for A; $^1$H=~12, $^{15}$N=~147 for G; $^1$H=~13, $^{15}$N=~160 for U or T; $^1$H=~5.5, $^{13}$C=~97 for C; $^1$H=~5.5, $^{13}$C=~103 for U; units in ppm). For the case of $^1$H chemical shift overlap, $^{13}$C or $^{15}$N chemical shifts can resolve the residue types by using a shortened version of 2D heteronuclear NMR spectra. Only 2 to 4 complex data points in the $^{13}$C or $^{15}$N dimension are sufficient to distinguish if the $^{13}$C or $^{15}$N chemical shift is higher or lower frequency than the center.

In some embodiments, the polynucleotide is synthesized and specifically labeled nucleotides are differentially added. In one example, for a given N-mer polynucleotide, multiple sites are $^{13}$C and/or $^{15}$N enriched. The final effective concentration for each residue that is $^{13}$C and/or $^{15}$N enriched will be varied according to a pre-determined mathematical function that can be dictated at the synthesis step by the inclusion of mixture of a $^{13}$C and/or $^{15}$N enriched phosphoramidite and an unlabeled phosphoramidite. This will afford assignment of a given residue according to the NMR resonance area/volume which will be directly proportional to the effective concentration of each $^{13}$C and/or $^{15}$N enriched residue. In a non-limiting example, in a given Nmer-polynucleotide, there are two Gs in the polynucleotide sequence. In order to label both Gs, one G can be labeled with 100% $^3$C and/or $^{15}$N effective concentration and the second with 50% $^{13}$C and/or $^{15}$N effective concentration. Then, both G nucleotides labeled with $^{13}$C and/or $^{15}$N can be assigned at the same time according to the area/volume of the resonance. This could also be accomplished with multiple labels with varying effective concentrations following numerical pattern (e.g., residue 1 at 100%, residue 2 at 90%, residue 3 at 80%, etc.).

In another example, selective labeling of a polynucleotide can be accomplished by modulating or altering the effective concentration of $^{13}$C and/or $^{15}$N enrichment at a given nucleotide so to that it varies according to a mathematical function such as Cos(w*t) (where t is the different samples and w is some chosen frequency). In this approach, an NMR interrogated polynucleotide using an NMR device of the present invention can encode the resonance assignments according to the effective incorporation concentration and thus by applying a Fourier transform to the NMR signal, the analysis can provide a 2-D spectrum in which the first dimension provides chemical shift data and the second dimension provides the variation in concentration.

In another non-limiting example, selective labeling of a polynucleotide sequence includes a 2-D structure based approach): Based on primary sequence, the selective labeling requires that the 2-D structure of the polynucleotide is predicted. Then the polynucleotide sequences of the top 10 or so 2-D structure predictions are aligned and then determine the sites that exhibit the greatest variance in 2-D structure. To selectively label the polynucleotide, the nucleotides that exhibit largest 2-D structural heterogeneity are labeled with an isotope for example, $^2$H, $^{13}$C, $^{15}$N, $^{19}$F or $^{31}$P.

In another non-limiting example, selective labeling of a polynucleotide can be accomplished by a 3-D atomic resolution structure based approach. In this embodiment, a 3-D atomic resolution structure prediction method can be used to generate a putative model of target RNA. For each residue or nucleotide, calculate the structural heterogeneity over the low energy models. To selectively label the polynucleotide, the nucleotides that exhibit largest structural heterogeneity are labeled with an isotope for example, $^2$H, $^{13}$C, $^{15}$N, $^{19}$F or $^{31}$P.

In various embodiments, the present methods also includes a synthesis step (30) for preparing isotopically selectively labeled polynucleotides for study using low field NMR. Step (30) can be for synthesizing target polynucleotides that contain one or more phosphoramidites labeled with one or more of $^2$H, $^{13}$C, $^{15}$N, $^{19}$F, or $^{31}$P are known in the art. Generally, chemical methods for synthesizing polynucleotides using labeled or unlabeled phosphoramidites are relatively well known and are commercially available from Dharmacon (Thermo Fisher Scientific, Waltham Mass., USA). In some embodiments, methods for producing RNA oligonucleotides from labeled or unlabeled ribonucleoside phosphoramidites can include TOM-protected RNA phosphoramidite, tert-butyldimethylsilyl (TBDMS/TBS) based synthesis, ACE protecting group synthesis and others known in the art.

Methods for purifying isolated and synthesized polynucleotides are known in the art, for example, purified labeled and unlabeled polynucleotides can be purified using HPLC, gel chromatography, polyacrylamide gel electrophoresis (PAGE), size-exclusion gel chromatography, and ion-exchange chromatography. In some embodiments, preferred methods of purifying RNA polynucleotides include non-polyacrylamide gel electrophoresis methods, for example, HPLC, affinity chromatography, size-exclusion gel chromatography and ion-exchange chromatography.

In various embodiments, methods for synthesizing an isotopically labeled ribonucleoside may generally follow one of three general approaches. The three approaches generally include biomass, enzymatic, and chemical synthesis of isotopically labeled nucleosides. Any of these methods can be employed in the synthesis of the presently described selectively labeled polynucleotides. The biomass method provides labeled ribonucleoside synthesis and purification using $^{13}$C-glucose, $^{13}$C methanol, $^{15}$N-ammonium sulfate, and $^{13}$C acetate substrates among others that are known, for isotopically labeled nucleoside production in different bacteria types. In some embodiments, methods useful in the synthesis of labeled RNA nucleotides include those that involve an enzymatic reaction.

In some embodiments, synthetic RNA or DNA nucleosides having a label selected from $^2$H, $^{13}$C, $^{15}$N, $^{19}$F, or $^{31}$P are synthesized using conventional nucleoside analog phosphoramidite chemistry. Commercially available nucleic acid (e.g., RNA or DNA) phosphoramidites incorporating a labeled $^2$H, $^{13}$C, $^{15}$N, $^{19}$F, or $^{31}$P atom can be obtained from Glen Research, SAFC, and others. Nucleic acid (e.g., RNA or DNA) phosphoramidites incorporating a labeled $^2$H, $^{13}$C, $^{15}$N, $^{19}$F, or $^{31}$P atom can be synthesized.

2. Acquisition of Chemical Shift for Determination of Polynucleotide Structure Using NMR In some embodiments, the method provides for the NMR interrogation of a target or polynucleotide of interest. In some embodiments, the target or polynucleotide of interest is bound to a small molecule. In some embodiments, the polynucleotide of interest is selectively isotopically labeled and interrogated using low field NMR. In some embodiments, the polynucleotide of interest bound to a small molecule is selectively isotopically labeled and interrogated using low field NMR.

In some embodiments, the present invention provides a method for determining the 2-D or 3-D atomic resolution structure of a polynucleotide. The method includes providing a polynucleotide sample comprising a polynucleotide, the polynucleotide comprising at least one nucleotide isotopically labeled with one or more atomic labels selected from the group consisting of $^2$H, $^{13}$C, $^{15}$N, $^{19}$F and $^{31}$P; obtaining a NMR spectrum of the polynucleotide sample using a NMR device; determining a chemical shift of the one or more atomic labels; and determining a 2-D or a 3-D atomic resolution structure of the polynucleotide from the chemical shifts determined in step (c).

In some embodiments, the present invention provides a method for determining the 3-D atomic resolution structure of a polynucleotide when bound to a small molecule, ligand or other chemical entity for purposes comprising computer-aided drug design. The method includes providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2$H, $^{13}$C, $^{15}$N, $^{19}$F and $^{31}$P; generating an NMR sample comprising one or more polynucleotides admixed with one or more small molecules that form one or more bound complexes; obtaining an NMR spectrum of the NMR sample using an NMR device; determining one or more chemical shifts of the one or more atomic labels; and determining the 3-D atomic resolution structure of the polynucleotides from the chemical shifts determined in step (d).

In some embodiments, the present invention provides a method for determining the 3-D atomic resolution binding pocket of a polynucleotide purposes comprising computer-aided drug design. The method includes identifying one or more small molecule binders that bind the polynucleotide; providing a polynucleotide sample comprising a plurality of the polynucleotide, wherein each polynucleotide comprises at least one nucleotide isotopically labeled with one or more atomic labels selected from the group consisting of $^2$H, $^{13}$C, $^{15}$N, $^{19}$F and $^{31}$P; generating an NMR sample comprising the polynucleotide sample admixed with one or more of the small molecule binders; obtaining an NMR spectrum of the NMR sample using an NMR device; determining one or more chemical shifts of the one or more atomic labels; determining the 3-D atomic resolution structure of the polynucleotides from the chemical shifts determined in step (d); and identifying the binding pocket of the one or more small molecule binders, wherein the binding pocket is identified using methods comprising, computational docking, molecular dynamics, quantum mechanics, and/or any other computer-aided methods useful to determine a small molecule binding pocket.

In some embodiments, the method to determine the 2-D or 3-D structure of a polynucleotide requires interrogation of multiple polynucleotides having the same nucleotide sequence, but differing from each other in that each polynucleotide is isotopically labeled on one or more different residues. In other words, the method determines the chemical shifts of multiple polynucleotides, each polynucleotide having the identical nucleotide sequence as the first polynucleotide analyzed, and each polynucleotide synthesized with one or more different residues comprising one or more isotopically enriched atoms. For example, if the polynucleotide has 5 residues, the method would require 5 polynucleotide samples, each polynucleotide labeled with the one or more isotopic labels on a different nucleotide. In another example, if the polynucleotide has 5 residues, the method would require less than 5 polynucleotide samples because one or more samples comprise a combination of isotopically enriched atoms such that the atoms are predicted not to exhibit spectral overlap. In some embodiments, the polynucleotide sample has only one residue isotopically enriched. In some embodiments, the polynucleotide comprises more than one residue that comprises one or more isotopically enriched atoms.

As a first non-limiting example, in a 5-mer that has the sequence AUUGC (SEQ ID NO: 1), the polynucleotide sample comprises the polynucleotide sequence AUUGC (SEQ ID NO: 1) with the first U at position 2 labeled uniformly with $^{13}$C. The method proceeds to determine the chemical shift of the isotopically labeled U. In a second non-limiting example, a different polynucleotide sample also having the polynucleotide sequence AUUGC (SEQ ID NO: 1) with the G at position 4 being labeled with $^{15}$N and $^{13}$C. This is a different polynucleotide sample as compared to the first example. In a third non-limiting example, the polynucleotide sample can contain a polynucleotide with the polynucleotide sequence AUUGC (SEQ ID NO: 1) wherein the A nucleotide residue is labeled with $^{15}$N and the C nucleotide residue is labeled with $^{13}$C. In a fourth non-limiting example, the polynucleotide sample comprises a polynucleotide with the polynucleotide sequence AUUGC (SEQ ID NO: 1) wherein the G is isotopically labeled with $^{15}$N and $^{13}$C. In each instance, the method to determine the 2-D or 3-D structure of a biomolecule, for example a polynucleotide, requires one or more polynucleotide samples, each polynucleotide sample containing a polynucleotide with the same nucleotide sequence and wherein one or more nucleotides of the polynucleotide are selectively labeled with one or more isotopically enriched atoms labels. The determination of 2-D or 3-D atomic resolution structure of a polynucleotide can utilize the chemical shift data from the first example, or the chemical shift data from any combination of examples illustrated above.

In some embodiments, the methods of the present invention utilize a low field NMR. These methods illustratively include interrogation of the target or selected polynucleotide selectively labeled with one or more nucleotides using a static magnetic field and reference frequency of 300 MHz or less, or about 299 MHz or less, or about 250 MHz or less, or about 225 MHz or less, or about 200 MHz or less, or less than about 175 MHz, or less than about 150 MHz, or less than about 125 MHz, or less than about 100 MHz, preferably, ranging from about 20 MHz to about 300 MHz, or from about 20 MHz to about 299 MHz, or from about 50 MHz to about 275 MHz, or from about 75 MHz to about 250 MHz, or from about 75 MHz to about 225 MHz, or from about 75 MHz to about 200 MHz, or from about 75 MHz to about 175 MHz, or from about 100 MHz to about 300 MHz, or from about 125 MHz to about 275 MHz, or from about 20 MHz to about 250 MHz, or from about 20 MHz to about 225 MHz, or from about 20 MHz to about 200 MHz, or from about 20 MHz to about 150 MHz, or from about 20 MHz to about 100 MHz.

Step (50) of the exemplary method of FIG. 2 provides a step in which the chemical environment for the one or more polynucleotides to be interrogated using NMR is selected. As used herein, the term "chemical environment" refers to the chemical composition of the solution in which the one or more polynucleotides will be analyzed with NMR in the analysis volume of the sample conduit. The chemical environment may include one or more solutions including, $H_2O$, $D_2O$, a salt, a buffer, a solubilizing agent, an analyte, a pH modifying agent, a screening candidate compound, a biomolecule, (for example, a DNA, RNA protein, polypeptide, lipid molecule or complex) or combinations thereof. In some embodiments, the buffer can include: Bis, Tris, Phosphate, HEPES, MOPS etc.

In some embodiments, certain buffers are useful in the present methods may or may not be uniformly deuterated so as to eliminate their signals from detection using $^1H$ NMR experiments. In some embodiments, representative examples of salts can include: NaCl, $MgCl_2$, KCl, $MnCl_2$, etc.

In some embodiments, the methods of the present invention are used to determine whether binding between a protein and a polynucleotide has occurred, or determine the region of the polynucleotide involved in binding a particular agonist or antagonist agent. In various embodiments, the chemical environment is selected such that a perturbation agent is added to the target polynucleotide to study the 3-D atomic resolution structure of the polynucleotide in the presence of such perturbation agents. In some embodiments, a titration of any proportion of analyte is added to the polynucleotide. In this case multiple chemical shifts for each resonance, each having a different chemical environment of analyte, are recorded and used to determine parameters comprising one or more of binding site, K, and kinetics. A chemical shift that changes position or intensity, area, and/or volume on addition of analyte, in some embodiments, is indicative of a structural change at that site and/or interaction with the analyte. Thus, in some embodiments, focusing on the nucleotides that have a changing chemical shift on addition of analyte, will allow one to determine one or more of the binding site, $K_d$, and kinetics.

Without limitation to any one particular theory, it is believed that chemical shift positions can be input into functions such as the equation below for regression analysis in order to determine the $K_d$ in which AT and BT are total concentration (bound+free) of substrates A and B, respectively. Other equations can be used for determination of rate constants and other binding mechanisms.

$$AB = \frac{(A_T + B_T + K_D) - \sqrt{(A_T + B_T + K_D)^2 - 4(A_T B_T)}}{2}$$

In some embodiments, the sample containing the polynucleotide of interest which is single stranded or double stranded is heated to a temperature from about 50° C. to about 95° C. for 5 minutes, and then gradually reduce the heat until the polynucleotide has reached room temperature to anneal the polynucleotide prior to NMR interrogation using an NMR device as described herein. In some embodiments, this heating and cooling process is bone in the absence or presence of a small molecule that is being studied to determine whether the small molecule binds the polynucleotide.

Step (60) of FIG. 2 provides the next step in the exemplified methods described herein. In step (60), in some embodiments, the method further includes interrogation of the selectively labeled polynucleotide using NMR, for example low field NMR. The interrogation of the selectively labeled polynucleotide comprises at least one of: structural determination of the 2D & 3-D structure of a polynucleotide of interest, assess heterogeneity of sequence and whether it folds into one or multiple structural forms; structurally map out RNA/DNA-protein, RNA/DNA-ligand, and RNA/DNA-small molecule interactions; measure the binding affinities/specificities between the RNA/DNA and protein, ligand, small molecules, and other molecules; assign NMR resonances; measure one or more NMR data (e.g., chemical shifts), of RNA/DNA-protein, RNA/DNA-ligand, and/or RNA/DNA-small molecule interactions, screen a library of small molecules, biological, or other compounds for binding to the RNA/DNA; evaluate the similarities in the 2-D and 3-D structure of different nucleotide sequences; evaluate presence/absence of specific tertiary interactions; evaluate presence/absence of specific elements of secondary and 3-D atomic resolution structure; evaluate how changes in physiological conditions such as temperature and pH affect RNA/DNA structure; evaluate protonation/tautomer state of basepairs; and evaluate structure of excited states (such as transient Hoogsteen base-pairs).

In some embodiments, the NMR interrogation step (60) includes one or more of the following 6 steps:

a. First, in some embodiments, comprises a temperature regulation step. In this aspect, the liquid sample containing the polynucleotide of interest in the appropriate chemical environment is transferred to a sample conduit and fills the analysis volume with sample for NMR interrogation.

b. Second, in some embodiments, the sample in the sample conduit is equilibrated at a selected temperature ranging from 0 to 60° C.

c. Third, in some embodiments, a tuning and matching step can be performed. This process adjusts the resonant circuit frequency and impedance until they coincide with the frequency of the pulses transmitted to the circuit and impedance of the transmission line (typically 50 ohm). For best signal-to-noise and minimal RF coil heating, the tuning and matching should be done for each sample. But with pre-adjustment during manufacturing process, minor or no adjustment is necessary for low field magnets.

d. Fourth, in some embodiments, a locking step is performed. In this process, the 2H signal is found from deuterated solvent for internal feedback mechanism by which magnetic field drift can be compensated. The $^2H$ signal (for example, 30.7 MHz at 200 MHz spectrometer) being distant from $^1H$ signal is acquired and processed independently. Lock signal also serves as chemical shift reference.

e. Fifth, in some embodiments, prior to acquiring NMR data on the sample being interrogated is a shimming step. In some embodiments, the interrogation step may require creating a homogeneous magnetic field at the analysis volume by controlling electric currents in a set of coils which generate small static magnetic fields of different geometries and strength and correct inhomogeneity of the $B_0$. For NMR interrogation of biomolecules of the present invention, it is preferred to have at least 50 ppb (part per billion) of field homogeneity when analyzing samples using NMR.

f. Sixth, in some embodiments, a sequence of precise pulses and delays are applied to $^1$H and $^{13}$C transmission lines connected to each resonant circuit around the analysis volume to manipulate spin quantum states of nuclei in the sample. As a result, only the desired signals such as $^1$H nuclei spins attached to $^{13}$C are selected and measured excluding all other $^1$H nuclei spins attached to other nuclei, or using shaped pulses (selective pulses) nuclei having certain chemical shift range are detected. Many different types of pulse sequences can be applicable for different purposes including a variety of HSQC, HMQC, COSY, TOCSY, NOESY, ROESY for structural determinations of biomolecules in 1-D, 2-D, and 3-D experimental settings. In some embodiments, after the pulse sequence, the same resonant circuits (including the 2 or more RF coils) are sensing fluctuation of magnetic field around analysis volume (called FID; free induction decay) as electric voltage which is digitized and recorded for predefined duration. To improve the signal-to-noise (S/N), a set of pulsing and recording steps are repeated multiple times and added with some delay in between, called relaxation delay which allow spin systems to return to initial state before starting pulsing.

3. NMR Signal Processing

As shown in FIG. 2, once the polynucleotide in the analysis volume has been interrogated using NMR, in some embodiments, the signals emitted from the target nuclei are converted from an analog signal and converted to a digital signal. The next step in determining the chemical shifts of the various nuclei in the polynucleotide sample required for structure determination step (70) involves processing the NMR signals for determination of the chemical shifts of the various nuclei.

In various embodiments, the first step in such a determination comprises a Fourier transformation step. The acquired FID (free induction decay) in IUPAC JCAMP-DX or other proprietary format is read and converted to an internal data format. Standard processing techniques such as zero-filling, apodization (or window functions), and baseline correction applied along with Fourier transformation and phase correction for balancing between sensitivity and resolution are, in some embodiments, employed. In various embodiments, the next step can include a peak picking step. In this step, the Fourier transformed spectrum is analyzed to detect position (in Hz and ppm unit) and intensity (or height)/area under a peak/volume enclosing a peak (in 2-D and 3-D) (in arbitrary unit) of peaks using the fitness of spectral shape to 2-D or 3-D Gaussian, Lorentzian, or other shapes, which generates a list of peak positions and intensities (or heights), areas under peaks, and volume within enclosed peaks. In some embodiments, next, the NMR signal processing step (70) includes a chemical shift referencing step. In this step, the chemical shift of DSS (4,4-dimethyl-4-silapentane-1-sulfonic acid) or TSP (trimethylsilyl propionate) or other compounds at 0 ppm is used as reference for chemical shifts of other atoms. Using information of sample and internal reference concentration and $^2$H lock frequency, internal reference peak at around 0 ppm is identified from the peak list and set as 0 ppm for reference purpose. In some embodiments, chemical shift assignments can also be facilitated through the use software programs such as SHIFTS and NUCHEMICS. In some embodiments, chemical shift assignments can also be facilitated through the use quantum mechanical calculations. In some embodiments, chemical shift assignments can be facilitated through machine learning (e.g., random forest) chemical shift predictors.

Next, with reference to FIG. 2, in some embodiments, the methods of the present invention also provide a step involving the generation and selection of a structural model of the polynucleotide based on the chemical shift data and other NMR constraints obtained during the NMR interrogation step. In some embodiments, step (80) can employ any of the methods provided below for the determination of 3-D and 4-D atomic resolution structure using the chemical shift and other NMR data during the NMR interrogation step. In various embodiments, chemical shift data and other NMR constraints obtained during the NMR interrogation step are obtained from the polynucleotide when bound and/or interacting with one or more small molecules. In various embodiments, the NMR data of the polynucleotide when bound and/or interacting with one or more small molecules are used to determine a structure, model, and/or binding pocket of the polynucleotide. In some embodiments, the binding pocket comprises descriptions of atomic-interactions between the RNA and one or more putative small molecule binders. In some embodiments, the binding pocket is useful for structure-based drug design, medicinal chemistry, and other drug discovery disciplines.

In some embodiments, a conformational sampling method is used to generate many candidate models for polynucleotide (e.g., RNA, DNA, nucleic acid) of interest. For each candidate model, the user can back-predict NMR data e.g., chemical shifts, NOE, J-coupling and RDC, collectively referred to as the theoretical NMR data. The user can then select the model or select number of models that best agree with experimental NMR data as the solved structure of the nucleic acid. In some embodiments the experimental data are filtered to determine which chemical shift data and/or other NMR data are perturbed by small molecule binding. In various embodiments, chemical shifts that are perturbed due to interactions with the electronic field of the small molecule are filtered and thus not used to solve the polynucleotide (e.g., RNA, DNA, nucleic acid) structure. In various embodiments, NMR data that are perturbed due to interactions with the electronic and/or magnetic field (e.g., dipolar couplings and/or cross relaxation) of the small molecule are filtered and thus not used to solve the polynucleotide (e.g., RNA, DNA, nucleic acid) structure. In various embodiments, filtering the NMR data (e.g., chemical shifts) improves the accuracy and/or resolution of the polynucleotide structure. In various embodiments, filtering the NMR data (e.g., chemical shifts) is necessary to solve an accurate and/or high resolution of the polynucleotide structure.

In various embodiments a database of polynucleotide NMR data (e.g., chemical shifts) is generated. This database is used to compare experimentally measured NMR data (e.g., chemical shifts) in order to determine whether the measured NMR data are outliers of the database. In some embodiments, NMR data that lie outside the NMR data in the database are filtered and thus not used to solve the polynucleotide structure. In various embodiments, NMR data that lie outside the NMR data in the database result from atoms that are interacting and/or near other atoms that are interacting with another molecule, for example, a small molecule. In various embodiments, atoms that are near other atoms interacting with another molecule are about 1 bond, about 2 bonds, about 3 bonds, about 4 bonds, about 5 bonds, about 6 bonds, about 8 bonds, about 9 bonds, or about 10 bonds distant from the atoms interacting with another molecule.

In various embodiments, experimentally measured NMR data (e.g., chemical shifts) are compared to calculated chemical shifts in order to determine whether the measured NMR data are outliers of the database. In some embodiments, the calculated chemical shifts define whether experimentally measured NMR data (e.g., chemical shifts) are within ranges of previously measured NMR data. In various embodiments, NMR data are calculated using software, for example, NUCHEMICS, SHIFTS, quantum mechanics, or any other method developed to calculate NMR data. In some embodiments, NMR data that lie outside ranges previously observed result from atoms that are interacting and/or near other atoms that are interacting with another molecule, for example, a small molecule. In various embodiments, atoms that are near other atoms interacting with another molecule are about 1 bond, about 2 bonds, about 3 bonds, about 4 bonds, about 5 bonds, about 6 bonds, about 8 bonds, about 9 bonds, or about 10 bonds distant from the atoms interacting with another molecule.

In some embodiments, experimental NMR data, e.g., chemical shifts, NOE, J-coupling and RDC to generate structure restraints are incorporated into molecular dynamics (MD) simulations to generate a plurality of conformers or ensembles. The restraint MD simulation sample ensembles that best satisfy the experimentally derived restraints are then collected. Finally, the ensemble or conformer generated during the MD simulation that best agrees with experimental NMR data is selected as the solved structure of the polynucleotide. In some embodiments, ensembles can be constructed using chemical shifts data using the sample and select (SAS) approach as described previously in U.S. patent application Ser. No. 13/120,064, published as U.S. Patent Application Publication No. 2011/0172981, the disclosure of which is incorporated herein by reference in its entirety. The ensembles can be selected by the use of a minimizing cost function, for example, using Monte Carlo procedures (see below), the cost function expressed in the following equation:

$$\chi^2_{CS} = \frac{1}{L_{CS}} \sum_{i=1}^{N} \left( \delta_i^{pred} - \delta_i^{meas} \right)^2$$

Here $\delta_i^{pred}$ and $\delta_i^{meas}$ are the predicted and measured chemical shifts for the $i^{th}$ proton, respectively, and $L_{CS}$ is the total number of chemical shift, respectively. Each selection cycle is initiated from N randomly selected conformers. A Monte Carlo (MC) simulated annealing scheme is then used to minimize the equation. Simulations were initiated at a high "temperature" (a parametric, effective temperature), where the MC acceptance probability was high (0.99), and slowly decreased until the MC acceptance probability was $10^{-5}$. At a given effective temperature $10^5$ MC steps were carried out. The effective temperature was then decreased according to the exponential schedule $T_{(n+1)} = 0.92\ T_n$. This selection is repeated e.g., 10-1000 times, generating in the range 10*N to 1000*N conformers that pool together used a representative dynamical ensemble.

In some embodiments, generation and selection of a structural model step (80) comprises the steps:

a. predict 2-D polynucleotide structure using any structure predicting algorithm, for example, contrafold, Vienna RNA package, centroid-fold, RNAstructure, ContextFold, IPKnot, MC-Fold, MFold, and the like;
b. generate a 3-D polynucleotide model using 3-D structure predicting algorithm, for example, MC-Sym, NAB (distance geometry), Rosetta FARFAR, NAST, RNA builder, and the like;
c. determine the minimum energy conformation of the structure using molecular mechanics software, for example, NAB, NAMD, GROMACS, TINKER, CHARMM, AMBER, and the like;
d. back-calculate the chemical shifts from each model using chemical shift calculation software, for example, Nymirum's Random Forest Predictors (e.g., RAMSEY), SHIFTS, NUCHEMICS, and QM methods;
e. compare experimental and predicted chemical shifts for each model; and
f. select the model that exhibits the best agreement between experimental and predicted chemical shifts.

In some embodiments the experimental chemical shifts are measured from a polynucleotide bound to and/or interacting with another molecule, for example a small molecule (e.g., molecules in Table 1), a protein, a ligand, an RNA, a DNA, a salt, an ion, an atom, a molecule, and/or any nucleic acid. In some embodiments, the chemical shifts are filtered and/or a portion of the chemical shift are not used because they contain effects due to interacting with the electronic field (e.g., electrons) of the another molecule. In some embodiments, in step (a) a 2-D polynucleotide structure is known and/or assumed rather than or in addition to predicting a 2-D structure.

In some embodiments, generation and selection of a structural model step (80) comprises the steps:

a. predict 2-D polynucleotide structure using any structure predicting algorithm, for example, contrafold, Vienna RNA package, centroid-fold, RNAstructure, ContextFold, IPKnot, MC-Fold, MFold, and the like;
b. generate a 3-D polynucleotide model using 3-D structure predicting algorithm, for example, MC-Sym, NAB (distance geometry), Rosetta FARFAR, NAST, RNA builder, and the like;
c. determine the minimum energy conformation of the structure using molecular mechanics software, for example, NAB, NAMD, GROMACS, TINKER, CHARMM, AMBER, and the like;
d. back-calculate the chemical shifts from each model using chemical shift calculation software, for example, Nymirum's Random Forest Predictors (e.g., RAMSEY), SHIFTS, NUCHEMICS, and QM methods;
e. compare experimental and predicted chemical shifts for each model; and
f. select the model that exhibits the best agreement between experimental and predicted chemical shifts.
g. Identifying one or more small molecule binding pockets on the 3-D structure, using binding pocket identification software, for example, rDcavity, fpocket, ICM pocketfinder, and/or Schrodinger's SiteMap.

In some embodiments, the present invention provides a method for determining the 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid, once the polynucleotide in the analysis volume has been interrogated using NMR. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:
  a. predicting 2-D polynucleotide structure using any structure predicting algorithm, for example, contrafold, Vienna RNA package, centroid-fold, RNAstructure, ContextFold, IPKnot, MC-Fold, MFold, and the like;
  b. generating a 3-D polynucleotide model using 3-D structure predicting algorithm, for example, MC-Sym, NAB (distance geometry), Rosetta FARFAR, NAST, RNA builder, and the like;
  c. determining the minimum energy conformation of the structure using molecular mechanics software, for example, NAB, NAMD, GROMACS, TINKER, CHARMM, AMBER, and the like;
  d. back-calculating the chemical shifts from each model using chemical shift calculation software, for example, Nymirum's Random Forest Predictors (e.g., RAMSEY), SHIFTS, NUCHEMICS, and QM methods;
  e. comparing experimental and predicted chemical shifts for each model; and
  f. selecting the model that exhibits the best agreement between experimental and predicted chemical shifts.
  g. Identifying one or more small molecule binding pockets on the 3-D structure, using binding pocket identification software, for example, rDcavity, fpocket, ICM pocketfinder, and/or Schrodinger's SiteMap.
  h. Associating to the one or more binding pockets identified in the polynucleotide 3-D structure the another molecule using, for example a software, for example ICM, Schrodinger's Glide, rDock, MOE etc.;
  i. Refining the docked binding pocket and the corresponding polynucleotide 3-D structure by inputting the docked polynucleotide 3-D structure into a modeling software comprising one or more of molecular dynamics software (e.g., NAMD, GROMACS, AMBER, CHARMM), quantum mechanical software (e.g., GAUSSIAN, GAMES), molecular mechanics software (e.g., TINKER), RNA modeling software (e.g., FARNA, ROSETTA, MC-Sym, 3D-RNA).

In some embodiments, refining comprises energy minimization and/or a molecular dynamics simulation. In some embodiments, a plurality of 3-D structure selected by comparing the respective predicted chemical shift set and the chemical shift(s) of the one or more atomic labels as the 3-D atomic resolution structures, wherein one or more of the plurality of the selected 3-D structures are not in the closest agreement of the respective predicted chemical shift set and the chemical shift(s) of the one or more atomic labels as the 3-D atomic resolution structure. In various embodiments, when a plurality of 3-D structure are selected, one or more of the plurality of 3-D structures are input into steps (g) and/or (h). In various embodiments, when one or more of the plurality of structures are input into steps (g) and/or (h), one or more of the structures are selected as the "bound-structure" based on, for example, an energy, a score, a subjective metric, and/or any other structure and/or energy-related metric.

In various embodiments, associating to the one or more binding pockets identified in the polynucleotide 3-D structure comprises computational docking methods, molecular modeling methods, experimentally-informed methods or any method that places the another molecule in the binding pocket.

In some embodiments, generation and selection of a structural model step (80) comprises the steps:
  a. generating a plurality of theoretical structural polynucleotide 2-D models using the nucleotide sequence and one or more 2-D structure predicting algorithms and/or inputting a known or assumed polynucleotide 2-D;
  b. generating a plurality of theoretical structural polynucleotide 3-D models using a 3-D structure predicting algorithm using the one or more of the plurality of theoretical and/or known and/or assumed structural polynucleotide 2-D models;
  c. generating a predicted chemical shift set for each of the plurality of theoretical structural polynucleotide 3-D models;
  d. comparing the predicted chemical shift set to the chemical shift(s) of the one or more atomic labels;
  e. selecting a theoretical structural polynucleotide 3-D model having the closest agreement between the respective predicted chemical shift set and the chemical shift(s) of the one or more atomic labels as the 3-D atomic resolution structure;
  f. Identifying one or more binding pockets on the 3-D structure, using binding pocket identification software, for example, rDcavity, fpocket, ICM pocketfinder, and/or Schrodinger's SiteMap;
  g. Associating to the one or more binding pockets identified in the polynucleotide 3-D structure the another molecule using, for example a software, for example ICM, Schrodinger's Glide, rDock, MOE etc.;
  h. Refining the docked binding pocket and the corresponding polynucleotide 3-D structure by inputting the docked polynucleotide 3-D structure into a modeling software comprising one or more of molecular dynamics software (e.g., NAMD, GROMACS, AMBER, CHARMM), quantum mechanical software (e.g., GAUSSIAN, GAMES), molecular mechanics software (e.g., TINKER), RNA modeling software (e.g., FARNA, ROSETTA, MC-Sym, 3D-RNA); and
  i. Identifying the refined binding pocket of the corresponding polynucleotide 3-D structure.

In some embodiments, refining comprises energy minimization and/or a molecular dynamics simulation. In some embodiments, a plurality of 3-D structure selected by comparing the respective predicted chemical shift set and the chemical shift(s) of the one or more atomic labels as the 3-D atomic resolution structures, wherein one or more of the plurality of the selected 3-D structures are not in the closest agreement of the respective predicted chemical shift set and the chemical shift(s) of the one or more atomic labels as the 3-D atomic resolution structure. In various embodiments, when a plurality of 3-D structure are selected, one or more of the plurality of 3-D structures are input into steps (g) and/or (h) and/or (i). In various embodiments, when one or more of the plurality of structures are input into steps (g) and/or (h) and/or (i), one or more of the structures are selected as the "bound-structure" based on, for example, an energy, a score, a subjective metric, and/or any other structure and/or energy-related metric.

In various embodiments, associating to the one or more binding pockets identified in the polynucleotide 3-D structure comprises computational docking methods, molecular modeling methods, experimentally-informed methods or any method that places the another molecule in the binding pocket.

In various embodiments, identifying the refined binding pocket of the corresponding polynucleotide 3-D structure comprises one or more of: (1) using the coordinates of the another molecule to define an approximate binding pocket, and/or (2) identifying the binding pocket on the 3-D structure, using binding pocket identification software, for example, rDcavity, fpocket, ICM pocketfinder, and/or Schrodinger's SiteMap. In some embodiments, when the coordinates of the another molecule are used to define an approximate binding pocket, each atom, for example a heavy atom and/or any atom, and a radius therefrom are used to define the maximum boundary of the binding pocket. In various embodiments, the radius comprises about 0.1 angstroms, about 0.2 angstroms, about 0.3 angstroms, about 0.4 angstroms, about 0.5 angstroms, about 0.6 angstroms, about 0.7 angstroms, about 0.8 angstroms, about 0.9 angstroms, about 1 angstroms, about 2 angstroms, about 3 angstroms, about 4 angstroms, about 5 angstroms, about 6 angstroms, about 7 angstroms, about 8 angstroms, about 9 angstroms, about 10 angstroms, or any combination thereof.

In some embodiments, the present invention provides a method for determining the 2-D or 3-D atomic resolution structure of a polynucleotide. In some examples, the method comprises: providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2$H, $^{13}$C, $^{15}$N, $^{19}$F and $^{31}$P; obtaining a NMR spectrum of the polynucleotide sample using a NMR device; determining a chemical shift of the one or more atomic labels; and determining a 2-D or a 3-D atomic resolution structure of the polynucleotides from the chemical shifts.

In some embodiments, the present invention provides a method for determining the 2-D or 3-D atomic resolution structure of a polynucleotide bound to and/or interacting with another molecule, for example a small molecule (e.g., molecules in Table 1), a protein, a ligand, an RNA, a DNA, a salt, an ion, an atom, a molecule, and/or any nucleic acid. In some examples, the method comprises: providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2$H, $^{13}$C, $^{15}$N, $^{19}$F and $^{31}$P; obtaining a NMR spectrum of the polynucleotide sample using a NMR device; determining a chemical shift of the one or more atomic labels; and determining a 2-D or a 3-D atomic resolution structure of the polynucleotides from the chemical shifts.

In some embodiments, the present invention provides a method for determining the 3-D atomic resolution structure of a polynucleotide, once the polynucleotide in the analysis volume has been interrogated using NMR. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:

a. generating a plurality of theoretical structural polynucleotide 2-D models using the nucleotide sequence and one or more 2-D structure predicting algorithms and/or inputting a known or assumed polynucleotide 2-D;

b. generating a plurality of theoretical structural polynucleotide 3-D models using a 3-D structure predicting algorithm using the one or more of the plurality of theoretical and/or known and/or assumed structural polynucleotide 2-D models;

c. generating a predicted chemical shift set for each of the plurality of theoretical structural polynucleotide 3-D models;

d. comparing the predicted chemical shift set to the chemical shift(s) of the one or more atomic labels; and e. selecting a theoretical structural polynucleotide 3-D model having the closest agreement between the respective predicted chemical shift set and the chemical shift(s) of the one or more atomic labels as the 3-D atomic resolution structure.

In some embodiments, the present invention provides a method for determining the 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid, once the polynucleotide in the analysis volume has been interrogated using NMR. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:

a. generating a plurality of theoretical structural polynucleotide 2-D models using the nucleotide sequence and one or more 2-D structure predicting algorithms and/or inputting a known or assumed polynucleotide 2-D;

b. generating a plurality of theoretical structural polynucleotide 3-D models using a 3-D structure predicting algorithm using the one or more of the plurality of theoretical and/or known and/or assumed structural polynucleotide 2-D models;

c. generating a predicted chemical shift set for each of the plurality of theoretical structural polynucleotide 3-D models;

d. comparing the predicted chemical shift set to the chemical shift(s) of the one or more atomic labels; and e. selecting a theoretical structural polynucleotide 3-D model having the closest agreement between the respective predicted chemical shift set and the chemical shift(s) of the one or more atomic labels as the 3-D atomic resolution structure.

In some embodiments, the present invention provides a method for determining the 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid, once the polynucleotide in the analysis volume has been interrogated using NMR. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:

a. generating a plurality of theoretical structural polynucleotide 2-D models using the nucleotide sequence and one or more 2-D structure predicting algorithms and/or inputting a known or assumed polynucleotide 2-D;
b. generating a plurality of theoretical structural polynucleotide 3-D models using a 3-D structure predicting algorithm using the one or more of the plurality of theoretical and/or known and/or assumed structural polynucleotide 2-D models;
c. generating a predicted chemical shift set for each of the plurality of theoretical structural polynucleotide 3-D models;
d. filtering the chemical shifts to identify chemical shifts that are perturbed due to the electronic field and/or environment of the another molecule;
e. comparing the predicted chemical shift set to the chemical shift(s) of the one or more atomic labels; and
f. selecting a theoretical structural polynucleotide 3-D model having the closest agreement between the respective predicted chemical shift set and the chemical shift(s) of the one or more atomic labels as the 3-D atomic resolution structure.

As used herein, an illustrative 2-D structure prediction algorithm is defined as an algorithm(s) employed in software such as: MC-Fold, MC-Fold-DP, Mfold, CentroidFold, ContextFold, IPKnot, ContraFold, MaxExpect, ProbKnot, Sfold, or any other polynucleotide secondary structure prediction approach.

As used herein, generating a predicted chemical shift set for each of the plurality of theoretical structural polynucleotide 3-D models, includes determination of a chemical shift set wherein, the algorithms present in the software, such as, Nymirum's Random Forest Predictors (RAMSEY), SHIFTS, NUCHEMICS, or quantum mechanics methodologies, all of which generally take as input the 3-D atomic coordinates of one or more theoretical polynucleotide 3-D models and output predicted chemical shifts for one or more atoms in the theoretical polynucleotide 3-D models. Such software and algorithms are provided in: (RAMSEY): Prediction of RNA 11-H and 13C Chemical Shifts—A Structure Based Approach. Frank A T, Bae S H, Stelzer A C. J. Phys. Chem. B, 2013 September; (SHIFTS); (NUCHEMICS): and generally, as provided in "Quantum mechanics based": Fonville J M. et al. Chemistry. 2012 Sep. 24; 18(39):12372-87.

In some of the above embodiments, generating the predicted chemical shift set comprises: calculating a polynucleotide structural metric comprising atomic coordinates, stacking interactions, magnetic susceptibility, electromagnetic fields, or dihedral angles from one or more experimentally determined polynucleotide 3-D structures; generating a set of mathematical functions or objects that describe relationships between experimental chemical shifts and the polynucleotide structural metric of the experimentally determined 3-D polynucleotide structures using a regression algorithm; calculating a polynucleotide structural metric for each of the theoretical structural polynucleotide 3-D models; inputting the polynucleotide structural metric for each of the theoretical structural polynucleotide 3-D models into the set of mathematical functions or objects to generate the predicted chemical shift set.

As used above, a "polynucleotide structural metric" comprises one or more of: a structure data comparator representing any one or more of: atomic coordinates, stacking interactions, magnetic susceptibility, electromagnetic fields, or dihedral angles from one or more experimentally determined polynucleotide 3-D structures, one or more parameters describing interactions between a polynucleotide and a small molecule, for example stacking interactions, hydrogen bonding, ionic interactions, van der Waals interactions, and/or ay small molecule-polynucleotide contact. In some embodiments, a predicted chemical shift set is generated by comparing each theoretical structural polynucleotide 3-D model with a NMR-data polynucleotide structure database. In various embodiments, A NMR-data polynucleotide structure database is a database that relates NMR data such as chemical shifts, residual dipolar couplings, scalar couplings, peak intensities, relaxation rates, NOEs, or any other data measured from NMR spectra to experimentally determined or computationally modeled 2-D or 3-D polynucleotide structures.

In some embodiments, the predicted and experimental chemical shifts can be compared using various metrics such as root-mean-squared-error (RMSE), mean-absolute-error (MAE), weighted root-mean-squared-error (wRMSE), and weighted mean-absolute-error (wMAE):

$$RMSE = \sqrt{\frac{1}{N}\sum_n (\delta_{n,exp} - \delta_{n,pred})^2}$$

$$MAE = \frac{1}{N}\sum_n |\delta_{n,exp} - \delta_{n,pred}|$$

$$wRMSE = \sqrt{\sum_i \sum_j w_i(\delta_{ij,exp} - \delta_{ij,pred})^2}$$

$$wMAE = \sum_i \sum_j w_i |\delta_{ij,exp} - \delta_{ij,pred}|$$

in which $\delta_{exp}$ and $\delta_{pred}$ are experimental and predicted chemical shifts, respectively; i is the index for nuclei types (H1', H2', H3', H4', H5', H5", H2, H5, H6, H8, C1', C2', C3', C4', C5', C2, C5, C6, and C8); j is the index for the subset of chemical shifts data for each nucleus type i; iteration of i and j is equal to total number of chemical shifts, N; $w_i$ is a weight factor that equalize the differential prediction errors for different nuclei types.

In some embodiments, the weight factor $w_i$ is defined in various ways. For example, the weight factor can be defined using the Pearson coefficient R and RMSE:

$$w_i = \frac{R_i^2}{RMSE_i}$$

in which $R_i$ and $RMSE_i$ are the Pearson correlation coefficient and the root-mean-squared-error for the chemical shift prediction of nucleus type i, respectively. Other mathematical forms of weight factor can be used to equalize the differential prediction errors for different nuclei types.

In some embodiments, molecular dynamics simulations are employed to refine the selected model. In various embodiments, the following steps can be employed: (1) use experimental chemical shifts to predict dihedral angles. In some embodiments, the predicted dihedral angles can be determined using random forest, neural network or any other machine learning approach against a chemical shift and structure database; (2) generate dihedral constraints; (3) starting from a model generated using MC-Sym, NAB (distance geometry), Rosetta FARFAR NAST, RNA builder or any other RNA structural prediction approach, carryout restrained MD using dihedral constraints and any other available structure restraints software, for example, NAMD, XPLOR, GROMACS, CHARMM, TINKER. In some embodiments, the restrained MD is carried out in vacuum, followed by extensive simulation in implicit or explicit solvent; (4) extract models from MD trajectory; (5) back-calculate chemical shifts from each model; (6) for each model, compare experimental and predicted chemical shifts; and (7) select the model that exhibits the best agreement between experimental and predicted chemical shifts.

In another aspect of the molecular dynamics simulation approach, a structural model for the 3-D structure of a polynucleotide is obtained by performing the molecular dynamics simulation de novo. In this aspect, the user: (1) obtains a predicted 2-D structure using mc-fold, mfold or any other 2-D structure predicting algorithm; (2) uses 2-D structure to generate base pairing distance constraints; (3) uses the experimental chemical shifts obtained during the NMR interrogation step described above to predict dihedral angles, wherein the predicted models are generated dihedrals angles are generated using random forest, neural network or any other machine learning or regression approach against a chemical shift and structure database; (4) the user then generates dihedral constraints for the polynucleotide; (5) then starting from an ideal extended or random RNA structure, the user performs restrained MD simulations using distance and dihedral constraints and any other available structure restraints obtained during the NMR interrogation; In some embodiments, the restrained MD is carried out in vacuum, followed by extensive simulation in implicit or explicit solvent; (6) the user then extracts one or more models from the calculated MD trajectory; (7) the user then back-calculates the chemical shifts of selected nuclei from each model using chemical shift software, for example: Nymirum's Random Forest Predictors (RAMSEY), SHIFTS, NUCHEMICS, or QM methods; (8) for each model, experimental and predicted chemical shifts are compared; and (9) the user can select the model that exhibits the best agreement between experimental chemical shifts obtained and predicted chemical shifts.

In some embodiments, the last step shown in FIG. 2, the output 3-D structure of the polynucleotide of interest as contained in the specific chemical environment selected is validated. In various embodiments, the validation and outputting step 90 is performed by using an input model that best agrees with the experimental chemical shifts determined during the experimental NMR interrogation. In some embodiments, NMR relevant observables, for example, NOEs, J-coupling, RDCs, etc., are back-calculated from the polynucleotide of interest. In some embodiments, the theoretical model is used to prepare predicted NMR data, for example, NOEs, J-coupling, RDCs, etc. which are compared to the experimentally obtained data such as NOEs, J-coupling, RDCs, etc. The model selected should exhibit reasonable agreement with experimental NOEs, J-coupling, RDCs, etc. The selected model of the 3-D structure of the selective labeled polynucleotide with isotopically nuclei interrogated using low field NMR can then be outputted as a validated structure to the user.

In various aspects of the methods of the present invention, 3-D structures of polynucleotides that are solved using the devices and methods of the present invention can be uploaded into a proprietary network for future use by other users. In this aspect, solved or predicted 3-D structures of biomolecules, for example, polynucleotides, proteins and polypeptides are cataloged and stored in memory banks for future use by a user having a similar or identical sequence or subsequence to facilitate structure prediction and determination. In addition to the 3-D structure of the submitted biomolecule, experimental and quantified NMR constraints such as chemical shifts, NOEs, J-coupling, RDCs, etc., can be associated with the submitted structure.

In some embodiments, the present invention provides an NMR system for determining the 3-D atomic resolution structure and dynamics of a polynucleotide. In some embodiments, the system or method employing the NMR device of the present invention comprises for determining a 2-D or 3-D atomic resolution structure of a biomolecule, for example, a polynucleotide, for example, an RNA polynucleotide comprises: providing a low-field NMR device having a spectrometer frequency of 300 MHz or less, the NMR device comprising a housing; a sample handling device operable to receive a sample containing the biomolecule; and a NMR module, wherein the NMR module comprises: a sample conduit comprising an analysis volume operable to receive at least a portion of the sample from the sample handling device; a first tuned coil surrounded by a second tuned coil with the first and the second tuned coil(s) disposed proximately to the analysis volume, wherein each of the first and the second tuned coil(s) being operable to generate a distinct excitation frequency pulse across the analysis volume to generate nuclear magnetic resonance of a plurality of isotopically labeled nuclei of the biomolecule in the analysis volume; and at least one magnet operable to provide a static magnetic field across the analysis volume and the first and said second tuned coil(s); placing an isotopically labeled biomolecule sample in the sample conduit; obtaining a NMR spectra of the biomolecule; determining a chemical shift of the one or more atomic labels; and determining a 2-D or a 3-D atomic resolution structure of the polynucleotides from the chemical shifts determined in step (d).

In some embodiments of the above system or method, obtaining a NMR spectra or spectrum of the biomolecule includes obtaining NMR spectra using a NMR spectrometer frequency of about 20 MHz to about 300 MHz, or from 20 MHz to about 250 MHz, or from 20 MHz to about 200 MHz, or from 20 MHz to about 150 MHz, or from 20 MHz to about 100 MHz, or from 20 MHz to about 75 MHz.

In various embodiments, the NMR device of the present invention for use in the above method may also require placing a biomolecule sample in the sample conduit and optionally heating or cooling the biomolecule in the sample conduit prior to or during obtaining a NMR spectra of the biomolecule. In some embodiments, the 2-D or 3-D atomic resolution structure of the polynucleotide under investigation is first annealed and then subsequently cooled to obtain a thermodynamically favorable structure. The availability of a heating and cooling element in the NMR device may also favorably prevent unwanted molecular movement, base pairing, self-binding and the like.

In various embodiments of the present methods, obtaining a NMR spectra of the biomolecule further includes applying a pulsed field gradient during acquisition of experimental chemical shift data of the plurality of nuclei of the biomolecule.

In some examples of the present system or methods described herein, an exemplary method for determining the 3-D atomic resolution structure of the biomolecule further comprises: generating a plurality of theoretical structural biomolecule 2-D models using the biomolecule sequence and one or more 2-D structure predicting algorithms; generating a plurality of theoretical structural biomolecule 3-D models using a 3-D structure predicting algorithm using the plurality of theoretical structural biomolecule 2-D models; generating a predicted chemical shift set for each of the plurality of theoretical structural biomolecule 3-D models;

comparing the predicted chemical shift set to the chemical shift(s) of the one or more atomic labels; and selecting a theoretical structural biomolecule 3-D model having the closest agreement between the respective predicted chemical shift set and the chemical shift(s) of the one or more atomic labels as the 3-D atomic resolution structure. In some embodiments, chemical shift data of the biomolecule can be gathered at spectrometer frequencies of 300 MHz or less, for example at about 20 MHz to about 100 MHz.

While the methods and systems described herein apply to polypeptides, proteins and polynucleotides, in some embodiments, the methods apply to the analysis of an isotopically labeled polynucleotide, for example, an isotopically labeled ribonucleic acid (RNA). In some of these embodiments, the biomolecule to be analyzed is labeled with one or more isotopic labels comprising: $^2$H, $^{13}$C, $^{15}$N, $^{19}$F or $^{31}$P.

Specific examples for determining the 2-D or a 3-D atomic resolution structure of a polynucleotide can include the steps: generating a plurality of theoretical structural polynucleotide 2-D models using the polynucleotide sequence and one or more 2-D structure predicting algorithms; generating a plurality of theoretical structural polynucleotide 3-D models using a 3-D structure predicting algorithm using the plurality of theoretical structural polynucleotide 2-D models; generating a predicted chemical shift set for each of the plurality of theoretical structural polynucleotide 3-D models; and comparing the predicted chemical shift set to the chemical shift(s) of the one or more atomic labels; and selecting a theoretical structural polynucleotide 3-D models having the closest agreement between the respective predicted chemical shift set and experimental chemical shifts indicative of the 3-D atomic resolution structure.

Specific examples for determining the 2-D or a 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid comprises the steps: generating a plurality of theoretical structural polynucleotide 2-D models using the polynucleotide sequence and one or more 2-D structure predicting algorithms; generating a plurality of theoretical structural polynucleotide 3-D models using a 3-D structure predicting algorithm using the plurality of theoretical structural polynucleotide 2-D models; generating a predicted chemical shift set for each of the plurality of theoretical structural polynucleotide 3-D models; and comparing the predicted chemical shift set to the chemical shift(s) of the one or more atomic labels of the polynucleotide when bound to or interacting with another molecule, for example a small molecule (e.g., molecules in Table 1), a protein, a ligand, an RNA, a DNA, a salt, an ion, an atom, a molecule, and/or any nucleic acid; and selecting a theoretical structural polynucleotide 3-D models having the closest agreement between the respective predicted chemical shift set and experimental chemical shifts indicative of the 3-D atomic resolution structure.

Specific examples for determining the 2-D or a 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid comprises the steps: generating a plurality of theoretical structural polynucleotide 2-D models using the polynucleotide sequence and one or more 2-D structure predicting algorithms; generating a plurality of theoretical structural polynucleotide 3-D models using a 3-D structure predicting algorithm using the plurality of theoretical structural polynucleotide 2-D models; generating a predicted chemical shift set for each of the plurality of theoretical structural polynucleotide 3-D models; filtering the experimental chemical shifts of the one or more atomic labels of the polynucleotide when bound to or interacting with another molecule, for example a small molecule (e.g., molecules in Table 1), a protein, a ligand, an RNA, a DNA, a salt, an ion, an atom, a molecule, and/or any nucleic acid such that chemical shifts that are perturbed by the electronic environment of the another molecule are not used; and comparing the predicted chemical shift set to the chemical shift(s) of the one or more atomic labels of the polynucleotide when bound to or interacting with another molecule, for example a small molecule (e.g., molecules in Table 1), a protein, a ligand, an RNA, a DNA, a salt, an ion, an atom, a molecule, and/or any nucleic acid; and selecting a theoretical structural polynucleotide 3-D models having the closest agreement between the respective predicted chemical shift set and experimental chemical shifts indicative of the 3-D atomic resolution structure.

In some of these exemplary methods and systems of the present invention, the predicted chemical shift set of the biomolecule, for example a polynucleotide are generated by comparing each theoretical structural polynucleotide 3-D model with a database comprising a relationship between experimental chemical shifts and experimentally determined 3-D polynucleotide structures. In one related embodiment, generating the predicted chemical shift set can include the steps: calculating a polynucleotide structural metric comprising atomic coordinates, stacking interactions, magnetic susceptibility, electromagnetic fields, or dihedral angles from one or more experimentally determined polynucleotide 3-D structures; using a regression algorithm to generate a set of mathematical functions or objects that describe relationships between experimental chemical shifts and the polynucleotide structural metric of the experimentally determined 3-D polynucleotide structures; calculating a polynucleotide structural metric for each of the theoretical structural polynucleotide 3-D models; inputting the polynucleotide structural metric for each of the theoretical structural polynucleotide 3-D models into the set of mathematical functions or objects to generate the predicted chemical shift set. Several examples of regression algorithms are described herein. In some embodiments, the method uses a Random Forest algorithm.

In some embodiment, an exemplary method routine using a low-field NMR device described herein as shown in FIG. 2 is as follows. In some embodiments, the user wishes to determine the 3-D structure of a 25 nucleotide TAR RNA and to map out its interaction with a protein molecule, the following steps may be performed: (1) Load a cartridge into the device containing a selectively labeled 25 nucleotide TAR RNA using one or more nuclei selected from: $^2$H, $^{13}$C, $^{15}$N, $^{19}$F, or $^{31}$P. (2) Use the user interface with a graphical user interface to select the application of interest. In one example, it is "3-D structure determination". (3) The instrument records NMR spectra of the 25 nucleotide TAR RNA. It will use the device to transport the sample from the sample storage device (e.g., a cartridge) into the NMR module. This may be a microfluidic device or the sample may be in a micro-cartridge that fits into the NMR probe. (4) An NMR spectra is recorded of the sample in an automated manner. This can include 1-D, 2-D, 3-D . . . N-D heteronuclear or homonuclear experiments involving $^1$H, $^{13}$C, $^{15}$N, and $^{31}$P nuclei. (5) The computer executes a peak picking software program from memory, memory module or a program storage medium, wherein the software program is then used to measure the individual proton, carbon, nitrogen and phosphorus chemical shifts for all selectively labeled polynucleotide samples measured or stored in a memory module. (6) RNA structures are predicted based on sequence using existing structure predicting algorithm (such as MC-Sym). (7) The $^1$H, $^{13}$C, $^{15}$N, and $^{31}$P chemical shifts are then predicted for each candidate predicted RNA structures using in-house software. (8) The agreement between the predicted and measured chemical shifts is then used to select a starting seed structure. (9) Optionally, the seed structure is subjected to further refinement rounds using an energy function that includes the difference between measured and computed chemical shifts. (10) Cross validation statistics is then used to rigorously assess the accuracy of the determined structure. (11) The instrument then outputs one or more structures that satisfies the chemical shifts within prediction/measurement error. (12) The analysis module then performs a binding analysis. (13) On the user interface (for example, a graphical user interface) user selects application "binding analysis" and selects the selectively labeled polynucleotide sample(s) on which he/she wishes to use to probe binding of the TAR to a protein molecule. (14) Device loads a protein sample into the device mixing chamber. (15) A microfluidic mixing device mixes the selectively labeled polynucleotide sample with the selected protein. (16) New RNA-protein sample is transferred to the NMR probe by the device. (17) The NMR module performs an NMR spectral analysis of the selectively labeled polynucleotide sample(s) containing the protein. (18) The chemical shifts are recorded on the selectively labeled polynucleotide sample(s) containing the protein and stored in the analysis module. (19) The analysis module calculates the difference between the TAR RNA chemical shifts measured in the absence or presence of the selected protein and is highlighted on the 3-D structure of the RNA on the GUI interface.

In some embodiment, an exemplary method routine using a low-field NMR device described herein as shown in FIG. 2 is as follows. In some embodiments, the user wishes to determine the 3-D structure of a 25 nucleotide TAR RNA and to map out its interaction with a protein molecule, the following steps may be performed: (1) Load a cartridge into the device containing a selectively labeled 25 nucleotide TAR RNA using one or more nuclei selected from: $^2$H, $^{13}$C, $^{15}$N, $^{19}$F, or $^{31}$P. Load a second cartridge into the device that contains one or more small molecules (e.g., one or more molecules listed in Table 1) such that at least a portion of the second cartridge is mixed with at least a portion of the first cartridge. (2) Use the user interface with a graphical user interface to select the application of interest. In one example, it is "3-D bound structure and binding pocket determination". (3) The instrument records NMR spectra of the 25 nucleotide TAR RNA bound to and/or interacting with the small molecule. It will use the device to transport the sample from the sample storage device (e.g., a cartridge) into the NMR module. This may be a microfluidic device or the sample may be in a micro-cartridge that fits into the NMR probe. (4) An NMR spectra is recorded of the sample in an automated manner. This can include 1-D, 2-D, 3-D . . . N-D heteronuclear or homonuclear experiments involving $^1$H, $^3$C, $^{11}$N, and $^{31}$P nuclei. (5) The computer executes a peak picking software program from memory, memory module or a program storage medium, wherein the software program is then used to measure the individual proton, carbon, nitrogen and phosphorus chemical shifts for all selectively labeled polynucleotide samples measured or stored in a memory module. (6) RNA structures are predicted based on sequence using existing structure predicting algorithm (such as MC-Sym). (7) The $^1$H, $^{13}$C, $^{11}$N, and $^{31}$P chemical shifts are then predicted for each candidate predicted RNA structures using in-house software. (8) Chemical shifts are optionally filtered based on whether the chemical shift is perturbed by the electronic environment of the small molecule, and the agreement between the predicted and measured chemical shifts is then used to select a starting seed structure. (9) Optionally, the seed structure is subjected to further refinement rounds using an energy function that includes the difference between measured and computed chemical shifts. (10) Cross validation statistics is then used to rigorously assess the accuracy of the determined structure. (11) The instrument then outputs one or more structures that satisfies the chemical shifts within prediction/measurement error. (12) The instrument and/or another computer then probes the TAR structure for a binding pocket, wherein the probing is conducted using a binding pocket identification software (e.g., rDcavity, fpocket, ICM pocketfinder, Schrodinger's SiteMap).

In some embodiments, the present invention provides a method for determining the 3-D atomic resolution structure of a polynucleotide, once the polynucleotide in the analysis volume has been interrogated using NMR. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:

a. generating a plurality of theoretical structural polynucleotide 2-D models using the nucleotide sequence and one or more 2-D structure predicting algorithms and/or inputting a known or assumed polynucleotide 2-D;

b. generating a plurality of theoretical structural polynucleotide 3-D models using a 3-D structure predicting algorithm using the one or more of the plurality of theoretical and/or known and/or assumed structural polynucleotide 2-D models;

c. generating a predicted chemical shift set for each theoretical structural polynucleotide 3-D models;

d. comparing the predicted chemical shift set to the chemical shift(s) of the one or more atomic labels; and e. selecting a theoretical structural polynucleotide 3-D model having the closest agreement between the respective predicted chemical shift set and the chemical shift(s) of the one or more atomic labels as the 3-D atomic resolution structure.

In some embodiments, the present invention provides a method for determining the 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:

a. generating a plurality of theoretical structural polynucleotide 2-D models using the nucleotide sequence and one or more 2-D structure predicting algorithms and/or inputting a known or assumed polynucleotide 2-D;
b. generating a plurality of theoretical structural polynucleotide 3-D models using a 3-D structure predicting algorithm using the one or more of the plurality of theoretical and/or known and/or assumed structural polynucleotide 2-D models;
c. generating a predicted chemical shift set for each of the plurality of theoretical structural polynucleotide 3-D models;
d. comparing the predicted chemical shift set to the chemical shift(s) of the one or more atomic labels;
e. selecting a theoretical structural polynucleotide 3-D model having the closest agreement between the respective predicted chemical shift set and the chemical shift(s) of the one or more atomic labels as the 3-D atomic resolution structure; and
f. Identifying one or more small molecule binding pockets on the 3-D structure, using binding pocket identification software, for example, rDcavity, fpocket, ICM pocketfinder, and/or Schrodinger's SiteMap.

In some embodiments, the present invention provides a method for determining the 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid, once the polynucleotide in the analysis volume has been interrogated using NMR. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:

a. generating a plurality of theoretical structural polynucleotide 2-D models using the nucleotide sequence and one or more 2-D structure predicting algorithms and/or inputting a known or assumed polynucleotide 2-D;
b. generating a plurality of theoretical structural polynucleotide 3-D models using a 3-D structure predicting algorithm using the one or more of the plurality of theoretical and/or known and/or assumed structural polynucleotide 2-D models;
c. generating a predicted chemical shift set for each of the plurality of theoretical structural polynucleotide 3-D models;
d. comparing the predicted chemical shift set to the chemical shift(s) of the one or more atomic labels;
e. selecting a theoretical structural polynucleotide 3-D model having the closest agreement between the respective predicted chemical shift set and the chemical shift(s) of the one or more atomic labels as the 3-D atomic resolution structure;
f. Identifying one or more binding pockets on the 3-D structure, using binding pocket identification software, for example, rDcavity, fpocket, ICM pocketfinder, and/or Schrodinger's SiteMap;
g. Docking to the one or more binding pockets identified in the polynucleotide 3-D structure the another molecule using a docking software, for example ICM, Schrodinger's Glide, rDock, MOE etc.;
h. Refining the docked binding pocket and the corresponding polynucleotide 3-D structure by inputting the docked polynucleotide 3-D structure into a modeling software comprising one or more of molecular dynamics software (e.g., NAMD, GROMACS, AMBER, CHARMM), quantum mechanical software (e.g., GAUSSIAN, GAMES), molecular mechanics software (e.g., TINKER), RNA modeling software (e.g., FARNA, ROSETTA, MC-Sym, 3D-RNA).

In some embodiments, refining comprises energy minimization and/or a molecular dynamics simulation. In some embodiments, a plurality of 3-D structure selected by comparing the respective predicted chemical shift set and the chemical shift(s) of the one or more atomic labels as the 3-D atomic resolution structures, wherein one or more of the plurality of the selected 3-D structures are not in the closest agreement of the respective predicted chemical shift set and the chemical shift(s) of the one or more atomic labels as the 3-D atomic resolution structure. In various embodiments, when a plurality of 3-D structure are selected, one or more of the plurality of 3-D structures are input into steps (g) and/or (h). In various embodiments, when one or more of the plurality of structures are input into steps (g) and/or (h), one or more of the structures are selected as the "bound-structure" based on, for example, an energy, a score, a subjective metric, and/or any other structure and/or energy-related metric.

In some embodiments, the present invention provides a method for determining the 3-D atomic resolution structure of a polynucleotide bound to another molecule, for example a small molecule (e.g., molecules in Table 1), a protein, a ligand, an RNA, a DNA, a salt, an ion, an atom, a molecule, and/or any nucleic acid, once the polynucleotide in the analysis volume has been interrogated using NMR. In some embodiments, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:

a. generating a plurality of theoretical structural polynucleotide 2-D models using the nucleotide sequence and one or more 2-D structure predicting algorithms and/or inputting a known or assumed polynucleotide 2-D;
b. generating a plurality of theoretical structural polynucleotide 3-D models using a 3-D structure predicting algorithm using the one or more of the plurality of theoretical and/or known and/or assumed structural polynucleotide 2-D models;
c. generating a predicted chemical shift set for each of the plurality of theoretical structural polynucleotide 3-D models;
d. comparing the predicted chemical shift set to the chemical shift(s) of the one or more atomic labels;
e. selecting a theoretical structural polynucleotide 3-D model having the closest agreement between the respective predicted chemical shift set and the chemical shift(s) of the one or more atomic labels as the 3-D atomic resolution structure;
f. Identifying one or more binding pockets on the 3-D structure, using binding pocket identification software, for example, rDcavity, fpocket, ICM pocketfinder, and/or Schrodinger's SiteMap;

g. Associating to the one or more binding pockets identified in the polynucleotide 3-D structure the another molecule using, for example a software, for example ICM, Schrodinger's Glide, rDock, MOE etc.;

h. Refining the docked binding pocket and the corresponding polynucleotide 3-D structure by inputting the docked polynucleotide 3-D structure into a modeling software comprising one or more of molecular dynamics software (e.g., NAMD, GROMACS, AMBER, CHARMM), quantum mechanical software (e.g., GAUSSIAN, GAMES), molecular mechanics software (e.g., TINKER), RNA modeling software (e.g., FARNA, ROSETTA, MC-Sym, 3D-RNA); and i. Identifying the refined binding pocket of the corresponding polynucleotide 3-D structure.

In some embodiments, refining comprises energy minimization and/or a molecular dynamics simulation. In some embodiments, a plurality of 3-D structure selected by comparing the respective predicted chemical shift set and the chemical shift(s) of the one or more atomic labels as the 3-D atomic resolution structures, wherein one or more of the plurality of the selected 3-D structures are not in the closest agreement of the respective predicted chemical shift set and the chemical shift(s) of the one or more atomic labels as the 3-D atomic resolution structure. In various embodiments, when a plurality of 3-D structure are selected, one or more of the plurality of 3-D structures are input into steps (g) and/or (h) and/or (i). In various embodiments, when one or more of the plurality of structures are input into steps (g) and/or (h) and/or (i), one or more of the structures are selected as the "bound-structure" based on, for example, an energy, a score, a subjective metric, and/or any other structure and/or energy-related metric.

In various embodiments, associating to the one or more binding pockets identified in the polynucleotide 3-D structure comprises computational docking methods, molecular modeling methods, experimentally-informed methods or any method that places the another molecule in the binding pocket.

In various embodiments, identifying the refined binding pocket of the corresponding polynucleotide 3-D structure comprises one or more of: (1) using the coordinates of the another molecule to define an approximate binding pocket, and/or (2) identifying the binding pocket on the 3-D structure, using binding pocket identification software, for example, rDcavity, fpocket, ICM pocketfinder, and/or Schrodinger's SiteMap. In some embodiments, when the coordinates of the another molecule are used to define an approximate binding pocket, each atom, for example a heavy atom and/or any atom, and a radius therefrom are used to define the maximum boundary of the binding pocket. In various embodiments, the radius comprises about 0.1 angstroms, about 0.2 angstroms, about 0.3 angstroms, about 0.4 angstroms, about 0.5 angstroms, about 0.6 angstroms, about 0.7 angstroms, about 0.8 angstroms, about 0.9 angstroms, about 1 angstroms, about 2 angstroms, about 3 angstroms, about 4 angstroms, about 5 angstroms, about 6 angstroms, about 7 angstroms, about 8 angstroms, about 9 angstroms, about 10 angstroms, or any combination thereof.

Application to Provide Access to Binding Pockets and/or Structures

In various embodiments, one or more polynucleotide 2-D structures and/or models, 3-D structures and/or models, and/or binding pockets are provided using a computer-based application. In some embodiments, a computer-based application comprises a web-application, a standalone application, a cloud-based application or any software generated application. In various embodiments, the application comprises a graphical interface that provides visual and virtual access to the one or more polynucleotide 2-D structures and/or models, 3-D structures and/or models, and/or binding pockets.

In some embodiments, the software-based application interfaces with another application. For example, in some embodiments, the software-based application interfaces with Schrodinger's software, MOE software, Molsoft LLC software, Biovia software, Knime software or any combination thereof. In another non-limiting example, the software-based application interfaces with molecular modeling software, for example Schrodinger's software, MOE software, Molsoft LLC software, Amber, CHARMM, GROMACS, GAMESS, GAUSSIAN, NAMD and/or any other modeling software. In some embodiments, the software-based application comprises any one or more of the embodiments described in the instant application.

Application Programming Interface and Graphical User Interface

In some embodiments, the platforms, systems, methods and computer readable media comprise an application programming interface, the application programming interface providing access to the environmental data. In some embodiments the application programming interface interacts with the server using data query language. In some embodiments the application programming interface comprises data query language. In some embodiments, the application programming interface provides access to the raw sensor data or cleaned data. In some embodiments, the application programming interface provides access to the pre-analytic data. In some embodiments, the application programming interface provides access to the analytic data. In some embodiments, a device comprising a processor configured to provide an application, comprising a software module configured to use the API provides access one or more of the environmental data, the raw sensor data or cleaned data, the pre-analytic data, the analytic data, and/or the environmental data report. In some embodiments, the application comprises a web application, software application, and/or mobile application or applet.

In some embodiments, the platforms, systems, methods and computer readable media further comprises a graphical user interface, the graphical user interface provides access to the environmental data. In some embodiments, the application programming interface provides access to the raw sensor data or cleaned data. In some embodiments, the graphical user interface providing access to the pre-analytic data. In some embodiments, the platform further comprises a graphical user interface, the graphical user interface providing access to the analytic data. In some embodiments, a device comprising a processor configured to provide an application comprising a software module configured to display a graphical user interface provides access to one or more of the environmental data, the raw sensor data or the cleaned data, the pre-analytic data, the analytic data, and/or the environmental data report. In some embodiments the graphical user interface is displayed as a standalone application or as an extension to an existing application. In some embodiments, the graphical user interface is a web application. In some embodiments, the graphical user interface is a pop-up window and/or an overlay. In some embodiments, the graphical user interface is a website. In some embodiments the graphical user interface is a mobile application.

Digital Processing Device

In some embodiments, the platforms, systems, media, and methods described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art. In some embodiments, the digital processing devices is a computational device, an external and/or any other device described herein.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®., and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Server Configuration

In some embodiments, a suitable server configuration includes 1, 2, 3, 4, 5, 6, 7, 8, 9, 10, 20, 30, 40, 50, 60, 70, 80, 90, 100, 200, 500, 1000 or more servers, one or more server farms, and cloud-based server resource allocation systems. In some embodiments, the servers are co-located. In some embodiments, the servers are located in different geographical locations. In some embodiments the servers are housed in the same rack. In some embodiments, the servers are housed in multiple racks. In some embodiments, the multiple racks are in the same geographic region. In some embodiments the racks are in different geographic regions. In some embodiments, the server is or a plurality of servers employ a software framework such as Hadoop, Google MapReduce, HBase, and/or Hive, for storage and large-scale processing of data-sets on clusters of hardware.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web applications software framework such as Hadoop, Google MapReduce, HBase, and/or Hive, for storage and/or large-scale processing of data-sets on clusters of hardware is employed. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverligh®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Swift, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, Google Play, Black-Berry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, Swift, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of clinical trial, profile, and/or molecular phenotype information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices. Persons of ordinary skill in the art will recognize that the methods, platforms, systems and media described herein, in some embodiments, require big data storage and analysis platforms.

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

EXAMPLES

Non-limiting exemplary embodiments of the subject matter described herein are described below with reference to the drawings.

Example 1

Structure Determination of an Apical Loop Sequence of Human Pre-miR 122 RNA

The apical loop sequence of human pre-miR 122 RNA sequence was investigated as an example. Two base pairs at the 5'- and 3'-ends of the sequence were modified from the native pre-miR 122 sequence in order to stabilize the 24-mer stem loop construct for NMR studies (5'-GGCUUGUGUCUAAACUAUCAAGCC-3') (SEQ ID NO: 2).

The secondary structures predicted by the software program MFold suggest the possibility of a long stretch (up to 12 bases) of an apical loop which combined together with redundant adenine bases in the loop sequence prohibits conventional sequential assignment using uniformly non-selectively labeled RNA sample and thus requires selective labeling for unambiguous resonance assignment and 3-D structure determination. Four RNA oligonucleotides sequences are designed for selective labeling. Each has two selectively 13C/15N isotope labeled residues. Labeling a pair of purine (A or G) and pyrimidine (C or U) in a single oligonucleotides reduces the number of samples by half and minimize potential spectral overlap between two labeled residues since two purines or two pyrimidines are more likely to overlap.

```
(i)
                                       (SEQ ID NO: 2)
5'-GGCUUGUGUCUAAACUAUCAAGCC-3' (U11/A12)

(ii)
                                       (SEQ ID NO: 2)
5'-GGCUUGUGUCUAAACUAUCAAGCC-3' (C10/A13)

(iii)
                                       (SEQ ID NO: 2)
5'-GGCUUGUGUCUAAACUAUCAAGCC-3' (A14/C15)

(iv)
                                       (SEQ ID NO: 2)
5'-GGCUUGUGUCUAAACUAUCAAGCC-3' (U16/A17)
```

The $^{13}C/^{15}N$ labeled 2'-ACE@ phosphoramidites (rA, rG, rC, rU) for chemical synthesis were prepared by Dharmacon from individual $^{13}C/^{15}N$ labeled ribonucleosides (Chembridge Isotope Laboratories). Uniformly $^{13}C/^{15}N$ labeled apical loop construct of the human pre-miR 122 (5'-GGC-UUGUGUCUAAACUAUCAAGCC-3') (SEQ ID NO: 2) sequence was prepared by T7 in vitro RNA transcription using $^{13}C/^{15}N$ labeled rNTPs (Chembridge Isotope Laboratories) and purified by polyacrylamide gel electrophoresis (PAGE). Four selectively $^{13}C/^{15}N$ isotopes labeled RNA oligonucleotides (U11/A12, C10/A13, A14/C15, and U16A17) were chemically synthesized and PAGE purified by Dharmacon.

Samples of 200 μL volume were contained in a Shigemi NMR tube for NMR experiments.

Samples were dissolved in 200 μL of aqueous buffer of 15 mM phosphate, 25 mM NaCl, 0.1 mM EDTA, 90% $H_2O$/10% $D_2O$. Final RNA concentrations were 0.1-0.3 mM. 10% $D_2O$ was added for locking and 10 μM DSS (4,4-dimethyl-4-silapentane-1-sulfonic acid) was added as internal chemical shift reference. The 1H signal of DSS was referenced to 0 ppm.

All NMR data were collected with an 600 MHz Agilent NMR spectrometer equipped with a HCN-triple resonance/z-gradient PFG probe at 4-30° C.

For the uniformly labeled polynucleotide sample, the assignment of the exchangeable imino proton and nitrogen resonances, 2D $^{15}$N-$^1$H HSQC (sweep width (Hz)=13020(H)×1215(N); complex data points=1024(H)×38(N); carrier frequency=water(H), 154 ppm(N)) and 2D $^1$H-$^1$H NOESY (sweep width (Hz)=13020(H)×13020(H); complex data points=1024×256; carrier frequency=water; NOE mixing time of 200, 300 msec) were acquired at 4° C. and 10° C. For assignment of the non-exchangeable aromatic and ribose proton and carbon resonances, 2D $^{13}$C-$^1$H HSQC(aromatic) (sweep width (Hz)=4808(H)×1734(C); complex data points=385×110; carrier frequency=water(H), 140.5 ppm (C)), 2D $^{13}$C-$^1$H HSQC(ribose) (sweep width (Hz)=4808(H)×2715(C); complex data points=385×170; carrier frequency=water(H), 98 ppm(C)), 2D HCN(aromatic) (sweep width(Hz)=4808(H)×1823(N); complex data points=385(H)×64(N); carrier frequency=water(H), 140.5 ppm(C), 158 ppm(N)), 2D HCN(ribose) (sweep width(Hz)=4808(H)×1823(N); complex data points=385(H)×64(N); carrier frequency=water(H), 98 ppm(C), 158 ppm(N)), and 3-D NOESY-13C-HSQC(ribose) (sweep width(Hz)=4807(H)×3000(H)×2413(C); complex data points=385(H)×34(H)×40(C); carrier frequency=water(H), 6 ppm(H), 98 ppm (C); NOE mixing time of 250 and 350 msec), 3-D NOESY-$^{13}$C-HSQC(aromatic) (sweep width(Hz)=4807(H)×3000(H)×1734(C); complex data points=385(H)×46(H)×28(C); carrier frequency=water(H), 6 ppm(H), 140 ppm(C); NOE mixing time of 200, 250 and 350 msec) were acquired at 20° C., 25° C. and 35° C.

For selectively labeled samples, a 2D $^{13}$C-$^1$H HSQC (aromatic) (sweep width (Hz)=4808(H)×3620(C); complex data points=385×64; carrier frequency=water(H), 146 ppm (C)), 2D $^{13}$C-1H HSQC(ribose) (sweep width (Hz)=2404(H)×3318(C); complex data points=194×60; carrier frequency=water(H), 98 ppm(C)), 2D HCN(aromatic) (sweep width(Hz)=4808(H)×2000(N); complex data points=385(H)×32(N); carrier frequency=water(H), 140.5 ppm(C), 158 ppm(N)), and 2D HCN(ribose) (sweep width (Hz)=4808(H)×2000(N); complex data points=385(H)×32(N); carrier frequency=water(H), 98 ppm(C), 158 ppm(N)) were acquired at 25° C.

All acquired NMR data were converted and processed by NMRPipe software available at (http://spin.niddk.nih.gov/NMRPipe/). Briefly, for each dimension, the converted FID was apodized by shifted cosine or Gaussian, zero-filled to double the size of acquired data points, Fourier transformed and phase corrected, and baseline adjusted. Processed 2-D and 3-D spectra were analyzed by Sparky software application version 3.113 available at (http://www.cgl.ucsf.edu/home/sparky/). Center of peak position (chemical shift) and volume of peak were obtained by numerical fitting of the processed peak shape to an analytical Gaussian function.

Chemical shift-Structure Database. A chemical shift-structure relation database was populated with experimental data of three dimensional atomic coordinates and chemical shifts taken from 18 RNA systems deposited in both PDB (Protein Data Bank; http://www.rcsb.org) and BMRB (Biological Magnetic Resonance Bank; http://www.bmrb.wisc.edu) (1LDZ(4226), 1YSV(6485), 1R7 W(6076), 1KKA (5259), 1KKA(5256), 2JTP(15417), 1Z2J(6543), 1OW9 (5852), 1PJY(5834), 1NC0(5655), 1LC6(5371), 1R7Z (6077), 2KOC(5705), 2K41(15781), 2GM0(7098), 2K3Z (15780), 2JXS(15572), 2JXQ(15571); in each of 18 systems PDB identifier is followed by BMRB identifier in parenthesis). Prior to the calculation of the structure features, the average structure of the NMR ensemble was calculated and then energy minimized using the AMBER ff99XOL force field. Next, a set of features were selected to describe the local structure around a probe nucleus. Specifically, the local environment around a nucleus was described by feature vectors whose elements consist of the dihedrals of the residue on which a nucleus resides ($\alpha,\beta,\gamma,\delta,\in,\zeta,v0,v1,v2,v3,v4$) and three binary descriptors indicating whether the residue is base-paired, stacked with the preceding residue in the sequence or stacked with the succeeding resides in the sequence. The combined feature vectors, together with measured chemical shifts, the identity of the carbon nucleus and associated residue name, comprised the completed chemical shift-structure relation database.

Generating Chemical Shift Predictor. Taking the complete chemical shift-structure relation database as input, the chemical shift predictors were generated using a machine learning approach. In particular, the random forest approach was used to generate individual C1', C2', C3', C4', C5', C2, C5, C6, C8, H1', H2', H3', H4', H5', H5'', H2, H5, H6 and H8 chemical shift predictors. The random forest method was used as included in the random Forest library in the R statistical software package (http://www.r-project.org). Using the default settings in the random Forest package, the random forest approach was used to get a forest of "decision" trees that relate chemical shifts values to the value of the structure features in the database. Each predictor was trained using 1000 randomly constructed decision trees.

Generating Dihedral Angle Predictor. Individual $\alpha,\beta,\gamma,\delta,\in,\zeta,v0,v1,v2,v3$ and $v4$ dihedral angle predictors were generated in a similar fashion. In this case, the forest of "decision" trees relate dihedral values to chemical shifts.

Figure 7:
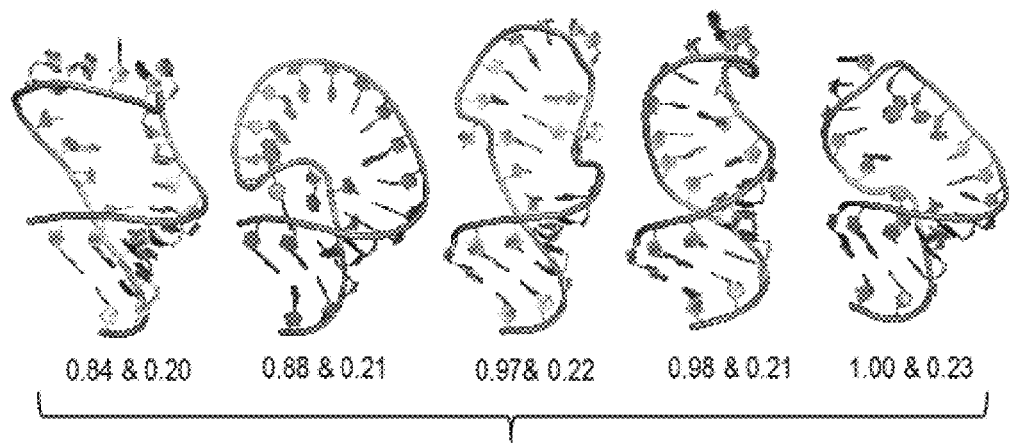
FIG. 7 shows exemplary schematic representations of the output of structural models of human pre-miR 122 apical loop RNA that were obtained by modeling the structures against experimental chemical shift data. The numbers below each model indicate the 13C and 1H chemical shift RMSD between measured chemical shift versus predicted chemical shift using the methods in accordance with the teachings of the present disclosure.

A seed structure of the apical loop of the human pre-miR 122 RNA sequence was generated using the following approach. First, the secondary structure was predicted from the primary structure (5'-GGCUUGUGUCUAAACUAU-CAAGCC-3') (SEQ ID NO: 2) using the software application MC-FOLD (http://www.major.iric.ca/MC-Fold/). Based on the secondary structure, hydrogen-bonding constraints were generated. Second, all dihedral angles were predicted using the chemical shift based dihedral angle predictors described above. The input for the predictors was the experimentally measured chemical shifts. The outputted predicted dihedrals were combined with the hydrogen-bonding constraint to generate 10 preliminary structural models using the software application XPLOR-NIH available at (http://nmr.cit.nih.gov/xplor-nih/). The standard simulated annealing protocol was used to generate the initial structural models. Each of the models was then further refined using restraint MD protocol in the software application NAMD available at: (http://www.ks.uiuc.edu/Research/namd/). In these simulations, MD simulations were carried out using the AMBER ff99XOL force field combined with the GBSA implicit solvent model. Restraints were setup to maintain and enforce the predicted hydrogen bonding and predicted dihedral angles over the course of the simulations. For each, 1ns constant temperature simulation was carried out at 300 K. The results of the structure determination of the human pre-miR 122 RNA sequence are shown in FIG. 7. FIG. 7 illustrates 5 outputted structural models of the human pre-miR 122 apical loop RNA using the methods of the present invention. Shown in FIG. 7 are cartoon representations of the five structural models that best agree with the experimental chemical shift data obtained. Below each, is the $^{13}$C and $^1$H chemical shift RMSD between measured and predicted.

For each restrained MD trajectory, the conformation that best satisfied the restraints were selected and then energy minimized. Using the chemical shift predictors described above, $^{13}$C and $^1$H chemical shifts were then back-calculated from each model. The RMSD (root-mean-square-deviation) between the measured and predicted chemical shifts were then calculated and top 5 structures were selected.

Example 2

Methods of Using $^1$H NMR Chemical Shifts in Determining RNA Structure and Dynamics Methods and Materials Predicting RNA $^1$H Chemical Shifts. A panel of 18 RNA structures (1ZC5, 2KOC, 1Z2J, 1XHP, 2QH2, 2KYD, 1JU7, 2JTP, 2FDT, 1N8X, 2L3E, 1LW, 2JYM, 2L5Z, 1NC0, 1IDV, 2L1V, 1OW9) was used to evaluate $^1$H chemical shift predictions using SHIFT and NUCHEMICS. This panel represents RNA structures that have been determined by NMR following the introduction of SHIFTS and NUCHEMICS (2002-2011) for which $^1$H chemical shift assignments were also available in the Biological Magnetic Resonance Bank (BMRB)29 (http://www.bmrb.wisc.edu/). Four additional structures (2QH3, 2QH4, 1YMO, 2JWV) were not included due to undocumented or incomplete chemical shift referencing. However, including these structures had little to no impact on the results presented here.

Molecular dynamics (MD) simulations. MD simulations of an RNA duplex (PBID:2KYD)30, UUCG tetra-loop (PBID:2KOC)31, and pre-quenosine-1 (preQ1) riboswitch (PDBID:2LV1)32 were performed at 300 K and 500 K trajectories using GROMACS 4.5.133 and the AMER9434 nucleic acid force field. Structures were subjected to 100 steps of steepest descent minimization and subsequently solvated with TIP3 water35 in a triclinical box and charge neutralized using sodium counterions. Harmonic constraints with a force constant of 1000 kJ mol-1 nm-2 were placed on the heavy atoms and simulated at 300 K for 1.4 ns. The harmonic constraints were then gradually released over 200 ps. Starting from the equilibrated coordinates two 4 ns trajectories were generated at 300 K and 500 K, respectively. Coordinates were saved every 2 ps.

Replica-exchange molecular dynamics (REMD) simulations were used to generate a broad conformational pool for the human HIV-1 TAR apical loop (shown above in Example 1) from which sets of non-overlapping reference ensembles could be constructed. Initial coordinates were obtained using Rosetta FARNA37, a de novo structure determination software program for nucleic acids. Starting from the primary sequence, UAUCGAGCCUGGGAGCUCGAUA (SEQ ID NO: 3), 1000 candidate structures were generated applying base pairing constraints between residues U1 and A22, A2 and U21, U3 and A20, C4 and G19, G5 and C18, A6 and U17, G7 and C16, and C8 and G15. The conformation with the lowest energy was used as the initial coordinates for the REMD simulations. The initial structure was subjected to 100 steps of steepest descent minimization and then solvated with TIP3 water in an octahedron box and charge neutralized using sodium counterions. Harmonic constraints with a force constant of 1000 kJ mol$^{-1}$ nm$^{-2}$ were placed on the heavy atoms and simulated at 300 K for 1.4 ns. The harmonic constraints were then gradually released over 200 ps. Starting from the equilibrated coordinates at 300 K, 15 additional replicas of apical loop were prepared by slowing heating the system to 303, 306, 309, 312, 315, 319, 322, 325, 329, 332, 335, 339, 342, 346 and 350 K. REMD simulations were then initiated from these 16 replicas. Exchanges where attempted every 2 ps and coordinates were saved every 2 ps. Production trajectories 45 ns in length were generated. The 45,000 conformations were used as the representative conformation pool for the TAR apical loop.

Selecting Ensembles. Ensembles were constructed using chemical shifts, residual dipolar coupling (RDC) and chemical shift+RDCs data using the sample and select (SAS) approach. The ensembles were selected by minimizing the cost function, $$\chi^2 = K_{CS}\chi^2_{CS} + K_{RDC}\chi^2_{RDC}$$

where $$\chi^2_{CS} = \frac{1}{L_{CS}}\sum_{i=1}^{N}\left(\delta_i^{pred} - \delta_i^{meas}\right)^2$$

and $$\chi^2_{CS} = \frac{1}{L_{RDC}}\sum_{ij=1}^{N}\left(D_{ij}^{pred} - D_{ij}^{meas}\right)^2$$

and the structure was subjected to 100 steps of steepest descent minimization and then solvated with TIP3 water35 in an octahedron box and charge neutralized using sodium counterions. Harmonic constraints with a force constant of 1000 kJ mol-1 nm-2 were placed on the heavy atoms and simulated at 300 K for 1.4 ns. The harmonic constraints were then gradually released over 200 ps. Starting from the equilibrated coordinates at 300 K, 15 additional replicas of apical loop were prepared by slowing heating the system to 303, 306, 309, 312, 315, 319, 322, 325, 329, 332, 335, 339, 342, 346 and 350 K. REMD simulations were then initiated from these 16 replicas. Exchanges where attempted every 2 ps and coordinates were saved every 2 ps. Production trajectories 45 ns in length were generated. The 45,000 conformations were used as the representative conformation pool for the HIV TAR apical loop.

Selecting Ensembles. Ensembles were constructed using chemical shifts, residual dipolar coupling (RDC) and chemical shift+RDCs data using the sample and select (SAS) approach. The ensembles were selected by minimizing the cost function, $$\chi^2 = K_{CS}\chi^2_{CS} + K_{RDC}\chi^2_{RDC}$$

where $$\chi^2_{CS} = \frac{1}{L_{CS}}\sum_{i=1}^{N}\left(\delta_i^{pred} - \delta_i^{meas}\right)^2$$

and $$\chi^2_{CS} = \frac{1}{L_{RDC}}\sum_{ij=1}^{N}\left(D_{ij}^{pred} - D_{ij}^{meas}\right)^2$$

Here, $\chi^2$ is the total cost function to be minimized; $\chi^2_{CS}$ and $\chi^2_{RDC}$ are the chemical shift and RDC components of x, respectively; $K_{CS}$ and $K_{RDC}$ are coefficients that determine the contribution of each component to $\chi 2$; $\delta_{pred}$ and $\delta_{meas}$ are the predicted and measured chemical shifts, respectively, and $D_{ij}^{pred}$ ad a $D_{ij}^{meas}$ are the predicted and measured RDCs, respectively; $L_{CS}$ and $L_{RDC}$ are the total number of chemical shift and RDC data, respectively. For selections using chemical shifts only, $K_{CS}$=1 and $K_{RDC}$=0. For selection using RDCs only, $K_{CS}$=0 and $K_{RDC}$=1. For selections carried out using a combination of chemical shift and RDCs, $K_{CS}$ was varied until $\chi^2_{CS}$ and $\chi^2_{RDC}$ were near specified thresholds while $K_{RDC}=1$. Each selection cycle was initiated from N randomly selected conformers. A Monte Carlo (MC) simulated annealing scheme was then used to minimize Eq. 3. Simulations were initiated at a high-effective temperature, where the MC acceptance probability was high (0.99), and slowly decreased until the MC acceptance probability was $10^{-5}$. At a given effective temperature 105 MC steps were carried out. The effective temperature was then decreased, with $T_{(i+1)}=0.92$ Ti.

Generating HIV TAR apical reference ensembles: The ensemble were constructed when setting N=1, 2, 4, 6 and 8. At each N value multiple selection cycles were carried out and then all conformers pooled. For N=2, 4, 6 and 8 ensembles, 80, 40, 26 and 20 selection cycles were carried out so as to ensure that the total number of conformers selected were approximately equal. To generate synthetic 'experimental' datasets, $^1$H chemical shifts were then calculated from the reference ensembles using SHIFTS. To simulate the presence errors in the dataset when carrying out chemical shift based selections, $^1$H chemical shifts were calculated for pool conformers using NUCHEMICS; for the set of 18 benchmark RNAs studied here the mean square-difference (RMSD) between SHIFTS and NUCHEMICS chemical shifts ~0.24 ppm, which is comparable to the uncertainty in NUCHEMICS predictions (~0.30 ppm; see below). Using SHIFTS chemical shifts to generate the reference datasets and then NUCHEMICS chemical shifts to select ensembles therefore effectively simulates the presence ~0.24 ppm error in predictions. This approach to simulate the presence of errors in theoretical simulations is similar to that used by Vendruscolo and coworkers in their study validating the use of chemical shifts to characterize the dynamical ensemble of the protein RNase A.

Comparing Ensembles. To examine how well the generated ensembles reproduce the target reference ensembles, as S-matrix method was employed. In this approach one directly compares the distributions of the two ensembles. Specifically, the matrix was defined as $S=\{s_{ij}\}$, where $$s_{ij}=|\rho_r^{ij}-\rho_t^{ij}|$$

and $\rho_r^{ij}$ and $\rho_r^{ij}$ are the normalized distribution of the inter atomic distance between atoms i and j. $s_{ij}$ ranges between 0 and 2 and is 0 if and only if $\rho_r^{ij}=\rho_t^{ij}$. We constructed S-matrices using the C1' atoms and utilized a bin-size of 0.5 Å to discretize $\rho^{ij}$. Ensemble were compared on the basis of the average $s_{ij}=\langle s_{ij}\rangle_A$.

Accuracy of $^1$H RNA chemical shift predictions. The accuracy was first examined with which RNA $^1$H chemical shifts can be predicted using SHIFTS and NUCEHMICS based on an RNA structure. We note that to our knowledge, SHIFTS $^1$H chemical shift predictions have never been evaluated for RNA. For these benchmark studies, a panel of 18 RNA structures determined by NMR was used for which 1H chemical shift assignments (H1', H2, H5, H6 and H8) are available at the Biological Magnetic Resonance Bank (www.bmrb.wisc.edu/). This data set represents RNAs for which $^1$H chemical shifts and NMR structures were deposited in the BMRB and PDB respectively following the introduction of SHIFTS and NUCHEMICS. Thus, they were not used in the developmental of SHIFTS and NUCHEMICS. In all cases, the 1H chemical shifts were not used as constraints in RNA structure determination. An additional four data sets were excluded due to undocumented or incomplete chemical shift referencing (note however that including those data sets had little impact on the overall results but generally led to deterioration in the chemical shift predictions). RNAs with modified bases were excluded because they cannot be handled by either SHIFTS or NUCHEMICS.

SHIFTS and NUCHEMICS were used to compute $^1$H chemical shifts based on the NMR structure for our panel of 18 RNA structures. These structures are mainly stem-loop RNAs containing a diverse set of apical loops, ranging from four to twelve bases in size, and internal bulges of varying sequence and type. Most structures contain either single or multiple non-canonical base-pairs, and the set contains one pseudoknot riboswitch structure. The $^1$H chemical shifts were computed for every conformer in the NMR bundle. We then computed the root mean-square-difference (RMSD) between the measured and predicted chemical shifts ($CS^{RMSD}$) for each conformer. The lowest $CS^{RMSD}$ values obtained over the bundle of NMR conformers for each RNA structure were examined. SHIFTS and NUCHEMICS reproduce the observed H1', H2, H5, H6, H8 chemical shifts with an $CS^{RMSD}$ over all 18 structures of 0.32, 0.38, 0.28, 0.31 and 0.37 ppm and 0.29, 0.41, 0.30, 0.27 and 0.31 ppm, respectively and with an overall $CS^{RMSD}$ of 0.35 and 0.34 ppm respectively. These values compare reasonably well with the agreement reported originally for SHIFTS (0.28 ppm) and NUCHEMICS (0.16 ppm). These predictions also compare favorably with $^1$H chemical shift predictions in proteins (typically range between 0.15-0.6 ppm).

In addition to limitations in the $^1$H chemical shift predictions, the agreement between measured and predicted $^1$H chemical shifts could be affected by uncertainties in the NMR structure. While the three structures (PDBID: 2KOC, 2FDT, 1XHP) that yield the best agreement using NUCHEMICS ($CS^{RMSD}=0.19$, 0.19 and 0.21 ppm respectively) also have the largest numbers of RDCs constraints per residue (~2.2 as compared to ~0.91 across all structures), a similar trend is not observed for SHIFTS. However, the overall $CS^{RMSD}$ did decrease from 0.35 to 0.32 ppm and from 0.34 to 0.27 ppm for SHIFTS and NUCHEMICS respectively when subjecting the NMR structures to energy minimization prior to chemical shift prediction using the Generalized Born with surface area (GB/SA) implicit solvent model. This improvement is observed across all RNA structures and suggests that some uncertainty in the NMR structure does contribute to the observed $CS^{RMSD}$.

The agreement between measured and predicted 1H chemical shifts is likely also affected by motional averaging, which is not accounted for during the calculation of $^1$H chemical shifts. For example, for pseudoknot preQ RNA, the poor $CS^{RMSD}$ value (0.64 ppm) improves when using the X-ray structure (0.36/0.38 pm when using SHIFTS/NUCHEMICS respectively) or when excluding highly flexible residues (0.32 ppm when residues with a root-mean-square fluctuation (RMSF)>2.0 Å are excluded). However, improved agreement was not observed when averaging the predicted CS data over the entire NMR bundle of structures ($CS^{RMSD}=0.37$ ppm and 0.35 ppm for SHIFTS and NUCHEMICS respectively).

Resolving power of $^1$H chemical shifts.

Next, examination of how well $^1$H chemical shifts can be used to resolve differences between competing RNA conformations was determined. For these studies, experimental $^1$H chemical shifts were used for three RNAs in a panel that contain representative RNA motifs and whose structures were determined with the use of RDCs. These include (i) a 32 nt RNA duplex structure ("duplex") containing a canonical A-form helix determined with a large number of RDC and residual chemical shift anisotropy (RCSA) data; (ii) a 14 nt hairpin containing a UUCG tetraloop ("tetraloop") for which a high resolution NMR structure has recently been reported based on an unprecedented amount of NMR input experimental data: nuclear Overhauser effect (NOE), derived-distances, torsion-angle dependent homonuclear and heteronuclear scalar coupling constants, cross-correlated relaxation rates and RDC; and (iii) a 36 nt preQ$_1$ riboswitch RNA structure determined with the aid of RDCs that contain a pseudoknot motif ("pseudoknot"). These structures fit the $^1$H chemical shifts with variable agreement (CS$^{RMSD}$=0.30/0.28, 0.28/0.21, 0.56/0.58 ppm for duplex, tetraloop, pseudoknot when using SHIFTS/NUCHEMICS respectively). The three RNAs have a similar density of $^1$H experimental chemical shifts (~2.8, 2.6 and 2.8 CS per residue for duplex, 14 mer and pseudoknot respectively).

Examination of how well the agreement between the measured and predicted $^1$H chemical shifts for use to distinguish between related RNA conformations. For each of the three RNA structures, a broad distribution of 8000 conformations spanning native and denatured conformations was used by carrying out high temperature MD simulations (see Methods). The resulting pool of conformations superimpose with native structure with an average heavy atom RMSD of 6.0±4.2, 3.5±2.6, and 5.6±3.0 Å for duplex, tetraloop, and psuedoknot, respectively. $^1$H chemical shifts were then calculated for each conformer within each pool using SHIFTS and NUCHEMICS. The CS$^{RMSD}$ value was then computed for each conformer and this compared to the heavy atom root-mean-square deviation between the conformer and the native conformation (structure$^{RMSD}$).

The value of CS$^{RMSD}$ generally decreases with decreasing structure$^{RMSD}$ particularly for structure$^{RMSD}$>4 Å. These data suggest that the CS data can resolve RNA structures to within 4 Å. The continued decrease of CSRMSD for structure$^{RMSD}$SD<4 Å for UUCG suggests an even stronger structure resolving power. This is likely due to the compact and well known high stability of the UUCG structure, in which fluctuations away from the native structure tend to involve coordinated movements of several bases that can lead to large changes in ring current effects and therefore the predicted chemical shifts. By contrast, motions in duplex and pseudoknot may preserve aspects of stacking interactions and therefore affect the chemical shift data to a lesser extent.

Our analysis suggests that $^1$H chemical shifts can resolve RNA structure to <4 Å resolution. Out of the broad conformational pool that was generated for our three target RNAs, the conformation that best satisfies the measured $^1$H chemical shifts according to SHIFTS/NUCHEMICS (i.e., conformation that yields the lowest CS$^{RMSD}$) superimposes with the native structures with structure$^{RMSD}$ of 2.3/1.9, 1.4/1.4, and 2.9/3.7 Å for duplex, tetraloop and psuedoknot, respectively. Although smaller agreement is observed for pseudoknot, the structureRMSD improves significantly when excluding flexible regions (structure$^{RMSD}$=1.7 and 2.2 Å relative to the X-ray and NMR). Taken together, the presented results strongly suggest that $^1$H chemical shifts can already be implemented as powerful constraints in RNA structure determination.

Use of $^1$H chemical shifts in constructing RNA dynamic ensembles. In solution, chemical shifts are time-averaged over all conformations that are sampled at timescales faster than milliseconds. Studies on protein systems have established the ability to extract this dynamics information from measured chemical shift data. Experiments were developed to examine whether $^1$H chemical shifts can facilitate the determination of dynamic ensembles of RNA using the SAS approach, which was previously used to construct ensembles of RNA with the use of RDCs. Here, ensembles with increasing size are constructed in an attempt to find the smallest member ensemble (N) that can satisfies the time-averaged $^1$H chemical shifts. In this approach, N conformers are randomly selected from a pool typically generated using MD simulations, and the agreement between measured and predicted $^1$H chemical shift data is computed. Next, one conformer is randomly replaced with another conformer from the pool, and the agreement with measured $^1$H chemical shift data is re-examined and the newly selected conformer is either accepted or rejected based on the Metropolis criteria. Using such a Monte-Carlo based approach, several iterations are carried out until convergence is reached, defined as achieving agreement between measured and calculated data to within the specified error (see below).

Figure 3:
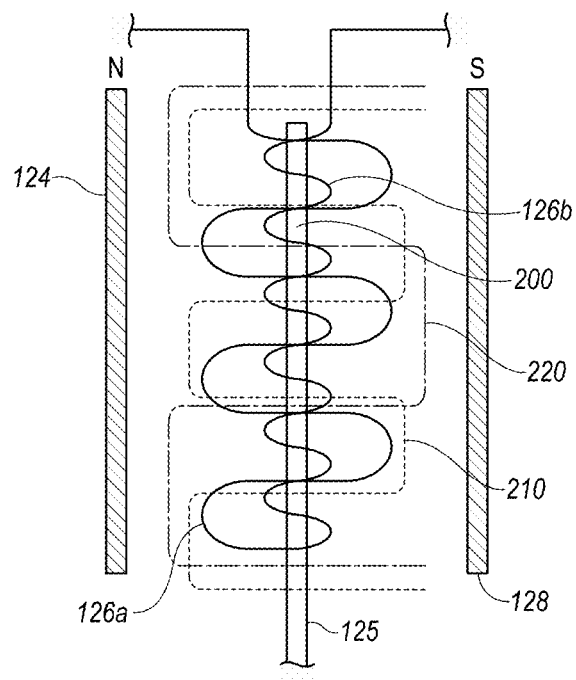
FIG. 3 shows a side elevational view of an exemplary NMR module in accordance with the teachings of the present disclosure.
Figure 4:
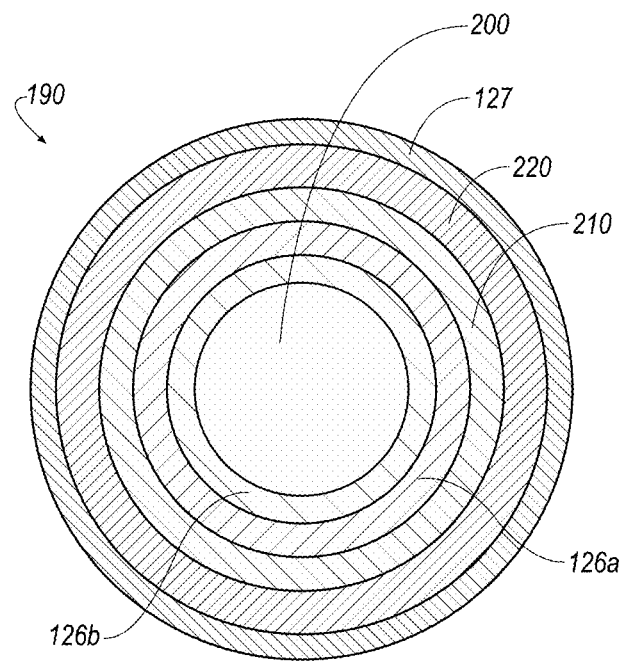
FIG. 4 shows a cross-sectional view of an exemplary NMR module in accordance with the teachings of the present disclosure.
Figure 5:
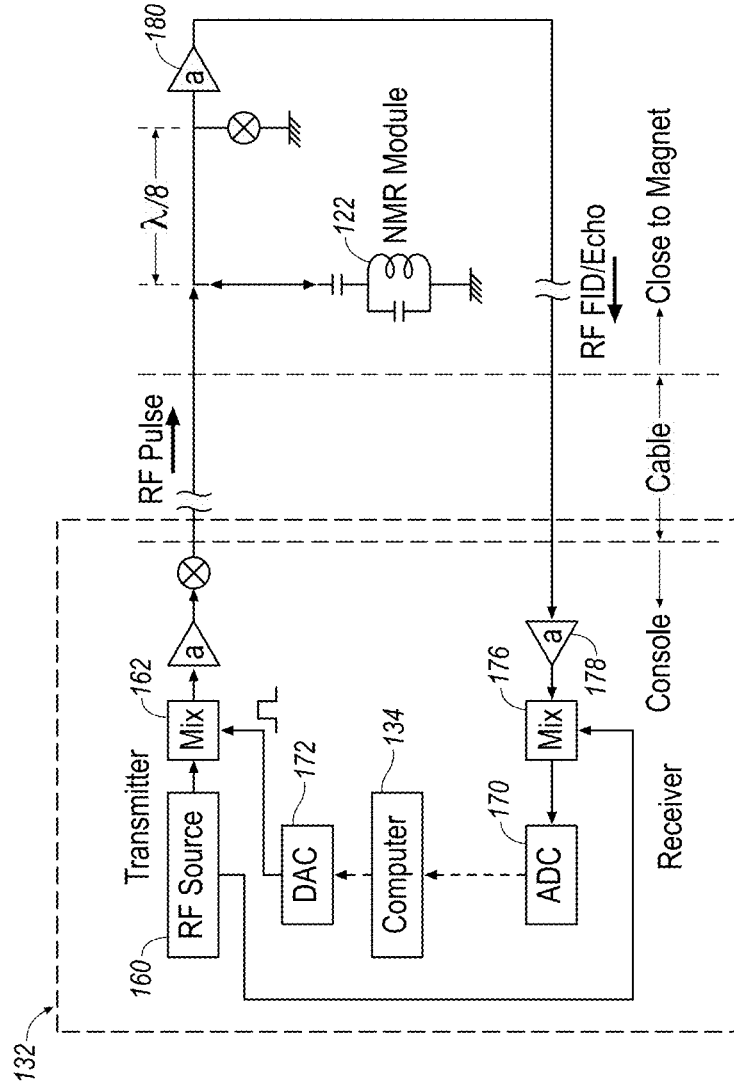
FIG. 5 depicts an exemplary schematic representation of the transmitter receiver component of the NMR device in electrical communication with the NMR module in accordance with the teachings of the present disclosure.
Figure 6A:
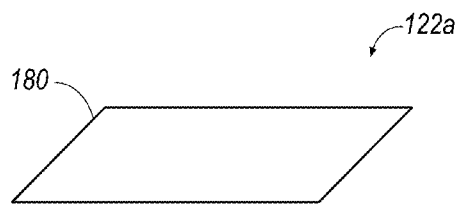
FIG. 6A-6D show an exemplary schematic representation of the synthesis of a flexible NMR device for use in some embodiments of the methods and devices in accordance with the teachings of the present disclosure.
Figure 6B:
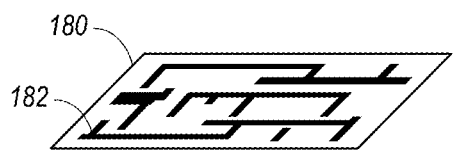
Figure 6C:
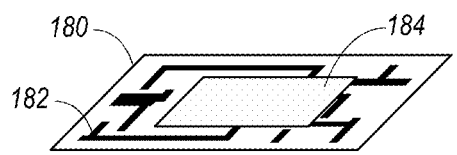
Figure 6D:
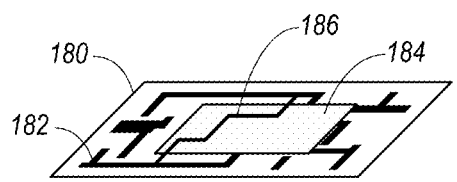
Figure 6E:
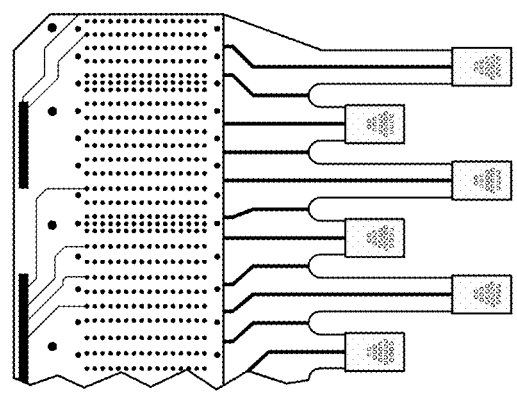
FIG. 6E shows an elevation view of an exemplary flexible NMR module in accordance with the teachings of the present disclosure.

Next, the utility of $^1$H chemical shifts in constructing RNA dynamic ensembles using simulated chemical shift and a known target "reference" ensemble was examined. A replica-exchange molecular dynamics (REMD) simulations was used to generate a broad conformation pool for the TAR hexa-nucleotide apical loop construct containing an 8-base-paired stem region. The TAR apical loop has previously been shown to undergo complex motions at multiple timescales and therefore provides a good model system for testing this approach. We then generated 21 reference ensembles that feature different levels of dynamics by randomly selecting a reference conformer from the 45,000 membered pool and then randomly selecting 100 conformers that are within 2, 3 and 4 Å of the reference conformer. In so doing, a total of 21 reference ensembles was generated (see Materials and Methods). The resulting ensembles were skewed to minimize overlap with the selection pool by replicating conformers that underrepresented in the reference pool. For each ensemble, 'experimental' ensemble-averaged H1', H2, H5, H6 and H8 chemical shifts were computed using NUCHEMICS. To simulate errors in predicting chemical shifts, the program "SHIFTS" was used to compute the chemical shifts when constructing the ensembles. (See FIG. 3B). This corresponds to ~0.24 ppm prediction error, as judged based on comparison of the average CS$_{RMSD}$ between SHIFTS and NUCHEMICS for the 18 benchmark RNAs studied here. One bond C—H RDCs were also computed assuming a fixed alignment tensor determined experimentally in Pf-1 phage. The RDCs were noise corrupted by adding random white noise with standard deviation of 2.0 Hz corresponding to the uncertainty in RDC measurements in elongated RNA.

In all cases, convergence was achieved for the chemical shift based selections at N=2 (CS$^{RMSD}$=0.13, 0.11 and 0.10 ppm for the 2, 3 and 4 Å reference ensembles; Table 2).

TABLE 2

Back-predicting chemical shifts and RDCs from chemical shift based ensembles.

| N | CS: RMSD (ppm)/R | | | RDC: RMSD (Hz)/R | | |
|---|---|---|---|---|---|---|
| 1 | 0.24/0.97 | 0.25/0.97 | 0.26/0.97 | 25.5/0.77 | 28.1/0.73 | 25.9/0.78 |
| 2 | 0.13/0.99 | 0.11/0.99 | 0.10/0.99 | 15.8/0.89 | 14.1/0.91 | 14.1/0.91 |
| 4 | 0.10/0.99 | 0.09/0.99 | 0.08/0.99 | 15.4/0.89 | 12.6/0.92 | 13.2/0.92 |

TABLE 2-continued

Back-predicting chemical shifts and RDCs from chemical shift based ensembles.

| N | CS: RMSD (ppm)/R | | | RDC: RMSD (Hz)/R | | |
|---|---|---|---|---|---|---|
| 6 | 0.09/0.99 | 0.08/0.99 | 0.08/0.99 | 14.7/0.90 | 12.2/0.92 | 12.5/0.92 |
| 8 | 0.09/0.99 | 0.08/0.99 | 0.07/0.99 | 14.4/0.90 | 11.3/0.92 | 12.3/0.92 |

Increasing the value of N for chemical shift selections was found to not lead to significant improvements in the chemical shift predictions (Table 2). By comparison, N~8 was required to achieve convergence for RDC and chemical shift+RDC selections; the $RDC^{RMSD}$ for the 2, 3 and 4 Å ensemble was 1.71, 1.72 and 1.72, and 1.73, 1.73 and 1.66 Hz, respectively. Next, experiments were prepared to investigate whether the chemical shift ensembles were able to recapitulate the reference ensembles RDCs. For the N=2 ensemble the $RDC^{RMSD}$=15.8, 14.1, and 14.1 Hz for the 2, 3 and 4 Å ensembles, respectively, and increasing N did not result in any significant improvement in RDC agreement (Table 2). The chemical shift ensembles therefore were unable to satisfy the RDCs to within the 2.0 Hz error thresholds; a similar trend was observed when back-predicting RDCs from ensemble constructed using experimental chemical shift (data not show) In contrast, the RDC ensembles predicted the chemical shifts to within the 0.24 ppm threshold ($CS^{RMSD}$=0.25, 0.24 and 0.23 for the 2, 3 and 4 Å ensembles, respectively).

To further interrogate the chemical shift ensembles, were used to the S-matrix method (Methods) to determine their structural overlap with the reference ensembles. We observed that for N=2 the $<S_{ij}>_A$ was 0.88, 0.78 and 0.84 for the 2, 3 and 4 Å reference ensembles (Table 3). Increasing N did not result in any significant enhancement in the overlap between the chemical shift and reference ensembles (Table 3).

TABLE 3

Overlap between chemical shifts based ensembles and reference ensembles.

| N | 2 Å | 3 Å | 4 Å |
|---|---|---|---|
| 1 | 1.47 | 1.59 | 1.56 |
| 2 | 0.88 | 0.78 | 0.84 |
| 4 | 0.76 | 0.64 | 0.65 |
| 6 | 0.75 | 0.61 | 0.56 |
| 8a | 0.75/0.44/0.44 | 0.59/0.44/0.41 | 0.53/0.43/0.39 |
| random | 1.06 | 0.93 | 0.78 |

By comparison, the $<S_{ij}>_A$ for randomly ensembles was 1.06, 0.93 and 0.78, indicating there was better correspondence between chemical shift and reference ensembles than the random and reference ensembles. However, the RDC, as well as the, chemical shift+RDC ensembles, exhibited much better overlap with the reference ensembles; for the N=8, $<S_{ij}>_A$ for 2, 3 and 4 Å ensembles was 0.44, 0.44 and 0.43, and 0.44, 0.41 and 0.39, respectively.

Taken together, the chemical shift based ensembles exhibited greater resemblance to the reference ensembles than the randomly constructed ensembles, they were unable to achieve the same degree of overlap as the RDC and chemical shift+RDC, and consequently were unable to adequately predict the reference ensemble RDCs. These effects can be attributed to the comparatively larger error threshold used to define convergence for chemical shift (threshold is ~22% of chemical shift total range) as compared to RDCs (threshold is ~2.5% of the RDC range). Indeed, repeating the simulations with zero error resulted in chemical shift ensembles that exhibited enhanced overlap with the reference ensembles, and thus, better predicted reference ensembles RDC (data not shown). The ability of a chemical shift ensemble to recover the reference ensemble is therefore limited by the accuracy of chemical shifts predictions. Currently, SHIFTS and NUCHEMICS predict $^1H$ chemical shifts to within ~0.30 ppm, slightly higher than the 0.24 ppm error threshold used to determine convergence in the theoretical simulations.

Conclusions. NMR structure determination of nucleic acids has traditionally been challenging due to the paucity of inter-proton NOE-derived distance constraints, extended nature of the structure, and high degree of flexibility. There has been a long-standing quest to measure different sources of structural information, and indeed, the measurement of RDCs has revolutionized the ability to determine the structure and dynamics of nucleic acids. There is now renewed interest in utilizing NMR chemical shift to solve RNA structure, as they are the most accessible and accurately measured NMR observable. In this report the inventors have demonstrated that $^1H$ chemical shifts can be used to resolve RNA structure, allowing discrimination of native structure from non-native states. The inventors show that using the programs SHIFTS and NUCHEMICS, which on average predict $^1H$ chemical shifts to within 0.30 ppm, that $^1H$ chemical shifts can be used to resolve with to within ~4 Å resolution. In time, as more accurate 1H chemical shift prediction methods emerge the resolution limit should decrease well below 4 Å. When combined with improvements in RNA structure prediction, it can be anticipated that methodologies such as CS-ROSETTA will evolve that allow high-resolution RNA structure determination based on chemical shift data alone.

Additional studies were performed to investigate whether $^1H$ chemical shifts could be used to generate accurate dynamic ensembles of RNAs. Using theoretical simulation on the hexa-nucleotide HIV-1 TAR apical loop our results indicate that though ensembles constructed using $^1H$ chemical shifts exhibited greater structural overlap with known reference ensembles than randomly constructed ensembles, they failed to achieve the same degree of overlap as the corresponding RDC ensembles. This result hinted to an inherent degeneracy in the chemical shifts ensembles and in fact, the chemical shift based ensembles were unable to reproduce the RDCs back-calculated from the reference ensembles. Here again, more accurate $^1H$ chemical shifts prediction methods should enable more accurate ensembles to be generated, as should the incorporation of chemical shifts from other nuclei e.g., $^{13}C$ and $^{15}N$.

Example 3

Predicting RNA $^{13}C$ Chemical Shifts Using Random Forests

The recent realization of the significant role played by ribonucleic acids (RNA) in orchestrating key cellular processes", as well as the recognition that many of these processes are accompanied by significant structural changes, has brought to the fore the need for efficient methods to determine tertiary structures of RNA, under a variety of experimental conditions. Nuclear magnetic resonance (NMR) spectroscopy has proven to be a value tool in RNA structure determination, Of particular interest to the field is the potential to utilize chemical shifts to aid in structure determination; chemical shifts, as source of structural information, are attractive as they are the most accurately measured NMR observable and are obtained before the typical NMR derived restraints (e.g., NOEs, J-Coupling and RDCs). Typically, acquisition of these NMR derived restraints, which are used in conventional structure determination to solve RNA structure, is both time and labor intensive. The ability to utilize chemical shifts in RNA structure determination will therefore represent a significant step forward that would improve efficiency, thus reducing the turnaround between chemical shift assignment and RNA structure determination Currently, however, chemical shifts are unutilized in RNA structure determination. This is in contrast to proteins, where chemical shifts are now routinely used to help predict, refine and validate structures and have been used to characterize ensemble of proteins including intrinsically disorder proteins. The success of these methods rely on the ability to rapidly and accurately predict protein chemical shifts from coordinates of structural models. In contrast to proteins, however, there is a paucity of methods for predicting RNA chemical shifts from structural models. This lack has significantly hampered the use of chemical shifts in RNA structure determination. This, in spite of accumulation of evidence that, especially in the case of $^{13}$C shifts, point to the existent of certain shift-structure relationships (see below).

The inventors describe what, to the best of their knowledge, is the first attempt to generate empirical models to predict $^{13}$C chemical shifts in RNA (SHIFTRNA). One approach to generate empirical methods to predict $^{13}$C chemical shifts would be to start from physically motivated mathematical models describing how the magnetic shielding around a carbon nucleus depends on its local environment, and then parameterize these models using a shift-structure database that map measured chemical shifts to calculable structural features. Here an alternate, data centric approach is taken. The assumption begins that with a few, easily calculated structural features, it can be used to adequately describe this structure around a carbon nucleus. No functional relationships between these features and chemical shifts are assumed. Instead, a supervised learning approach is used to reveal any internal structure in a shift-structure database and this data structure is then used to predict chemical shifts. To this end, a shift-structure database was compiled. A key concern when compiling a chemical shift database is whether or not the deposited shifts are consistently referenced. Recently, Aeschbacher et al. surveyed all the RNA carbon chemical shifts deposited in the BioMagResBank (BMRB: www.bmrb.wisc.edu) and found that some entries were improperly referenced or contained inconsistencies. Here the database was populated with measured chemical shift data taken from 20 RNA systems that were identified in that study to have 13C chemical shifts deposited in the BMRB that were properly and consistently referenced. In order to calculate the structures features (see below) needed to populate the structure portion of the database, structural models for each of the 20 RNAs where obtained from the PDB. Prior to calculation of the structure features, the first model from the PDB structure file was extracted and then energy minimized using AMBER ff99XoL force field.

Figure 8:
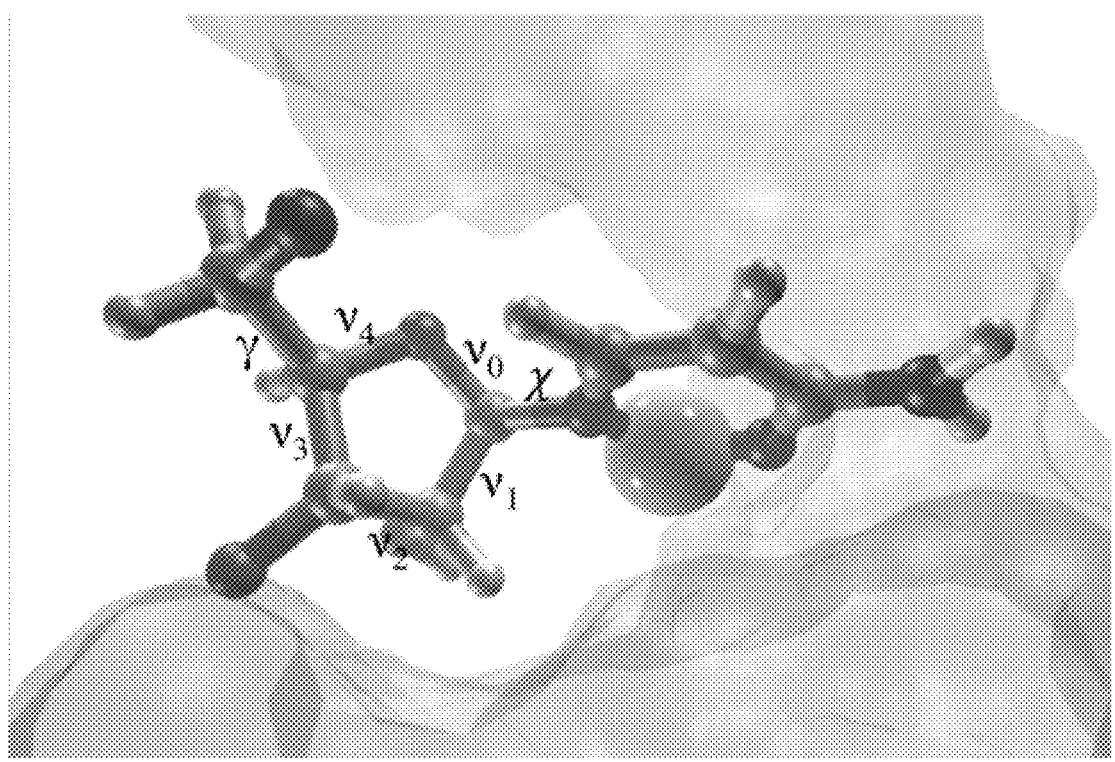
FIG. 8 the structural features used in one example of RNA to describe the local structure surrounding carbon nuclei. Shown are the torsion angles $\chi$, $\gamma$, $\nu_0$, $\nu_1$, $\nu_2$, $\nu_3$, and $\nu_4$ associate with a given carbon nucleus (yellow). Also shown is the representative surface of neighboring atoms would contribute to contact strength (Eq. 1) and local electrostatic potential (Eq. 2).

Next, a set of features was selected to describe the local structure around a carbon nucleus. RNA $^{13}$C chemical shifts have been shown to be sensitive to the torsion angles in the parent residue of the carbon nucleus, in particular, the glycosidic torsion angle χ5, and the exocyclic torsion angle 7. Additionally, $^{13}$C shifts appear to be sensitive to ring puckering effects which are explicitly be described by torsion angles v0, v1, v2,v3, and v4 of the ribose sugar. (See FIG. 8). In addition, the local contact strength (Ci) surrounding i. was computed. The contact strength Ci, which describes the steric environment around i, is calculated using:

$$C_i = \sum_j e^{-r_{ij}}$$

where rij is the distance between the carbon i and a heavy atom j that is within 20 Å of i. Finally, it has been demonstrated that 13C shifts can be calculated using bond polarization theory (BPT) model, highlighting the importance of accounting for polarizing effects of the electrostatic cloud surrounding the carbon nucleus. To account for the local electrostatic environment around the carbon nucleus the difference in electrostatic potential (ΔVij=Vi−Vj) between i, and the atom j with which it shares a bond was calculated. The electrostatic potential centered at atom i is calculated using:

$$V_i = \sum_i \frac{q_k}{T_{ik}}$$

where qk and rik are the charge of the atom k within 20 Å of atom i and the corresponding distance between them, respectively. The AMBER ff99 partial charges were used for these calculations. The local structure for every carbon in the database was therefore encoded by a feature vector with elements {χi, γi, vi0, vi1, vi2, vi3, vi4, Ci, Vi1, Vi2, Vi3, Vi4}. These feature vectors, together with measured chemical shifts, the identity of the carbon nucleus and associated residue name, comprised the completed shift-structure database. The final database consisted of 2425 entries. The database was then split into training and validation sets. The training set consisted of 75% of the complete database and the validation set, the remaining 25%.

Figure 9A:
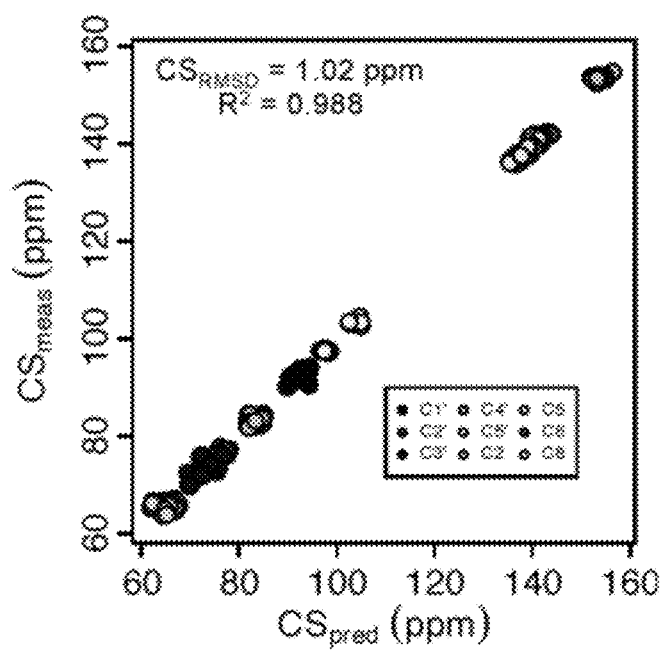
FIG. 9A depicts a non-limiting example of the subject matter described herein, for example Measured vs. SHIFT-RNA predicted $^{13}$C chemical shifts. Correlations plots comparing measured and predicted $C_1'$, $C_2'$, $C_3'$, $C_4'$, $C_5'$, $C_2$, $C_5$, $C_6$ and $C_8$ chemical shifts in the validation set.
Figure 9B:
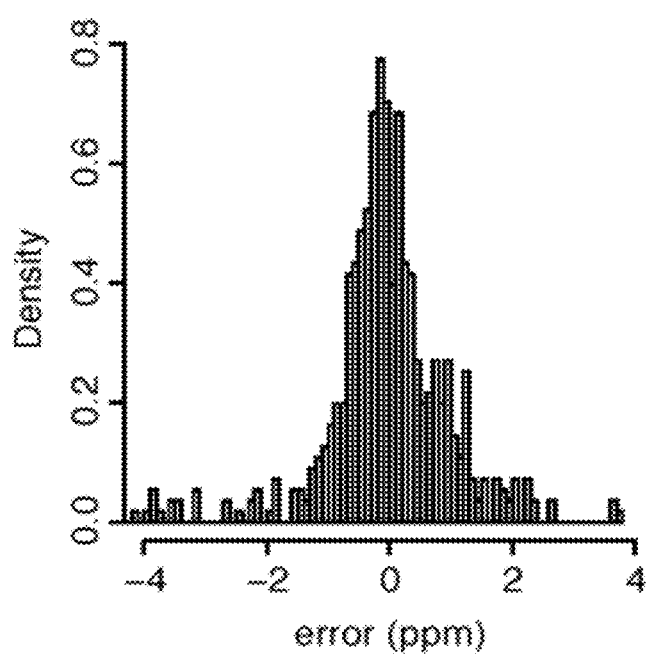
FIG. 9B shows an exemplary histogram of prediction errors. The $CS_{RMSD}$ and $R^2$ are 1.02 ppm and 0.998, respectively.

Using the shift-structure training set, the random forest (RF) method was used to generate empirical models to predict 13C chemical shifts. Despite its underlying simplicity, the RF approach has shown the ability to generate highly accurate predictors 31. To carryout random forest regression the random Forest library in the R-package is used. RF training was independently applied to the C1', C2', C3', C4', C5', C2, C5, C6 and C8 nuclei. As such, separate C1', C2', C3', C4', C5', C2, C5, C6 and C8 predictors (collectively referred to as SHIFTRNA predictors) were generated. In each RF training session, 5oo random trees were grown, and during the tree building process, four of the structure features were randomly chosen to determine the split at each node in the tree. Shown in FIG. 9a are the correlation plots between measured and SHIFTRNA predicted C1', C2', C3', C4', C5', C2, C5, C6 and C8 shifts in the validation set. The root mean square difference between predicted and measured chemical shifts (CSRMSD) was 1.02 ppm and the corresponding $R^2$ was 0.988, indicating excellent agreement between measured and predicted shifts. The CSRMSD value of 1.02 ppm is comparable that obtained for the predictions of $^{13}C$ chemical shifts in proteins. PROSHIFT and SHIFTX2, for example, predict $^{13}C$ chemical shifts with an accuracy ~1.3 ppm and 0.4-1.0 ppm, respectively.

As a demonstration of the utility of the SHIFTRNA predictors, attempts were made to use the predicted shifts to resolve native RNA structure from a pool consisting of native and decoy models. As a model system, the UUCG tetra-loop containing 14 mer stem-loop RNA was used. This 14 mer RNA is a good model system since, in addition to the availability of a complete set of chemical shifts, a high-resolution structure has been recently solved (PDBID: 2KOC). It should be noted that the shift-structure data for the 14 mer was excluded from the training set used to generate SHIFTRNA predictors. Decoy models of 14 mer RNA, exhibiting 4 secondary structure arrangements (1 native; 3 decoys), were built using the MCSYM webserver. For each secondary structure arrangement, the 20 lowest energy models were selected and combined with the 20 models taken from the 2KOC. From each model in the combined pool, the matrix of structure features were generated, the shifts predicted using SHIFTRNA, and then the CSRMSD computed.

Figure 10A:
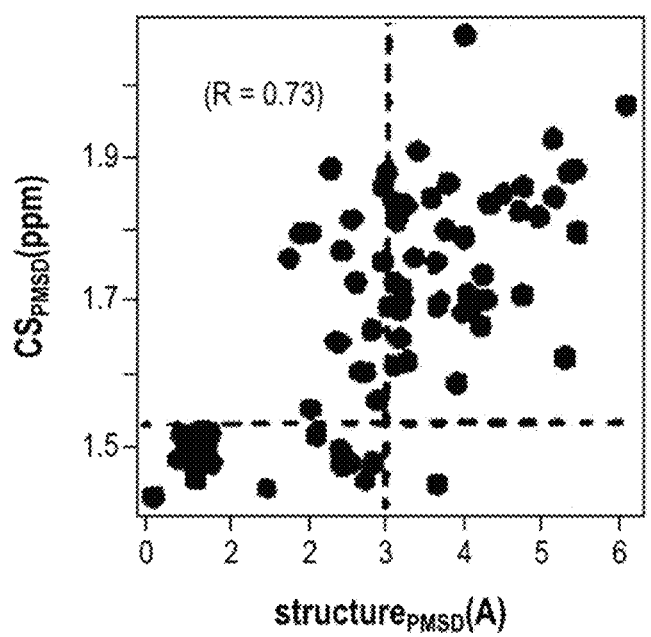
FIG. 10A shows an exemplary correlation plot between CSRMSD and structure$_{PMSD}$. Data from the native NMR ensemble and MCSYM models are shown in red and blue, respectively. Data points corresponding to MCSYM models with the lowest and highest $CS_{RMSD}$ are highlighted in orange and green, respectively.
Figure 10B:
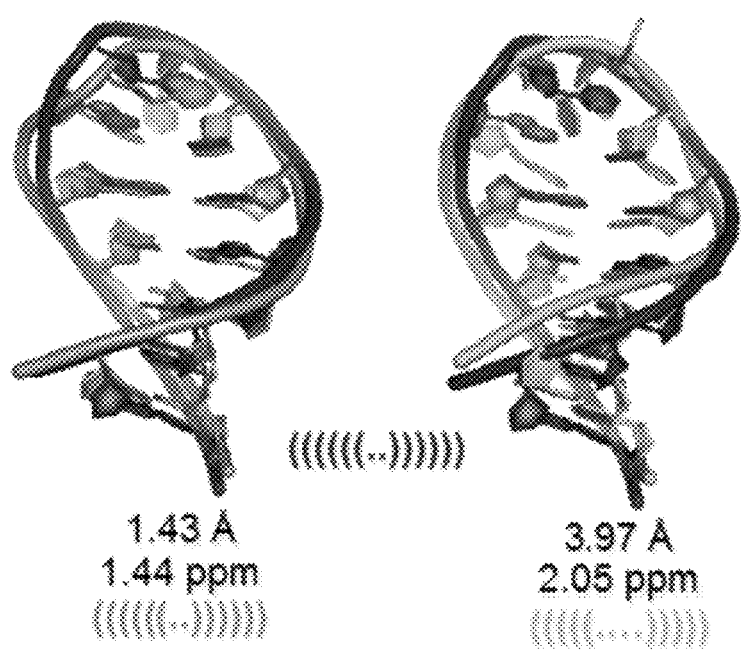
FIG. 10B shows an exemplary schematic diagram overlay of the NMR model 1 (red) with MCSYM models that exhibited the lowest (orange) and the highest (green) $CS_{RMSD}$. Included below each figure are the structure$_{RMSD}$, $CS_{RMS}$ and the corresponding secondary structure of the MCSYM models.

FIG. 9a shows the correlation between $CS_{RMSD}$ between measured and SHIFTRNA predicted chemical shifts, and the heavy atom structural RMSD (structure$_{RMSD}$) relative to model 1 in 2KOC. The plot reveals a strong and positive correlation between $CS_{RMSD}$ and structure$_{RMSD}$ (Pearson correlation coefficient R~0.73). As a consequence of this correlation, structures with small $CS_{RMSD}$ also exhibit small structure$_{RMSD}$. Encouragingly, the set of structures taken from the high resolution NMR ensemble exhibited the lowest $CS_{RMSD}$ (FIG. 10a), while the MCSYM models generally exhibited higher $CS_{RMSD}$. However, all but one of the decoy structures with $CS_{RMSD}<1.55$ ppm were within 3.0 Å of the native structure, with the structure with the lowest $CS_{RMSD}$ (1.44 ppm) having a structure$_{RMSD}$ of 1.43 Å (FIG. 10b). In contrast, the decoy structure with the largest $CS_{RMSD}$ (2.05 ppm) had a structure$_{RMSD}$ of 3.97 Å (FIG. 10b). In accordance with these findings the secondary structure of the models with the lowest $CS_{RMSD}$ recapitulated the secondary structure of the native 14 mer RNA (FIG. 10b) while the structure with the largest $CS_{RMSD}$ did not. These results clearly demonstrate that the SHIFTRNA predicted $^{13}C$ chemical shifts capture sufficient structural detail to be able to resolve RNA structure with near atomic accuracy, and more fundamentally suggest that ability to incorporate measured $^{13}C$ shifts within the RNA structure prediction/determination workflow.

The inventors present herein the first empirical models believed to predict $^{13}C$ chemical shifts in RNA. In spite of the small dataset used, and the simplicity of i) the structural features used to describe the local structure surrounding a given carbon nucleus, and ii) the random forest regression approach employed, the models were able predict $^{13}C$ chemical shifts with a $CS_{RMSD}=1.02$ ppm and with an $R^2=0.988$ (FIG. 9a). Encouragingly, predicted $^{13}C$ shifts were used to resolve RNA structure of the benchmark 14 mer stem loop RNA to ~1.4 Å of the native structure, explicitly demonstrating for first time the utility of incorporating $^{13}C$ shifts within the RNA structure determination and prediction process. As the database of RNAs for which both chemical shifts and structures are available expands, the accuracy of these models will improve. The work presented here should pave the way for the utilization of $^{13}C$ chemical shifts, and chemical shifts in general, in RNA structure prediction, refinement and/or validation.

Example 3

Solving the A-Site Structure

Figure 11A:
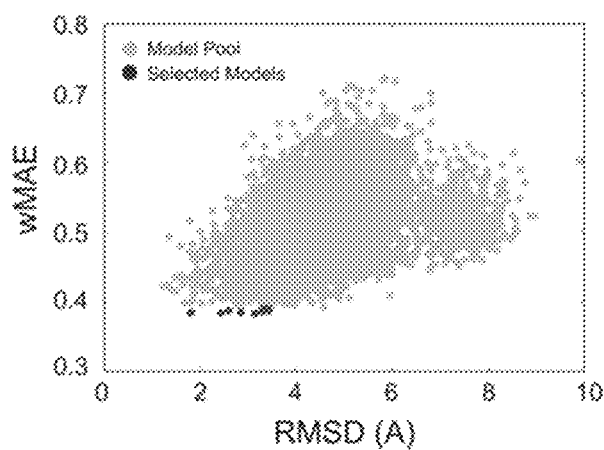
FIG. 11A-11C show exemplary A-site data.
Figure 11B:
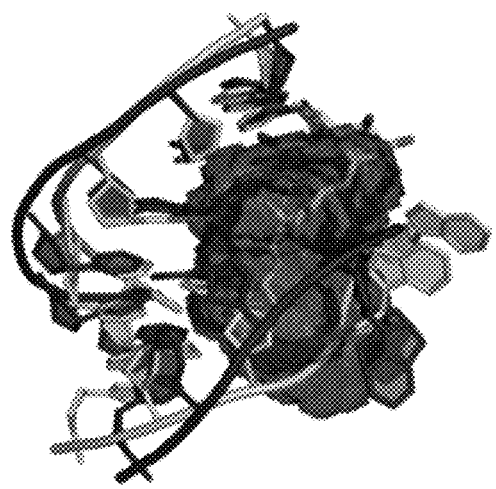

The technology described herein was established using the apramycin-bound bacterial ribosomal A-site structure. A-site is a well-studied RNA that undergoes an induced-fit structural change on binding small molecule antibiotics. Specifically, A1492 and A1493 loop from inside to outside the helix on small molecule binding, which in the ribosome signals acceptance of a codon-anticodon pair effectively eroding translational fidelity leading to bacterial death. In order to test whether the chemical shifts can be used to solve the A-site bound structure, we attempted to solve the 2.7 Å resolution apramycin-bound A-site x-ray structure (PDB ID#1YRJ) using only NMR chemical shifts and a newly developed method adapted from our recent publication. Briefly, apramycin-bound A-site chemical shifts were downloaded from the Biomagnetic Resonance Databank and re-referenced using the Aeschbacher method. The A-site secondary structure was input into CONSTRUCTOR and 10,000 3D models were generated. For each of the 10,000 models, chemical shifts were predicted using the algorithms developed using ND2S and compared to the experimental chemical shifts to calculate the weighted mean absolute error (wMAE; see ref. 30 for a detailed explanation). Using a wMAE accuracy cutoff of 0.4, the top 10 models were selected as putative bound structures (FIG. 11A). The top ten structures were in good agreement with 1YRJ exhibiting RMSDs from 1.8-3.3 Å compared to the 10,000 model pool which had RMSDs of 1.2-9.9 Å. Consistent with previous studies, in all ten structures A1492 and A1493 were flipped out of the helix exposing a clear apramycin binding pocket. In order to select the bound structure, small molecule binding pockets were identified for each of the 10 structures using fpocket (min-radius=3, max-radius=8, no-spheres=25, inter-cluster dis.=5), and apramycin was docked into each binding pocket using NymrDock (Nymirum's proprietary computational docking software). On docking of apramycin, one structure having RMSD of 2.43 Å compared to 1YRJ, gave rise to a statistically significant better score (−57 kcal/mol) than the other nine (range: −45 to −33 kcal/mol). This docked structure was selected for further refinement. Using tleap[39] and the Amber ff99bsc0chiOL forcefield, the structure was setup using a TIP3P water model, neutralized using Na+ ions, and subjected to 10,000 steps of energy minimization using NAMD[40]. After refinement, the RMSD was 2.2 Å compared to 1YRJ and the RNA formed almost an identical apramycin binding pocket (FIG. 11B) confirming the technology described herein can solve the high-resolution bound A-site structure.

As mentioned above, on binding small molecule antibiotics, A-site forms a similar structure where A1492 and A1493 flip out of the helix, which is starkly different than the unbound A-site structure. The A-site structure solved using the technology described herein exhibits this bound-state A-site conformation. To test whether the A-site structure solved using the technology described herein is able to identify other A-site binders in a simulated hit identification campaign, we virtually screened a library of 60 known A-site binders and a library of 1792 decoy compounds.

Figure 11C:
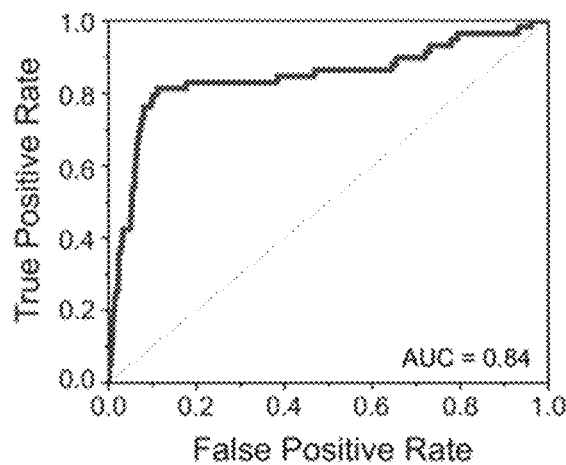

Since many A-site binders are cationic, to generate the decoy set, all compounds with a formal charge ≥+1 were selected from the Directory of Useful Decoys (http://dud.docking.org/). All compounds were virtually screened against the A-site structure solved using the technology described herein using NymrDock and the low score for each compound recorded. Using receiver operating characteristic analysis, the docking results show that the A-site structure solved using the technology described herein significantly enriches the virtual screen (AUC=0.84) and identifies 45 of 60 binders within the top 10% (188 of 1852) of the screen (FIG. 11C). Overall, this analysis confirms the technology described herein (1) solves high-resolution bound-state structures, (2) identifies druggable binding pockets, and (3) identifies chemically diverse small molecule binders.

Example 4

Figure 12A:
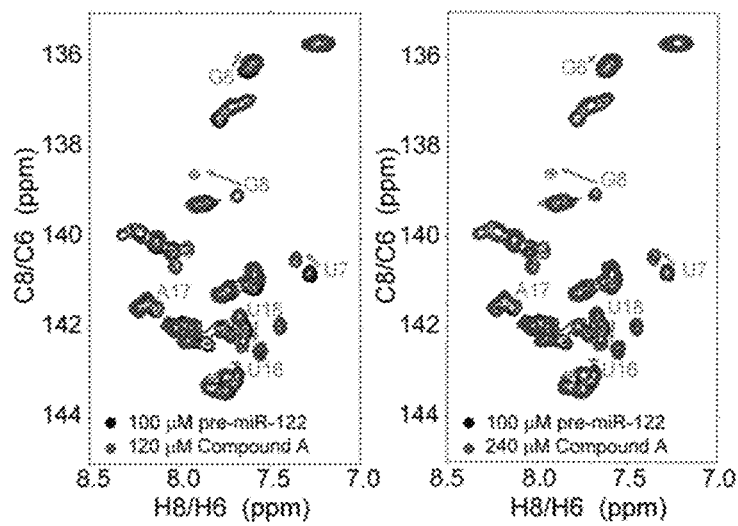
FIG. 12A-12B show exemplary pre-miR-122 data.
Figure 12B:
Figure 13C:
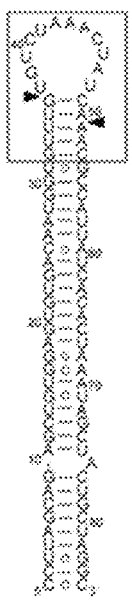
Figure 13C:
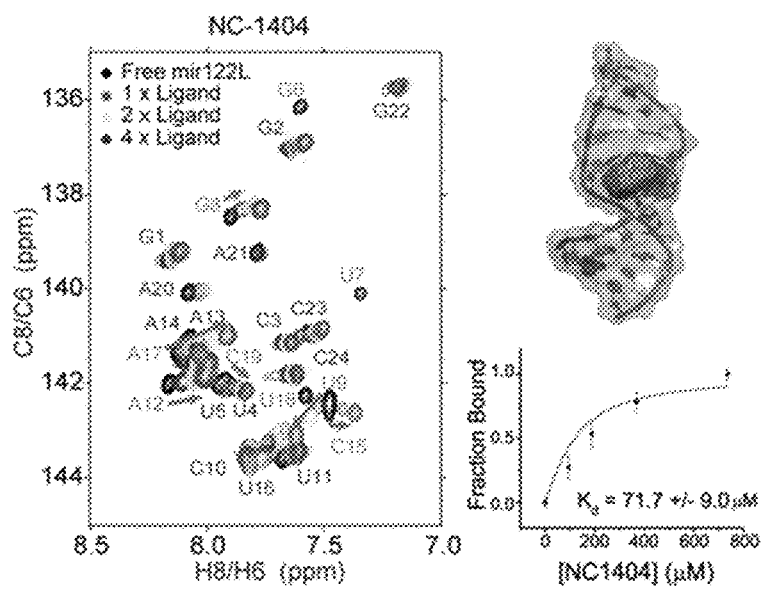
Figure 13C:
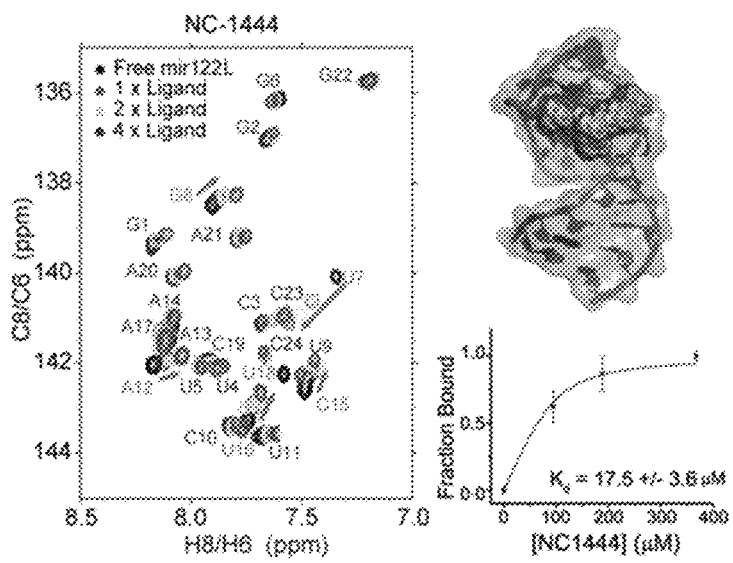

Pre-miR-122 Binding Pockets Identify Biochemically-Active Drug-Like Small Molecules Because pre-miR-122 is cleaved near the helix-apical loop interface, the apical loop was targeted to identify binding pockets. The pre-miR-122 apical loop is 12 residues long, has no identifiable base-pairs, and exhibits large resonance intensities (data not shown) suggesting it is highly dynamic. Given the size and plasticity of the loop, it was hypothesized that the loop could assume different conformations to bind small molecules. To identify small molecule binding pockets, each of the 60 small molecules in Nymirum's small molecule library was screened against the pre-miR-122 loop using NMR titration experiments. Two small molecules, NC1404 (9-aminoacridine) and NC1444 (L-arg-p-nitroanilide), were identified to bind with $K_d$s of 71.7±9.0 μM and 17.6±3.25 μM respectively (FIGS. 12A and 12B). Using the same procedure detailed for A-site, bound-state chemical shifts for NC1404 and NC1444 were measured, used to solve a bound-state pre-miR-122 structure and a binding pocket for each compound was identified (FIGS. 12A and 12B). Interestingly, the bound-state chemical shifts for each compound were drastically different, which is consistent with the different binding pockets identified for NC1404 and NC1444. Further, the binding pockets for NC1404 and NC1444 are consistent with previous studies: NC1404, which is known to bind nucleic acids through stacking interactions, stacks between G6 and U7 with stabilizing hydrogen-bonds to the U18 nucleobase, and NC1444 binds the major groove, consistent with binding modes previously identified against the Tau RNA (data not shown).

To identify drug-like small molecules that bind pre-miR-122 and alter Dicer processing, each structure was subjected to a virtual screen with over 6 million small molecules using NymrDock. Applying criteria that (1) accounts for whether a small molecule is predicted to bind one or both structures, and (2) ensures selection of a broad drug-like chemical space, 2500 drug-like small molecules were identified as putative binders. Each of the 2500 small molecules were tested to inhibit pre-miR-122 processing using an in-vitro Dicer processing assay of which, 41 were identified as single point hits. The 41 hits were tested for dose-response activity, and two compounds, Compounds A and B were dose responsive inhibitors with $IC_{50}$s of 105+4.2 μM and 15017.8 μM, respectively (data not shown). Both compounds were confirmed to maintain activity in the presence of excess tRNA confirming selectivity. To confirm Compounds A and B bound pre-miR-122 and not Dicer to inhibit processing, NMR binding studies were conducted. On addition of Compound A or B, specific chemical shift perturbations and resonance intensity modulations were identified. Residues G6, U7, U16, A17, U18, and C19 exhibit marked changes indicating that the compounds specifically bind pre-miR-122 (FIG. 12A). Also, consistent with the weaker activity of Compound B, less chemical shift perturbation and intensity changes are observed when compared to addition of Compound A. Strikingly, both compounds are predicted to bind the NC1404 structure and consistent with this prediction, both compounds cause similar chemical shift changes of residues located in the predicted binding pocket (e.g., example U7 and G8 show slow-exchange chemical shift changes on addition of each compound). Further, the primary amine in both compounds replaces the NC1404 hydrogen-bond to U18 showing that specific binding pocket interactions were exploited. This study demonstrates: (1) the technology described herein exploits atomic-resolution binding pocket interactions to identify diverse drug-like small molecules, and (2) arguably weak binders like NC 1404 and NC 1444 give rise to well-defined binding pockets that identify drug-like binders.

The embodiments and the examples described herein are exemplary and not intended to be limiting in describing the full scope of compositions and methods of the present technology. Equivalent changes, modifications and variations of some embodiments, materials, compositions and methods can be made within the scope of the present technology, with substantially similar results.

What is claimed is:

1. A method for identifying a binding pocket in a polynucleotide, the method comprising:
   a) providing a polynucleotide sample comprising a polynucleotide, the polynucleotide comprising at least one nucleotide isotopically labeled with one or more atomic labels comprising $^2$H, $^{13}$C, $^{15}$N, $^{19}$F and $^{31}$P;
   b) admixing with the polynucleotide sample one or more additional molecules comprising one or more of: a small molecule, a protein, a nucleic acid, an ion, a salt, and an atom;
   c) obtaining an NMR spectrum of the polynucleotide sample using an NMR device;
   d) determining a chemical shift of the one or more atomic labels;
   e) determining a 3-D atomic resolution structure of the polynucleotide from the chemical shifts determined in step (d) by
      (i) generating a plurality of theoretical structural polynucleotide 2-D models using the nucleotide sequence and one or more 2-D structure predicting algorithms;
      (ii) generating a plurality of theoretical structural polynucleotide 3-D models using a 3-D structure predicting algorithm using the plurality of theoretical structural polynucleotide 2-D models generated in (i) and optionally one or more known and/or assumed polynucleotide 2-D models;
      (iii) generating a predicted chemical shift set for each of the plurality of theoretical structural polynucleotide 3-D models generated in (ii);
      (iv) comparing the predicted chemical shift set of each of the plurality of theoretical structural polynucleotide 3-D models to the chemical shift(s) determined in (d); and
      (v) selecting a theoretical structural polynucleotide 3-D model having an agreement between the respective predicted chemical shift set and the chemical shift(s) determined in (d) as the 3-D atomic resolution structure;
   f) identifying a binding pocket in the 3-D atomic resolution structure of the polynucleotide; and
   g) validating the 3-D atomic resolution structure and binding pocket by:
      (i) virtually screening one or more small molecules against the one or more binding pockets, wherein the virtual screening process identifies putative small molecule hits; and
      ii) testing one or more small molecule hits from the virtual screen using an experimental assay comprising a biochemical or biophysical technique.

2. The method according to claim 1, wherein the binding pocket is identified using a binding pocket identification software.

3. The method according to claim 1, further comprising the step: generating one or more refined 3-D atomic resolution structures by refining the selected one or more theoretical structural polynucleotide 3-D models using a modeling software that performs one or more functions comprising energy minimization and/or a molecular dynamics simulation.

4. The method according to claim 3, further comprising the step: identifying a binding pocket in the one or more refined 3-D atomic resolution structures.

5. The method according to claim 1, wherein the predicted chemical shift set is generated by comparing each theoretical structural polynucleotide 3-D model with an NMR data-structure database.

6. The method according to claim 5, wherein generating the predicted chemical shift set comprises:
   a) calculating a polynucleotide structural metric comprising atomic coordinates, stacking interactions, magnetic susceptibility, electromagnetic fields, or dihedral angles from one or more experimentally determined polynucleotide 3-D structures;
   b) using a regression algorithm to generate a set of mathematical functions or objects that describe relationships between experimental chemical shifts and the polynucleotide structural metric of the experimentally determined 3-D polynucleotide structures;

c) calculating a polynucleotide structural metric for each of the theoretical structural polynucleotide 3-D models;

d) inputting the polynucleotide structural metric for each of the theoretical structural polynucleotide 3-D models into the set of mathematical functions or objects to generate the predicted chemical shift set.

7. The method according to claim 6, wherein the regression algorithm is a machine learning algorithm selected from the group consisting of a Random Forest algorithm, a neural network, and any combination thereof.

8. A method for identifying a small molecule that binds a polynucleotide, the method comprising:
   a) identifying one or more binding pockets in a polynucleotide by:
      (i) providing a polynucleotide sample comprising a polynucleotide, the polynucleotide comprising at least one nucleotide isotopically labeled with one or more atomic labels comprising $^2H$, $^{13}C$, $^{15}N$, $^{19}F$ and $^{31}P$;
      (ii) admixing with the polynucleotide sample one or more additional molecules comprising one or more of: a small molecule, a protein, a nucleic acid, an ion, a salt, and an atom;
      (iii) obtaining an NMR spectrum of the polynucleotide sample using an NMR device;
      (iv) determining a chemical shift of the one or more atomic labels;
      (v) determining a 3-D atomic resolution structure of the polynucleotide from the chemical shifts determined in step (iv); and
      (vi) identifying a binding pocket in the 3-D atomic resolution structure of the polynucleotide;
   b) virtually screening one or more small molecules against the one or more binding pockets, wherein the virtual screening process identifies putative small molecule hits;
   c) testing one or more small molecule hits from the virtual screen using an experimental assay.

9. The method according to claim 8, wherein the experimental assay comprises a biochemical or biophysical technique.

10. The method according to claim 8, wherein determining the 3-D atomic resolution structure comprises the method of:
   a) generating a plurality of theoretical structural polynucleotide 2-D models using the nucleotide sequence and one or more 2-D structure predicting algorithms;
   b) generating a plurality of theoretical structural polynucleotide 3-D models using a 3-D structure predicting algorithm using the plurality of theoretical structural polynucleotide 2-D models and optionally one or more known and/or assumed polynucleotide 2-D models;
   c) generating a predicted chemical shift set for each of the plurality of theoretical structural polynucleotide 3-D models;
   d) comparing the predicted chemical shift set to the chemical shift(s) of the one or more atomic labels; and
   e) selecting one or more theoretical structural polynucleotide 3-D models having an agreement between the respective predicted chemical shift set and the chemical shift(s) of the one or more atomic labels as the one or more 3-D atomic resolution structures.

11. The method according to claim 10, further comprising the step: generating one or more refined 3-D atomic resolution structures by refining the selected one or more theoretical structural polynucleotide 3-D models using a modeling software that performs one or more functions comprising energy minimization and/or a molecular dynamics simulation.

12. The method according to claim 11, further comprising the step: identifying a binding pocket in the one or more refined 3-D atomic resolution structures.

13. The method according to claim 10, wherein the predicted chemical shift set is generated by comparing each theoretical structural polynucleotide 3-D model with an NMR data-structure database.

14. The method according to claim 13, wherein generating the predicted chemical shift set comprises:
   a) calculating a polynucleotide structural metric comprising atomic coordinates, stacking interactions, magnetic susceptibility, electromagnetic fields, or dihedral angles from one or more experimentally determined polynucleotide 3-D structures;
   b) using a regression algorithm to generate a set of mathematical functions or objects that describe relationships between experimental chemical shifts and the polynucleotide structural metric of the experimentally determined 3-D polynucleotide structures;
   c) calculating a polynucleotide structural metric for each of the theoretical structural polynucleotide 3-D models; and
   d) inputting the polynucleotide structural metric for each of the theoretical structural polynucleotide 3-D models into the set of mathematical functions or objects to generate the predicted chemical shift set.

15. The method according to claim 14, wherein the regression algorithm is a machine learning algorithm selected from the group consisting of a Random Forest algorithm, a neural network, and any combination thereof.

* * * * *

SEQUENCE LISTING

```
<160> NUMBER OF SEQ ID NOS: 4

<210> SEQ ID NO 1
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1 auugc                                                                       5

<210> SEQ ID NO 2
<211> LENGTH: 24
```

```
<212> TYPE: RNA
<213> ORGANISM: Homo sapiens

<400> SEQUENCE: 2
ggcuuguguc uaaacuauca agcc                                              24

<210> SEQ ID NO 3
<211> LENGTH: 22
<212> TYPE: RNA
<213> ORGANISM: Human immunodeficiency virus 1

<400> SEQUENCE: 3
uaucgagccu gggagcucga ua                                                22

<210> SEQ ID NO 4
<211> LENGTH: 85
<212> TYPE: RNA
<213> ORGANISM: Homo sapiens

<400> SEQUENCE: 4
ccuuagcaga gcuguggagu gugacaaugg uguuuguguc uaaacuauca aacgccauua       60
ucacacuaaa uagcuacugc uaggc                                             85
```